US007041681B2

(12) United States Patent
Breslin et al.

(10) Patent No.: US 7,041,681 B2
(45) Date of Patent: May 9, 2006

(54) COMPOUNDS AS OPIOID RECEPTOR MODULATORS

(75) Inventors: Henry J. Breslin, Lansdale, PA (US); Wei He, Audubon, PA (US); Robert W. Kavash, Glenside, PA (US)

(73) Assignee: Janssen Pharmaceutica N.V., Beerse (BE)

(*) Notice: Subject to any disclaimer, the term of this patent is extended or adjusted under 35 U.S.C. 154(b) by 0 days.

(21) Appl. No.: 10/400,006

(22) Filed: Mar. 26, 2003

(65) Prior Publication Data

US 2004/0010014 A1    Jan. 15, 2004

Related U.S. Application Data

(60) Provisional application No. 60/376,406, filed on Apr. 29, 2002.

(51) Int. Cl.
  *A61K 31/454*    (2006.01)
  *A61K 31/4725*   (2006.01)
  *C07D 401/04*    (2006.01)
  *C07D 401/14*    (2006.01)

(52) U.S. Cl. .............. 514/326; 546/210; 546/187; 546/146; 544/60; 544/128; 544/129; 544/360; 544/363; 514/316; 514/307; 514/252; 514/235.5; 514/227.8

(58) Field of Classification Search ............... 514/326, 514/316, 307, 235.5, 227.8, 252; 546/210, 546/187, 146; 544/128, 129, 360, 363, 60
See application file for complete search history.

(56) References Cited

U.S. PATENT DOCUMENTS

| 3,023,235 | A  | 2/1962  | Frederick      |
| 3,763,218 | A  | 10/1973 | Hohenlohe      |
| 4,563,306 | A  | 1/1986  | Ishida et al.  |
| 2002/0161189 | A1 | 10/2002 | Lazarus et al. |

FOREIGN PATENT DOCUMENTS

| EP | 0506468       | 9/1992  |
| FR | 2735776       | 12/1996 |
| JP | 5339240 A     | 12/1993 |
| WO | WO 96/06855 A1 | 3/1996  |
| WO | WO 02/36116 A2 | 5/2002  |

OTHER PUBLICATIONS

Obase, H. et al: "New Antihypertensive Agents. II. Studies on New Analog of 4-Piperidylbenzimidazolinones" Chemical and Pharmaceutical Bulletin, Pharmaceutical Society of Japan. Tokyo, Up. vol. 630, No. 2, 1982, pp. 474-483, XP000974108.
Tripp, et al.: "Synthesis of methylene- and carbonyl-bridged analogs of iodothyronines and iodothyroacetic acids". Journal of Medicinal Chemistry, American Chemical Society, Washington, U.S. vol. 16, No. 1, 1973, pp. 60-64, XP002113321.
Krenitsky, P.J. et al: "Preparation of the 14-membered 1,1-cyloisodityrosine subunit of RP 66453". Tetrahedron Letters, Elsevier Science Publishers, Amsterdam, NL, vol. 43, No. 3, Jan. 14, 2002, pp. 407-410, XP004329390.
Leonard, F. et al: "Unnatural amino acids. II. Congeners of DL-3-carboxy-4-methoxyphenylalanine". J. Med. Chem., vol. 10, 1967, pp. 478-481, XP00258212.
Database Crossfire Beilstein Online! Beilstein Institut zur Forderung der Chemischen Wissenscaften, Frankfurt am Main, DE: Database accession No. 5644822, XP002258213 & MAEDA, H. et al: Chem. Pharm. Bull., vol. 36, No. 1, 1988, pp. 190-201.
PCT International Search Report, PCT/US03/11872, Nov. 6, 2003.
Partial Internatioinal Search Report for PCT/US03/11872 dated Jul. 18, 2003 attached as Annex to Form PCT/ISA/206.
Gianfranco Balboni et al., "Opioid pseudopeptides containing heteroaromatic or heteroaliphatic nuclei", *Peptides* 2000, 21, pp. 1663-1671.
Gianfranco Balboni et al., "Evaluation of the Dmt-Tic Pharmacophore: Conversion of a Potent δ-Opioid Receptor Antagonist into a Potent δ Agonist and Ligands with Mixed Properties", J. Med. Chem. 2002, 45, 713-720.
Marnix, A. Hoitink et al., "Degradation of Azaglycinamido Residues in Model Tripeptides Derived from Goserelin", Journal of Pharmaceutical Sciences, vol. 89, No. 1, Jan. 200, pp. 108-114.
Severo Salvadori et al, "Evolution of the DMt-Tic Pharmacophonre: N-Terminal Methylated Derivatives with Extraordinary δ Opioid Antagonist Activity", J. Med. Chem. 1997, 40, 3100-3108.
D.S. Fries, "Analgesics", in *Principles of Medicinal Chemistry*, 4th ed.; W.O. Foye, T.L. Lemke, and D.A. Williams, Eds.; Williams and Wilkins: Baltimore, Md., 1995; pp. 247-269.
J.V. Aldrich, "Analgesics", *Burger's Medicinal Chemistry and Drug Discovery*, 5th Edition, vol. 3: Therapeutic Agents, John Wiley & Sons, Inc., 1996, pp. 321-441.
Pierre J.M. Riviere and Jean-Louis Junien, "Opioid receptors: Targets for new gastrointestinal drug development", Drug Development 2000, pp. 203-238.
Brian J. Marsden, Thi M.-D. Nguyen and Peter W. Schiller, "Spontaneous degradation via diketopiperazine formation of peptides containing a tetrahydroisoquinoline-3-carboxylic acid residue in the 2-position of the peptide sequence", Int. J. pept. Protein Res. 1993, 41 (3), pp. 313-316.

(Continued)

Primary Examiner—Charanjit S. Aulakh

(57) ABSTRACT

This invention is directed towards novel compounds as opioid receptor modulators, antagonists, and agonists useful for the treatment of opioid modulated disorders such as pain and gastrointestinal disorders.

33 Claims, No Drawings

OTHER PUBLICATIONS

Gianfranco Balboni et al., "Opioid pseudopeptides containing heteroaromatic or heteroaliphatic nuclei", *Peptides* 2000, 21, pp. 1663-1671.

Mark P. Wentland et al., "3-Carboxamido Analogues of Morphine and Naltrexone: Synthesis and Opioid Receptor Binding Properties", *Biorganic & Medicinal Chemistry Letters* 2001, 11, pp. 1717-1721.

Mark P. Wentland et al., "8-Carboxamidocyclazocine Analogues: Redefining the Structure-Activity Relationships of 2,6-Methano-3-benzazocines", *Biorganic & Medicinal Chemistry Letters* 2001, 11, pp. 623-626.

Philip L. Gould, "Salt selection for basic drugs", International Journal of Pharmaceutics, vol. 33, (1986) pp. 201-217.

Stephen M. Berge et al., "Pharmaceutical Salts", *Journal of Pharmacedutical Sciences*, 1977 (Jan.), vol. 66, No. 1, pp. 1-19.

Tao Ye, et al., "Synthesis of Chiral N-Protected α-Amino-β-Diketones from α-Diazoketones Derived from Natural Amino Acids", *Tetrahedron* 1992, vol. 48, No. 38, pp. 8007-8022.

Kouichi Kikuchi et al., "Syntheses and Structure-Activity Relationships of 5,6,7,8-Tetrahydro-5,5,8,8-tetramethyl-2-quinoxaline Derivatives with Retinoic Acid Recepton α Agonistic Activity",*J. Med. Chem*. 2000, 43, pp. 409-419.

Maeda, H. et al., Synthesis and Central Nervous System Actions of Thyrotropin-Releasing Hormone Analogs Containing a 1-Oxo-1,2,3,4-tetrahydroisoquinoline Moiety[1], Chem. Pharm. Bull. 36(1) 1988, 190-201.

Patent abstracts of Japan, vol. 18, No. 182, 1994, & JP 05 339240, 1993.

COMPOUNDS AS OPIOID RECEPTOR MODULATORS

This application claims benefit of provisional application 60/376,406 filed on Apr. 29, 2002.

FIELD OF THE INVENTION

The present invention is directed to novel opioid receptor modulators of formula (I). The invention further relates to methods for preparing such compounds, pharmaceutical compositions containing them, and their use in the treatment of opioid modulated disorders.

BACKGROUND OF THE INVENTION

The opioid receptors were identified in the mid-1970's, and were quickly categorized into three sub-sets of receptors (mu, delta and kappa). More recently the original three types of receptors have been further divided into sub-types. Also known is that the family of opioid receptors are members of the G-protein coupled receptor (GPCR) super-family More physiologically pertinent are the well established facts that opioid receptors are found throughout the central and peripheral nervous system of many mammalian species, including humans, and that modulation of the respective receptors can elicit numerous, albeit different, biological effects, both desirable and undesirable (D. S. Fries, "Analgesics", in *Principles of Medicinal Chemistry*, 4th ed.; W. O. Foye, T. L. Lemke, and D. A. Williams, Eds.; Williams and Wilkins: Baltimore, Md., 1995; pp. 247–269; J. V. Aldrich, "Analgesics", *Burger's Medicinal Chemistry and Drug Discovery*, 5th Edition, Volume 3: Therapeutic Agents, John Wiley & Sons, Inc., 1996, pp. 321–441). In the most current literature, the likelihood of heterodimerization of the sub-classes of opioid receptors has been reported, with respective physiological responses yet undetermined (Pierre J. M. Riviere and Jean-Louis Junien, "Opioid receptors: Targets for new gastrointestinal drug development", Drug Development 2000, pp. 203–238).

A couple biological effects identified for opioid modulators have led to many useful medicinal agents. Most significant are the many centrally acting mu opioid agonist modulators marketed as analgesic agents to attenuate pain (e.g., morphine), as well as peripherally acting mu agonists to regulate motility (e.g., loperamide). Currently, clinical studies are continuing to evaluate medicinal utility of selective delta, mu, and kappa modulators, as well as compounds possessing combined sub-type modulation. It is envisioned such explorations may lead to agents with new utilities, or agents with minimized adverse side effects relative to currently available agents (examples of side effects for morphine includes constipation, respiratory depression, and addiction potential). Some new GI areas where selective or mixed opioid modulators are currently being evaluated includes potential treatment for various diarrheic syndromes, motility disorders (post-operative ileus, constipation), and visceral pain (post operative pain, irritable bowel syndrome, and inflammatory bowel disorders) (Pierre J. M. Riviere and Jean-Louis Junien, "Opioid receptors: Targets for new gastrointestinal drug development" Drug Development, 2000, pp. 203–238).

Around the same time the opioid receptors were identified, the enkephalins were identified as a set of endogenous opioid ligands (D. S. Fries, "Analgesics", in *Principles of Medicinal Chemistry*, 4th ed.; W. O. Foye; T. L. Lemke, and D. A. Williams, Eds.; Williams and Wilkins: Baltimore, Md., 1995; pp. 247–269). Schiller discovered that truncating the original pentapeptide enkephalins to simplified dipeptides yielded a series of compounds that maintained opioid activity (Schiller, P. WO 96/06855). However one potential drawback cited for such compounds is the likelihood of their inherent instability (P. W. Schiller et al., Int. J. Pept. Protein Res. 1993, 41 (3), pp. 313–316).

More recently, a series of opioid pseudopeptides containing heteroaromatic or heteroaliphatic nuclei were disclosed, however this series is reported showing a different functional profile than that described in the Schiller works. (L. H. Lazarus et al., *Peptides* 2000, 21, pp. 1663–1671)

Most recently, works around morphine related structures were reported by Wentland, et al, where carboxamido derivatives morphine and it's analogs were prepared (M. P. Wentland et al., *Biorg. Med. Chem. Letters* 2001, 11, pp. 1717–1721; M. P. Wentland et al., *Biorg. Med. Chem. Letters* 2001, 11, pp. 623–626). Wentland found that substitution for the phenol moiety of the morphine related structures with a primary carboxamide led anywhere from equal activities up to 40 fold reduced activities, depending on the opioid receptor and the carboxamide. It was also revealed that any additional N-substitutions on the carboxamide significantly diminished the desired binding activity.

Compounds of the present invention have not been previously disclosed and are believed to provide advantages over related compounds by providing improved pharmacological profiles.

It is expected that opioid receptor modulators, agonists or antagonists may be useful in the treatment and prevention of various mammalian disease states, for example pain and gastrointestinal disorders such as diarrheic syndromes, motility disorders including post-operative ileus and constipation, and visceral pain including post-operative pain, irritable bowel syndrome and inflammatory bowel disorders.

It is an object of the present invention to provide opioid receptor modulators. It is a further object of the invention to provide opioid receptor agonists and opioid receptor antagonists. It is an object of the present invention to provide opioid receptor ligands that are selective for each type of opioid receptor, mu, delta and kappa. It is a further object of the present invention to provide opioid receptor ligands that modulate two or three opioid receptor types, mu, delta and kappa, simultaneously. It is an object of the invention to provide certain instant compounds that are also useful as intermediates in preparing new opioid receptor modulators. It is also an object of the invention to provide a method of treating or ameliorating a condition mediated by an opioid receptor. And, it is an object of the invention to provide a useful pharmaceutical composition comprising a compound of the present invention useful as an opioid receptor modulator.

SUMMARY OF THE INVENTION

The present invention provides opioid receptor modulators of Formula (I):

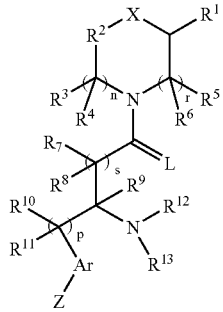

Formula (I)

wherein:
X is selected from a group consisting of O; S; N(R$^{14}$); and —(CR$^{15}$R$^{16}$)$_m$—,
   wherein:
   m is an integer from 0 to 2, and
   R$^{14}$, R$^{15}$, and R$^{16}$ are independently selected from the group consisting of hydrogen, C$_{1-4}$alkyl, and aryl; provided that only one of R$^{15}$ or R$^{16}$ can be C$_{1-4}$alkyl, or aryl;
   and the total core ring size of the ring containing X will not be greater than an eight membered ring;
R$^1$ is selected from the group consisting of benzimidazole, benzoxazole, benzothiazole, indole, phenyl,

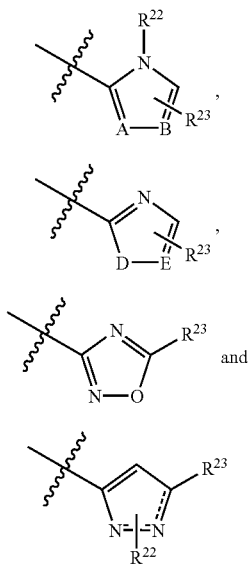

a-1 a-2 a-3 a-4 wherein
   A-B is selected from the group consisting of N—C, C—N, N—N and C—C;
   D-E is selected from the group consisting of O—C, S—C, and O—N;
   R$^{22}$ is a substituent attached to a ring nitrogen and is selected from the group consisting of hydrogen, C$_{1-4}$alkyl and aryl;
   R$^{23}$ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—R$^{40}$)—C(O)—NH$_2$ and C$_{1-6}$alkyl {wherein said alkyl is optionally substituted with a substituent selected from the group consisting of hydroxy, hydroxycarbonyl, C$_{1-4}$alkoxycarbonyl, aminocarbonyl, amino, aryl, (C$_{1-4}$)alkylaminocarbonyl, di(C$_{1-4}$)alkylaminocarbonyl, heteroarylamino, heteroaryloxy, aryl(C$_{1-4}$)alkoxy, and heteroaryl};
   R$^{40}$ is selected from the group consisting of hydrogen, C$_{1-6}$alkyl, C$_{1-6}$alkylcarbonyl, C$_{1-6}$alkoxycarbonyl, C$_{1-6}$alkylcarbonylamino, diC$_{1-6}$alkylcarbonylamino, aryl(C$_{1-6}$)alkyl, heteroaryl(C$_{1-6}$)alkyl, aryl, and heteroaryl;
   wherein when R$^1$ is benzimidazole, said benzimidazole is optionally substituted with one to two substituents independently selected from the group consisting of halogen, C$_{1-4}$alkyl, hydroxy, hydroxycarbonyl and aryl, with the proviso that when R$^1$ is benzimidazole, r, s and p are 0, n is 0 or 1, L is O and R$^3$, R$^4$, R$^9$, R$^{12}$ and R$^{13}$ are all hydrogen, Ar is not (4-OH)Phenyl or (4-OH-2, 6-diMe)Phenyl;
R$^2$ is a divalent radical —CH$_2$—CH$_2$— optionally substituted with a substituent selected from the group consisting of halogen and phenylmethyl, or is selected from the group of divalent radicals of the formula

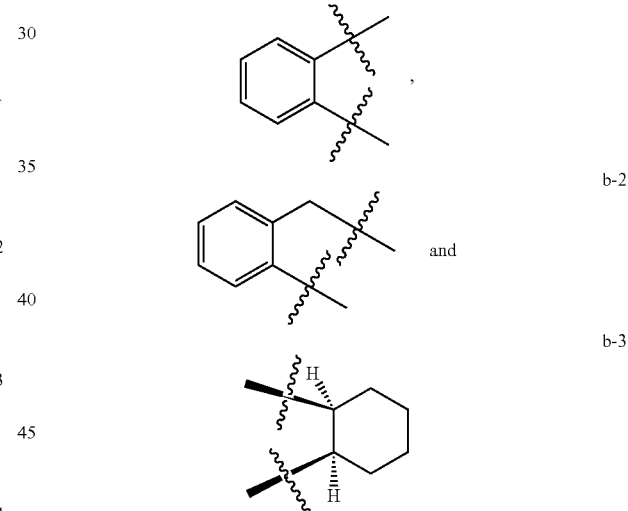

b-1 b-2 and b-3 wherein said radicals —CH$_2$CH$_2$—, b-1 and b-2 are optionally substituted with one to three substituents independently selected from the group consisting of halogen, hydroxy, C$_{1-6}$alkyl, C$_{1-6}$alkoxy, nitro, amino, cyano, trifluoromethyl and aryl; and the radical b-3 is unsubstituted;
R$^3$ and R$^4$ are each independently selected from the group consisting of hydrogen, C$_{1-6}$alkyl, aryl, and heteroaryl; provided that only one of R$^3$ or R$^4$ can be C$_{1-6}$alkyl, aryl, or heteroaryl;
R$^5$ and R$^6$ are each independently selected from the group consisting of hydrogen, C$_{1-6}$alkyl, aryl, and heteroaryl; provided that only one of R$^5$ or R$^6$ can be C$_{1-6}$alkyl, aryl, or heteroaryl;
n and r are integers from 0 to 2;
L is selected from the group consisting of O, S, N(R$^{21}$) and H$_2$, wherein R²¹ is selected from the group consisting of hydrogen, $C_{1-6}$alkyl, and aryl;

R⁷ and R⁸ are each independently selected from the group consisting of hydrogen and $C_{1-6}$alkyl; provided that only one of R⁷ or R⁸ can be $C_{1-6}$alkyl;

s is an integer from 0 to 3;

R⁹ is selected from the group consisting of hydrogen and $C_{1-6}$alkyl;

R¹⁰ and R¹¹ are each independently selected from the group consisting of hydrogen and $C_{1-6}$alkyl; provided that only one of R¹⁰ or R¹¹ can be $C_{1-6}$alkyl;

p is an integer from 0 to 3;

R¹² and R¹³ are each independently selected from the group consisting of hydrogen, $C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl ($C_{1-6}$)alkyl, aryl, and heteroaryl, wherein when R¹² and R¹³ are selected from $C_{1-6}$alkyl, R¹² and R¹³ may be optionally fused to Ar;

Ar is selected from the group consisting of phenyl, naphthyl and heteroaryl, wherein said phenyl is substituted with at least one and up to four Z substituents and said naphthyl or heteroaryl is optionally substituted with one to four Z substituents;

Z is zero to four substituents independently selected from the group consisting of halogen, $C_{1-6}$alkyl, $C_{1-6}$alkoxy, nitro, cyano, hydroxy, heteroaryl, heterocyclyl, —$(CH_2)_q$C(W)R¹⁷, —$(CH_2)_q$COOR¹⁷, —$(CH_2)_q$C(W)NR¹⁷R¹⁸, —$(CH_2)_q$NR¹⁷R¹⁸, —$(CH_2)_q$NR¹⁹C(W)R¹⁷, —$(CH_2)_q$NR¹⁹SO_2R¹⁷, —$(CH_2)_q$NR¹⁹C(W)NR¹⁷R¹⁸, —$S(O)_q$R¹⁷, —$(CH_2)_q$SO_2NR¹⁷R¹⁸, and —$(CH_2)_q$NR¹⁹CWR¹⁷;

wherein q is an integer from 0 to 2;

W is selected from the group consisting of O, S, and NR²⁰;

R¹⁷ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl); provided that when R¹⁷ is heterocyclyl and contains a N atom, the point of attachment for said heterocyclyl ring is a carbon atom;

R¹⁸, R¹⁹ and R²⁰ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl);

when R¹⁷ and R¹⁸ are $C_{1-6}$alkyl optionally substituted with hydroxy, mercapto, $C_{1-4}$alkoxy, amino or $C_{1-4}$amino and are present on the same substituent group, R¹⁷ and R¹⁸ can optionally be taken together to form a 5- to 8-membered ring;

additionally, if R¹⁷ or R¹⁸ are $C_{1-6}$alkyl optionally substituted with a hydroxy, $C_{1-4}$alkoxy, amino, or $C_{1-4}$alkylamino R¹⁷ and R¹⁸ may be optionally fused to Ar;

with the proviso that when r, s and p are 0, n is 0 or 1, L is O and R³, R⁴, R⁹, R¹² and R¹³ are all hydrogen, and Ar is phenyl with one Z, the Z substituent is not 4-OH;

and pharmaceutically acceptable enantiomers, diastereomers and salts thereof.

The present invention also concerns amino acids or derivatives (racemic and enantiomerically pure) of formula (II):

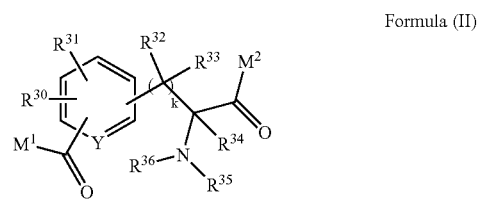

Formula (II)

wherein:

M¹ and M² are each independently selected from the group consisting of hydroxy, $C_{1-6}$alkyl, $C_{1-6}$alkoxy, amino, $C_{1-6}$alkylamino, di($C_{1-6}$)alkylamino and —NR³⁷R³⁸;

wherein R³⁷ and R³⁸ are independently selected from the group consisting of $C_{1-6}$alkyl optionally substituted with hydroxy, $C_{1-4}$alkoxy, amino, $C_{1-4}$alkylamino, mercapto, $C_{1-4}$alkylmercapto;

when R³⁷ and R³⁸ are present on the same substituent group, R³⁷ and R³⁸ can optionally be taken together to form a 5- to 8-membered ring;

Y is selected from the group consisting of CH, and one or two nitrogen atoms replacing one or two CH group(s) of the phenyl ring;

R³⁰ and R³¹ are independently selected from the group consisting of $C_{1-6}$alkyl, $C_{1-6}$alkoxy, $C_{1-6}$alkoxy optionally substituted with hydroxy and amino, and halogen;

R³² and R³³ are independently selected from the group consisting of hydrogen and $C_{1-6}$alkyl;

k is an integer from 0 to 2;

R³⁴ is selected from the group consisting of hydrogen and $C_{1-6}$alkyl; and

R³⁵ and R³⁶ are independently selected from the group consisting of hydrogen, $C_{1-6}$alkyl, —C(O)OR³⁷, —C(O)R³⁸ and phenyl;

wherein R³⁷ is selected from the group consisting of $C_{1-6}$alkyl and aryl($C_{1-6}$)alkyl; and R³⁸ is selected from the group consisting of $C_{1-6}$alkyl, aryl and heteroaryl;

and nitrogen or acid protected groups, activated esters, pharmaceutically acceptable enantiomers, diastereomers and salts thereof.

The present invention also concerns a method of treating a disorder modulated by an opioid receptor in a subject in need thereof comprising administering to the subject a compound of Formula (I).

DETAILED DESCRIPTION OF THE INVENTION

The claims of the present invention are suitable for treatment of opioid modulated disorders such as pain and gastrointestinal disorders. Compounds of the present invention are believed to provide advantages over related compounds by providing improved pharmacological profiles. Further specific embodiments of preferred compounds are provided hereinafter.

Embodiments of the present invention include those compounds wherein, preferably, X is —(CR$^{15}$R$^{16}$)$_m$—.

Embodiments of the present invention include those compounds wherein, preferably, m is an integer from 1 to 2. More preferably, m is 1.

Embodiments of the present invention include those compounds wherein, preferably, R$^{15}$ and R$^{16}$ are each hydrogen.

Embodiments of the present invention include those compounds wherein, preferably, R$^{1}$ is a-1.

Embodiments of the present invention include those compounds wherein, preferably, A-B is selected from the group consisting of N—C and O—N. More preferably, A-B is N—C.

Embodiments of the present invention include those compounds wherein, preferably, R$^{22}$ is hydrogen.

Embodiments of the present invention include those compounds wherein, preferably, R$^{23}$ is phenyl.

Embodiments of the present invention include those compounds wherein, preferably, R$^{2}$ is selected from the group consisting of —CH$_2$CH$_2$— and b-1.

Embodiments of the present invention include those compounds wherein, preferably, R$^{3}$ is hydrogen.

Embodiments of the present invention include those compounds wherein, preferably, R$^{4}$ is hydrogen.

Embodiments of the present invention include those compounds wherein, preferably, n is an integer from 0 to 1. More preferably, n is 1.

Embodiments of the present invention include those compounds wherein, preferably, r is 0.

Embodiments of the present invention include those compounds wherein, preferably, L is O.

Embodiments of the present invention include those compounds wherein, preferably, s is 0.

Embodiments of the present invention include those compounds wherein, preferably, R$^{9}$ is selected from the group consisting of hydrogen and methyl.

Embodiments of the present invention include those compounds wherein, preferably, R$^{12}$ is selected from the group consisting of hydrogen and methyl. More preferably, R$^{12}$ is hydrogen.

Embodiments of the present invention include those compounds wherein, preferably, R$^{13}$ is selected from the group consisting of hydrogen and methyl. More preferably, R$^{13}$ is hydrogen.

Embodiments of the present invention include those compounds wherein, preferably, p is 1.

Embodiments of the present invention include those compounds wherein, preferably, Ar is phenyl.

Embodiments of the present invention include those compounds wherein, preferably, Z is one to three substituents independently selected from the group consisting of hydroxy, C$_{1-6}$alkyl, and —(CH$_2$)$_q$C(W)NR$^{17}$R$^{18}$ with the proviso that when r, s and p are 0, n is 0 or 1, L is O and R$^{3}$, R$^{4}$, R$^{9}$, R$^{12}$ and R$^{13}$ are all hydrogen, and Ar is phenyl with one Z, the Z substituent is not 4-OH.

Embodiments of the present invention include those compounds wherein, preferably, q is 0.

Embodiments of the present invention include those compounds wherein, preferably, W is O.

Embodiments of the present invention include those compounds wherein, preferably, R$^{17}$ is selected from the group consisting of hydrogen, C$_{1-6}$alkyl and C$_{1-6}$alkoxy.

Embodiments of the present invention include those compounds wherein, preferably, R$^{18}$ is selected from the group consisting of hydrogen, C$_{1-6}$alkyl and C$_{1-6}$alkoxy.

Embodiments of the present invention include those compounds wherein, preferably, R$^{17}$ and R$^{18}$ are independently selected from the group consisting of hydrogen, C$_{1-6}$alkyl and C$_{1-6}$alkoxy, where when R$^{17}$ and R$^{18}$ are present on the same substituent group, R$^{17}$ and R$^{18}$ can optionally be taken together to form a 5- to 8-membered ring.

Embodiments of the present invention include the new, specific examples of compounds of Formula (II) shown below, and related standard N-protected derivatives, such as, but not limited to Boc, Fmoc, and CBZ protected compounds, and appropriate acid protected or activated esters such as, but not limited to Me, Et, and Benzyl esters and hydrosuccinimide activated ester compounds, which are all preferred key intermediates for the synthesis of agonists/antagonists for opioid receptors, integrin antagonists, and others.

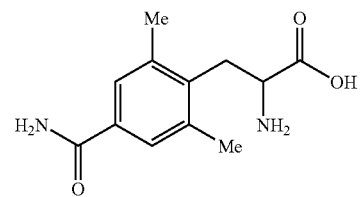

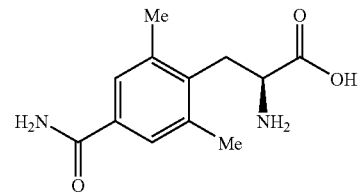

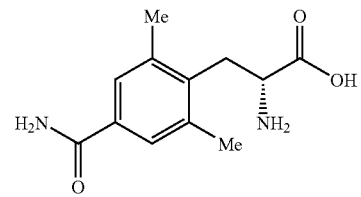

Exemplified compounds of the present invention include compounds of Formula (Ia):

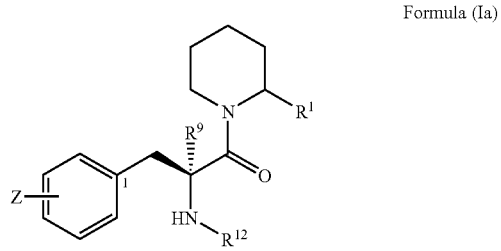

Formula (Ia)

Wherein R$^{1}$, Z, R$^{9}$ and R$^{12}$ are selected from:

| Cmpd | R¹ | Z | R⁹ | R¹² |
|---|---|---|---|---|
| 1 | 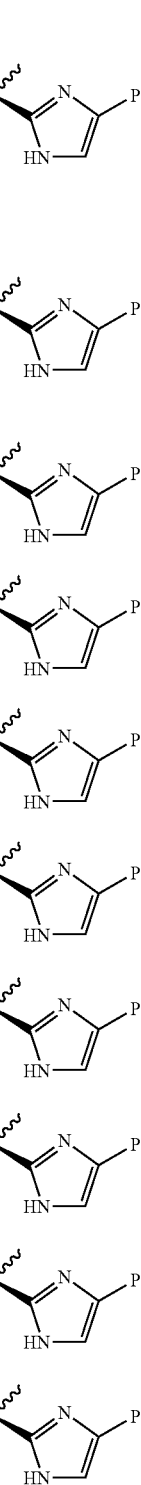 | 4-C(O)NHCH₂Me | H | H |
| 2 | 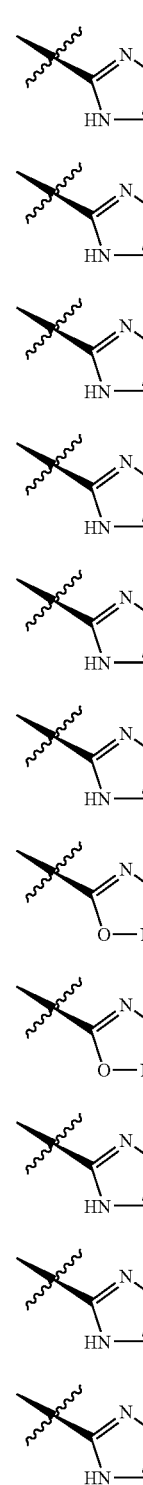 | 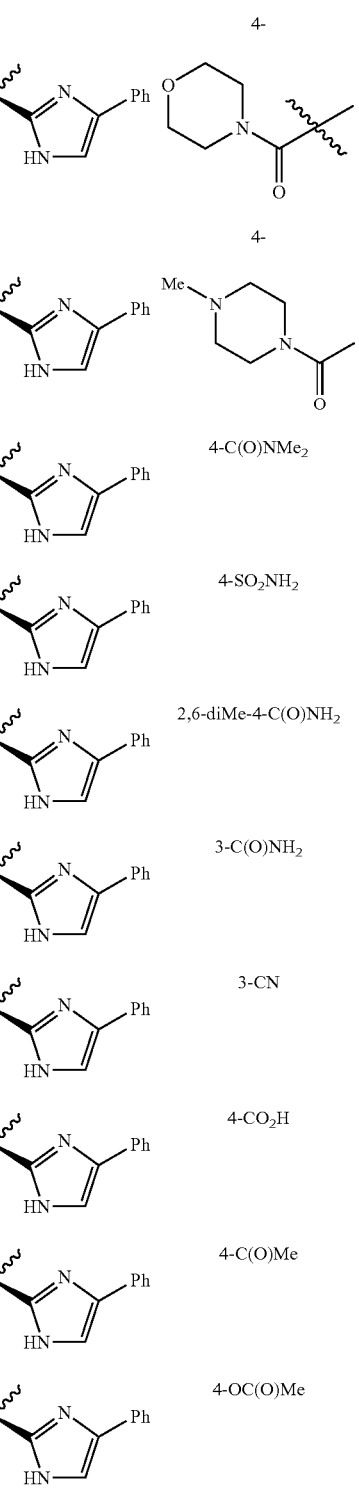 4- | H | H |
| 3 | 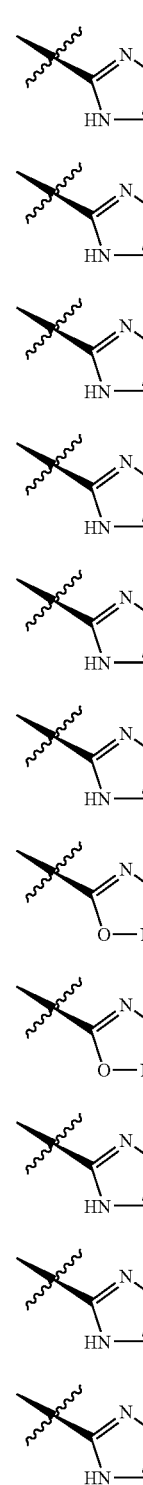 | 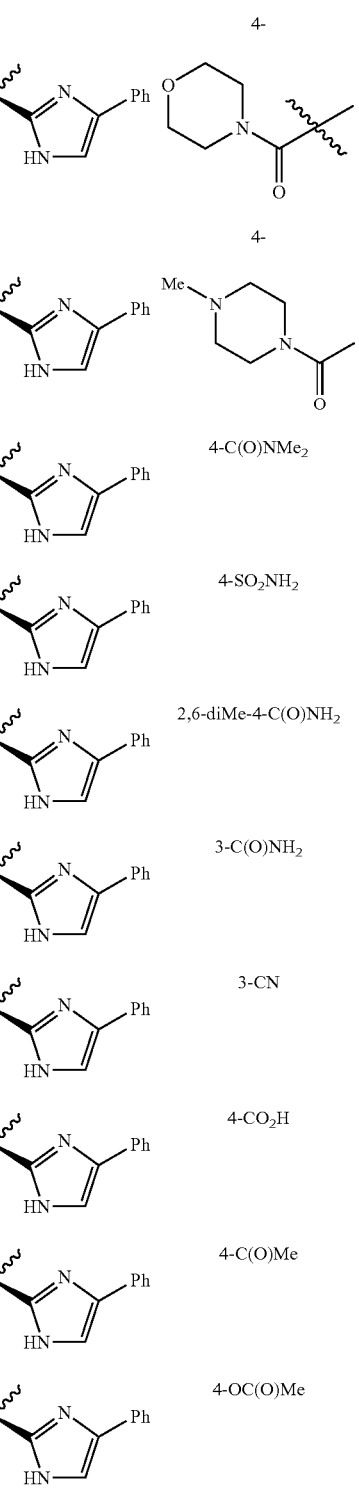 4- | H | H |
| 4 | 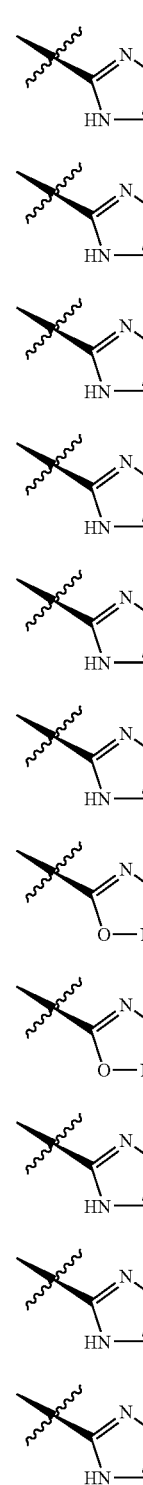 | 4-C(O)NMe₂ | H | H |
| 5 | 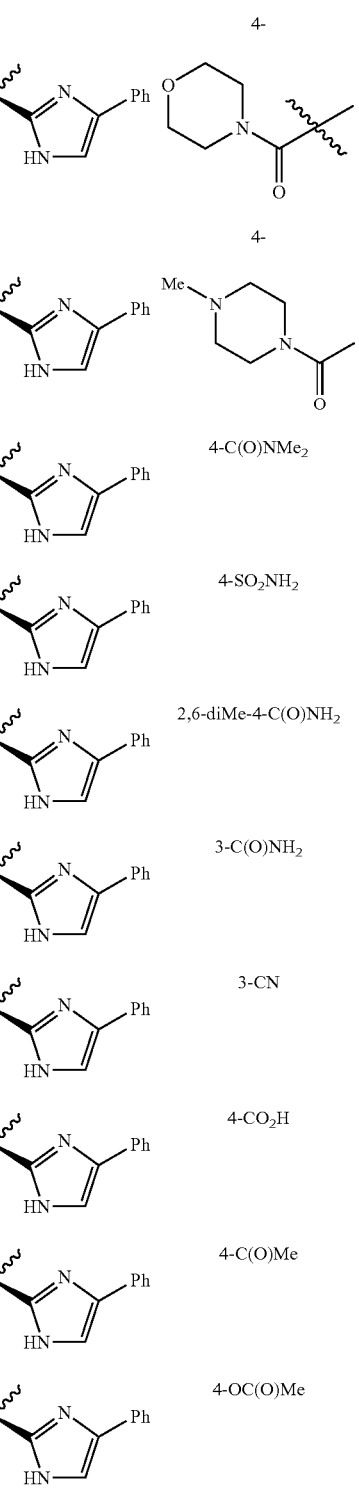 | 4-SO₂NH₂ | H | H |
| 6 | 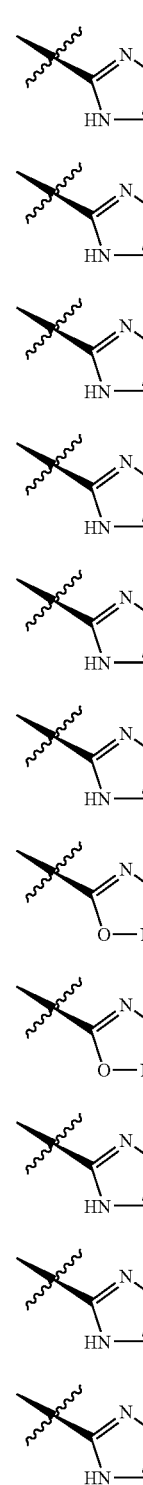 | 2,6-diMe-4-C(O)NH₂ | H | H |
| 7 | 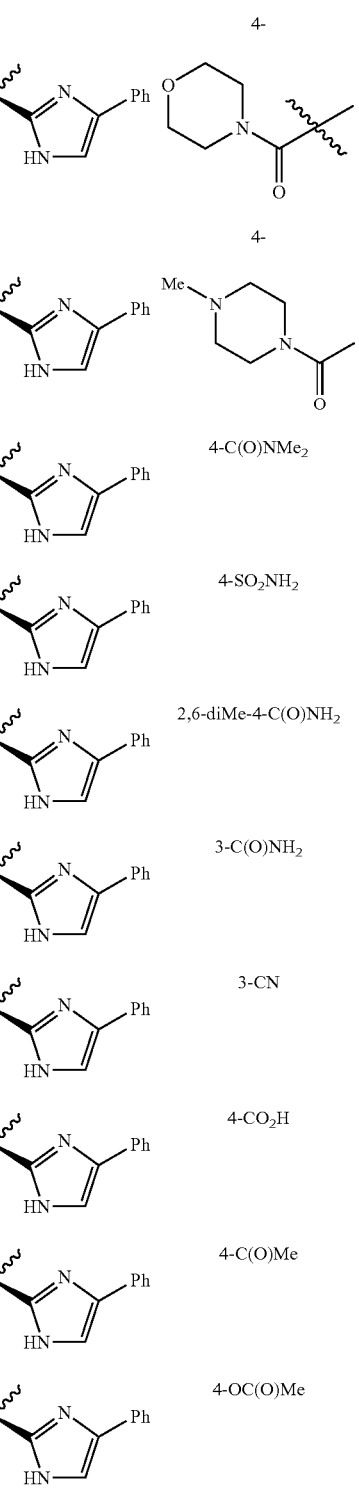 | 3-C(O)NH₂ | H | H |
| 8 | 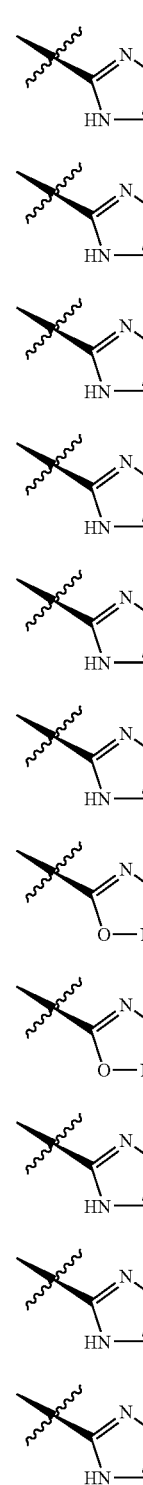 | 3-CN | H | H |
| 9 | 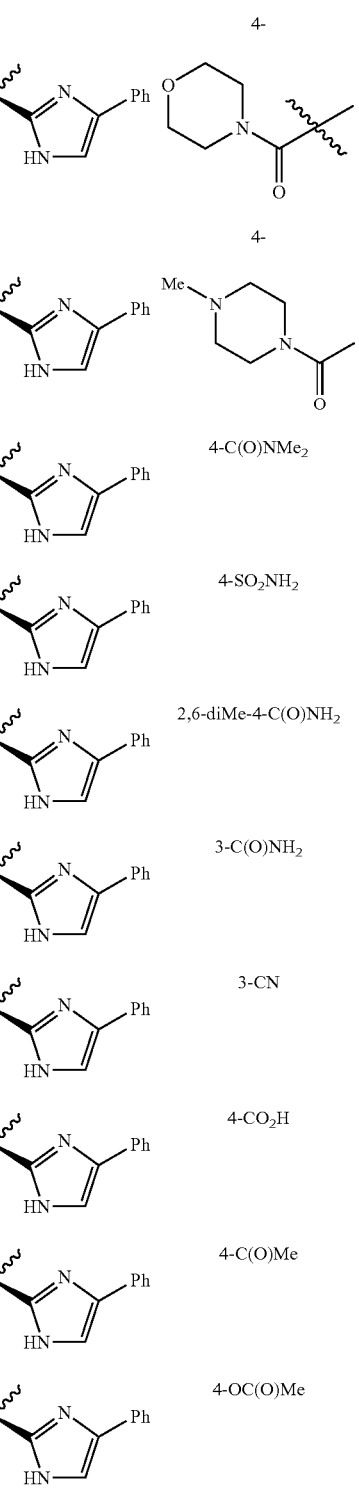 | 4-CO₂H | H | H |
| 10 | 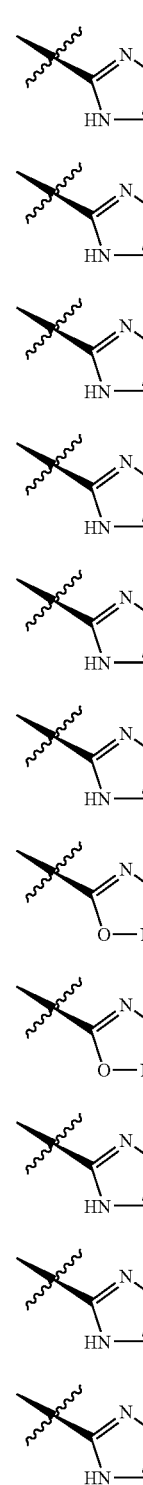 | 4-C(O)Me | H | H |
| 11 | 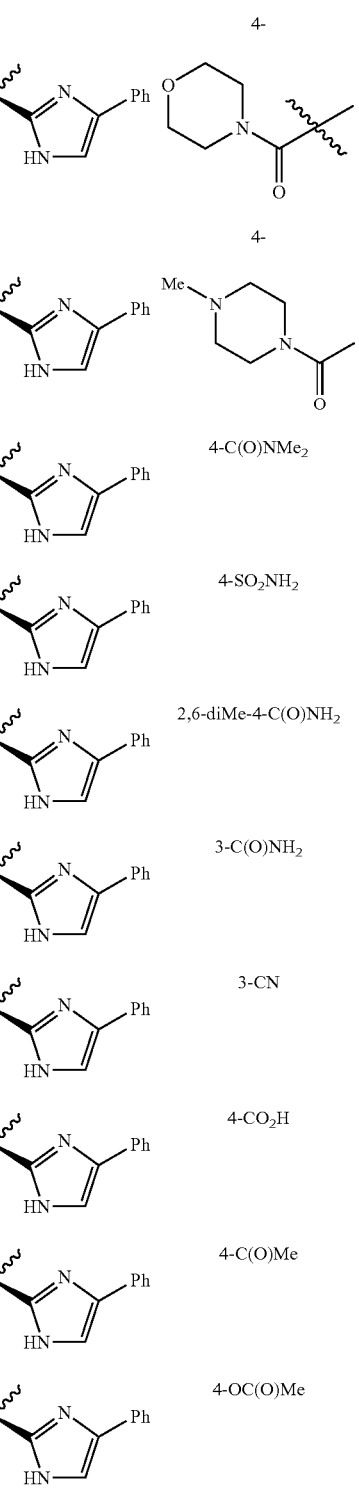 | 4-OC(O)Me | H | H |
| 12 | 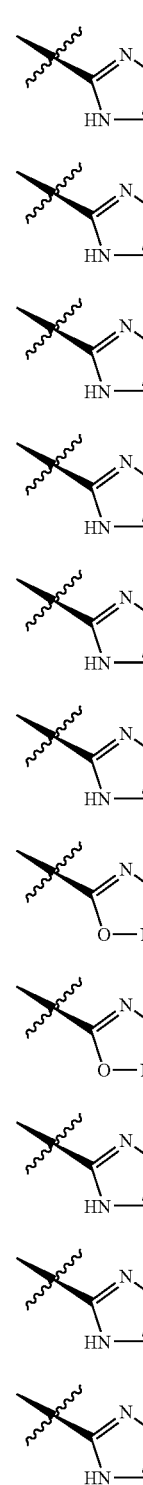 | 4-OC(O)t-Bu | H | H |
| 13 | 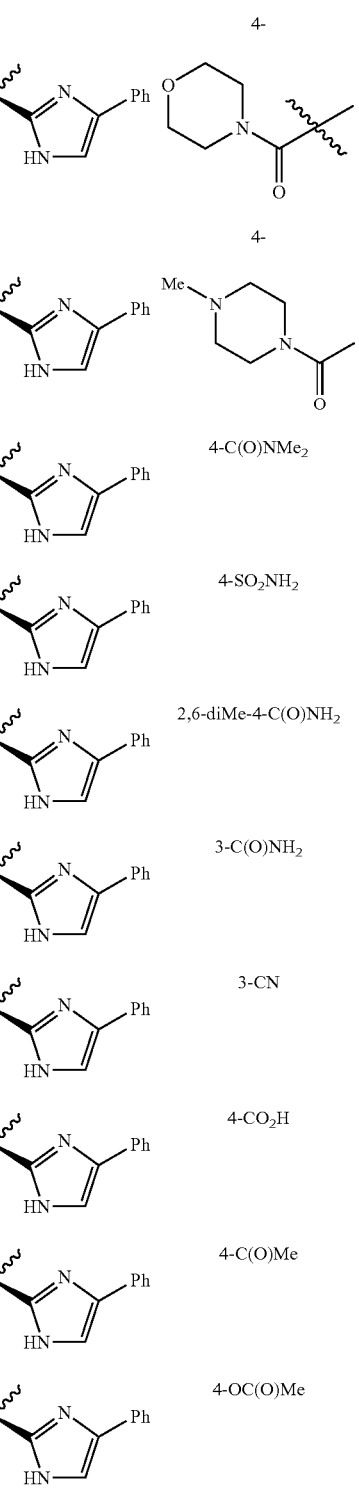 | 4-C(O)NHPh | H | H |
| 14 | 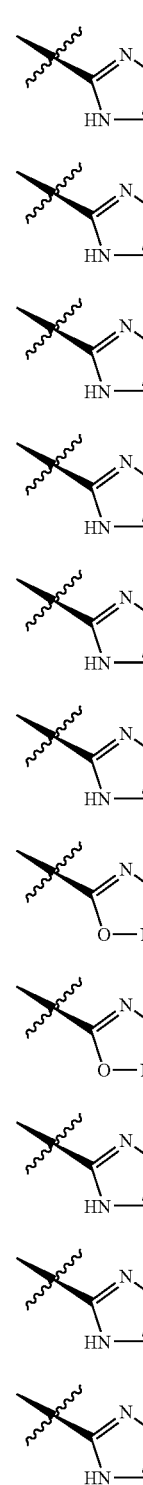 | 4-C(O)NHCH₂CH₂OH | H | H |
| 15 | 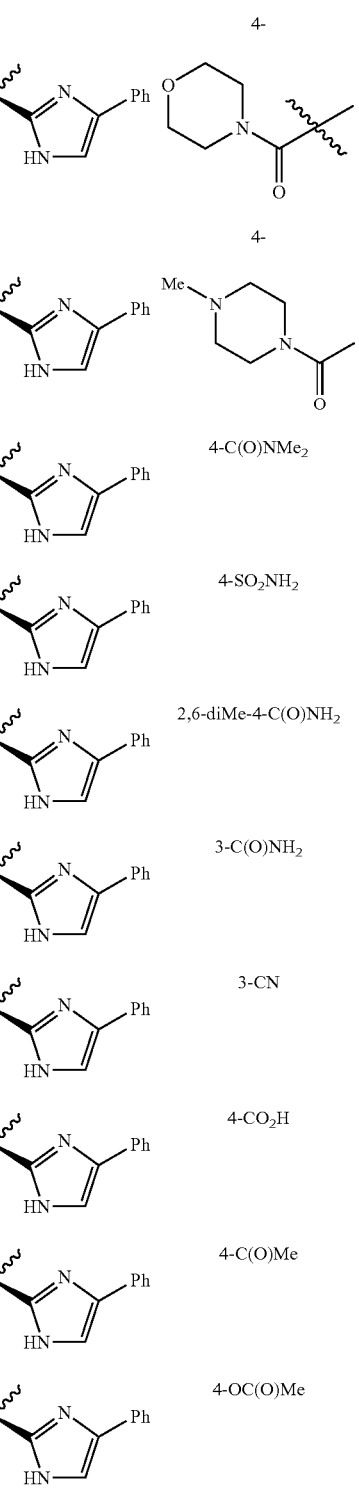 | 4-C(O)NH₂ | H | H |
| 16 | 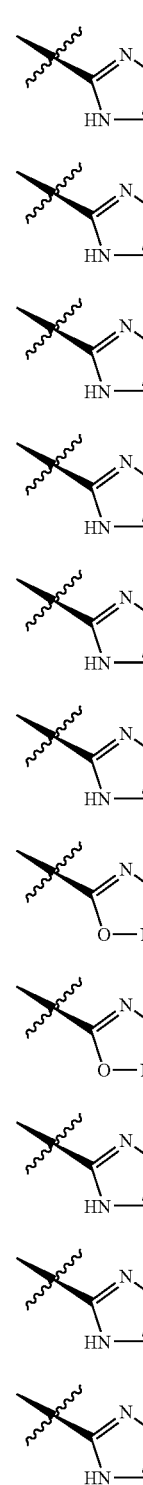 | 3-NH₂-4-OH | H | H |
| 17 | 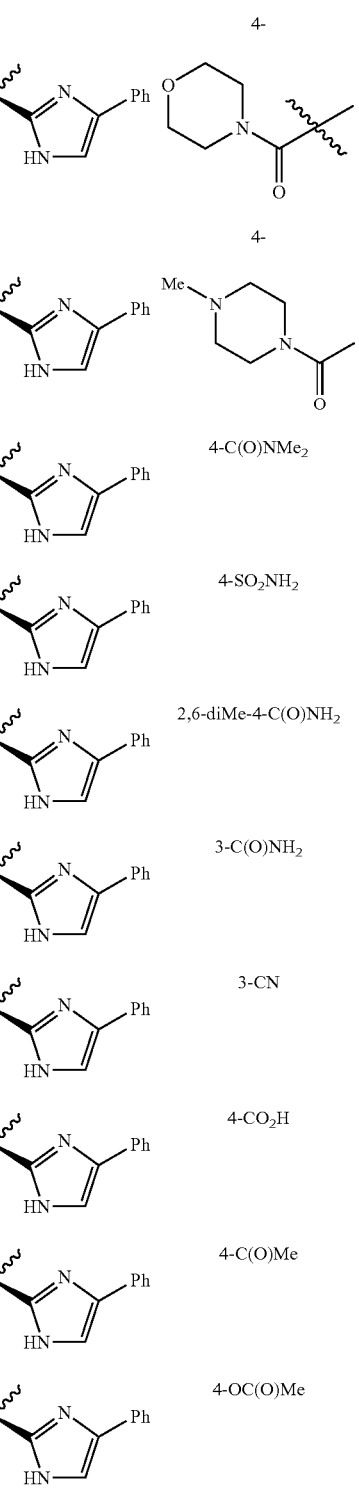 | 3-NO₂-4-OH | H | H |
| 18 | 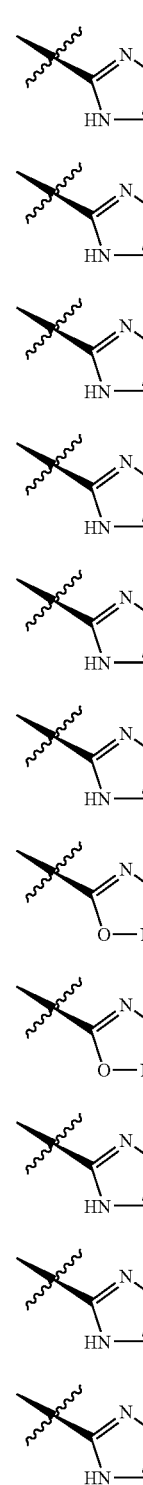 | 4-CH₂NH₂ | H | H |
| 19 | 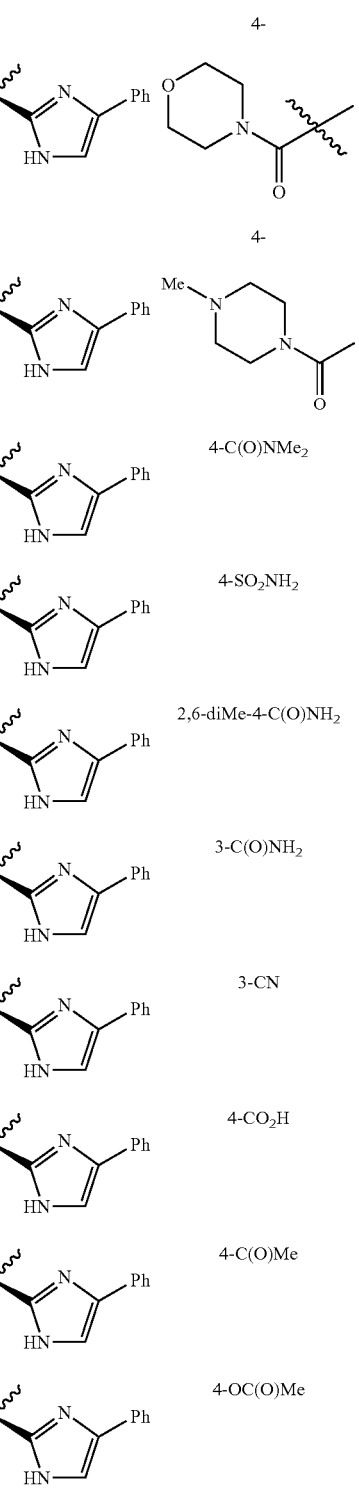 | 2,6-diMe-4-OH | H | H |
| 20 | 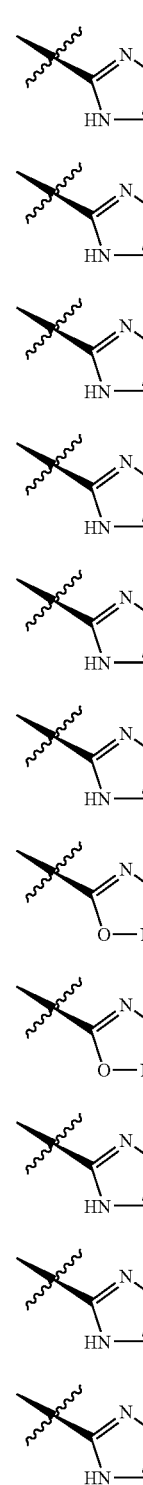 | 4-OH | H | H |
| 21 | 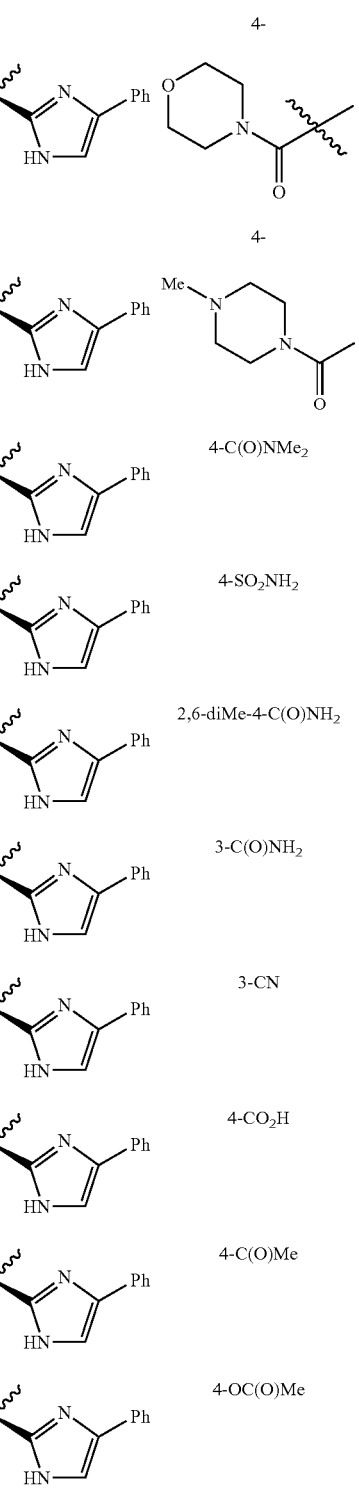 | 4-C(O)NHMe | H | H |
| 22 | 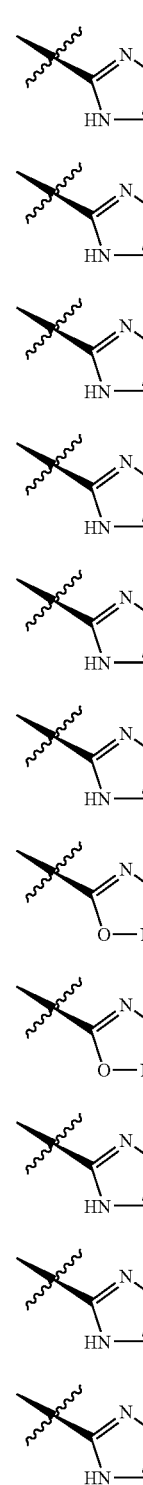 | 3-OH | H | H |
| 24 |  | 3,5-diF-4-OH | H | H |

| Cmpd | R¹ | Z | R⁹ | R¹² |
|---|---|---|---|---|
| 25 | 2-(4-Ph-imidazolyl) | 4-OH | Me | H |
| 26 | 2-(4-Ph-imidazolyl) | 4-OCH₂Ph | Me | H |
| 27 | 2-(4-Ph-imidazolyl) | 2,6-diMe-4-OMe | H | H |
| 28 | 2-(4-Ph-imidazolyl) | 2,6-diMe-4-OH | H | Me |
| 29 | 2-(4-Ph-5-Me-imidazolyl) | 2,6-diMe-4-OH | H | H |
| 30 | 2-(4-Ph-imidazolyl) | 4-NH₂ | H | H |
| 31 | 3-Ph-phenyl | 4-OH | H | H |
| 32 | 3-Ph-phenyl | 4-OH | H | H |
| 33 | 2-(4-Ph-imidazolyl) | 2,6-diMe-4-OMe | H | Me |
| 34 | 2-(4-Ph-imidazolyl) | 2,6-diMe-4-OH | H | H |
| 35 | 2-(4-Ph-imidazolyl) | 4-CN | H | H |
| 37 | 2-(4-Ph-imidazolyl) | 2,6-diMe-4-OH | H | —C(O)H |
| 158 | 2-(4-Ph-imidazolyl) | 2,6-diMe-4-OH | H | H |
| 203 | 2-(4-Ph-imidazolyl) | 2-Me-furyl | H | H |
| 204 | 2-(4-Ph-imidazolyl) | 4-(thiomorpholine-N-carbonyl) | H | H |
| 205 | 2-(4-Ph-imidazolyl) | 4-(piperidine-N-carbonyl) | H | H |
| 206 | 2-(4-Ph-imidazolyl) | 4-C(O)NHCH₂Me | H | H |
| 207 | 2-(4-Ph-imidazolyl) | 4-C(O)NH(CH₂)₂Me | H | H |
| 208 | 2-(4-Ph-imidazolyl) | 4-C(O)NH(CH₂)₂OMe | H | H |
| 209 | 2-(4-Ph-imidazolyl) | 4-C(O)NHCH(CH₃)₂ | H | H |
| 210 | 2-(4-Ph-imidazolyl) | 4-(morpholine-N-carbonyl) | H | H |
| 211 | 2-(4-Ph-imidazolyl) | 4-C(O)NHCH₂Me | H | H |
| 212 | 2-(4-Ph-imidazolyl) | 4-C(O)NHCH₃ | H | H |

-continued

| Cmpd | R¹ | Z | R⁹ | R¹² |
|---|---|---|---|---|
| 213 | 2-(4-Ph-imidazol-2-yl) | pyrrolidin-1-yl-C(O)- | H | H |

Further exemplified compounds of the present invention include compounds of Formula (Ib):

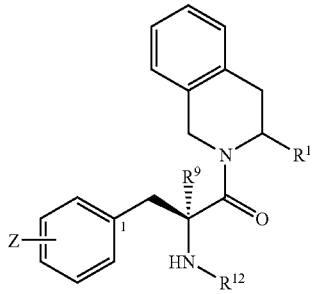

Formula (Ib)

Wherein R¹, Z, R⁹ and R¹² are selected from:

| Cmpd | R¹ | Z | R⁹ | R¹² |
|---|---|---|---|---|
| 101 | 2-(4-Ph-imidazol-2-yl) | 4-(morpholin-4-yl-C(O)-) | H | H |
| 102 | 2-(4-Ph-imidazol-2-yl) | 4-(4-Me-piperazin-1-yl-C(O)-) | H | H |
| 103 | 2-(4-Ph-imidazol-2-yl) | 4-C(O)NMe₂ | H | H |
| 104 | 2-(4-Ph-imidazol-2-yl) | 4-SO₂NH₂ | H | H |
| 105 | 2-(4-Ph-imidazol-2-yl) | 2,6-diMe-4-C(O)NH₂ | H | H |
| 106 | 2-(4-Ph-imidazol-2-yl) | 4-CO₂H | H | H |
| 109 | 2-(4-Ph-imidazol-2-yl) | 3,5-diF-4-OH | H | H |

-continued

| Cmpd | R¹ | Z | R⁹ | R¹² |
|------|----|----|----|----|
| 110 | 2-(4-Ph-imidazolyl) | 4-C(O)Me | H | H |
| 111 | 2-(4-Ph-imidazolyl) | 4-C(O)NHPh | H | H |
| 112 | 2-(4-Ph-imidazolyl) | 4-C(O)NHCH₂CH₂OH | H | H |
| 113 | 2-(4-Ph-imidazolyl) | 2,6-diMe-4-OC(O)Me | H | H |
| 114 | 2-(4-Ph-imidazolyl) | 4-NHSO₂Me | H | H |
| 115 | 2-(4-Ph-imidazolyl) | 4-C(O)NH₂ | H | H |
| 116 | 2-(4-Ph-imidazolyl) | 2,6-diMe-4-OC(O)t-Bu | H | H |
| 117 | 2-(4-Ph-imidazolyl) | 4-C(O)NHMe | H | H |
| 118 | 2-(4-Ph-5-Me-imidazolyl) | 4-C(O)NH₂ | H | H |
| 120 | 2-(4-Ph-5-Me-imidazolyl) | 4-NO₂ | H | H |
| 121 | 2-(4-Ph-imidazolyl) | 4-OH | Me | H |
| 122 | 2-(4-Ph-imidazolyl) | 4-OCH₂Ph | Me | H |

-continued

| Cmpd | R¹ | Z | R⁹ | R¹² |
|---|---|---|---|---|
| 127 | imidazole-Ph | 2,6-diMe-4-OH | H | Me |
| 128 | imidazole-Ph | 4-OC(O)t-Bu | H | Me |
| 129 | imidazole-Ph | 3-NO$_2$-4-OH | H | H |
| 130 | imidazole-Ph | 4-CH$_2$OH | H | H |
| 131 | imidazole-Ph | 2,6-diMe-4-OH | H | H |
| 132 | imidazole-Ph, Br | 2,6-diMe-4-OH | H | H |
| 133 | imidazole-Ph, Cl | 2,6-diMe-4-OH | H | H |
| 134 | imidazole-Ph | 4-OH | H | —CH$_2$Ph |
| 135 | imidazole-Ph | 4-OH | H | —CH$_2$Ph |
| 136 | imidazole-Ph | 4-OH | H | Et |
| 137 | imidazole-Ph | 4-OH | H | Et |

-continued

| Cmpd | R¹ | Z | R⁹ | R¹² |
|---|---|---|---|---|
| 138 | 2-(4-Ph-imidazolyl) | 4-OH | H | i-Pr |
| 140 | 2-(4-Ph-imidazolyl) | 4-C(O)Me | H | Me |
| 141 | 2-(4-Ph-5-Me-imidazolyl) | 4-NHC(O)Me | H | H |
| 142 | 2-(4-Ph-5-Me-imidazolyl) | 4-NH₂ | H | H |
| 143 | 2-(4-Ph-5-Me-imidazolyl) | 4-F | H | H |
| 144 | 2-(4-Ph-imidazolyl) | 4-Cl | H | H |
| 145 | 2-(4-Ph-imidazolyl) | 4-OH | H | Me |
| 146 | 2-(4-Ph-imidazolyl) | 2,6-diMe-4-OMe | H | Me |
| 147 | 2-(4-Ph-imidazolyl) | 2,6-diMe-4-OMe | H | H |
| 148 | 2-(4-Ph-5-R-imidazolyl) | 4-OH | H | H |

R = —C(O)NHCH(CH₂Ph)C(O)NH2

-continued

| Cmpd | R¹ | Z | R⁹ | R¹² |
|---|---|---|---|---|
| 149 | imidazole (2-yl, 4-Ph, 5-Me), dashed wedge | 2,6-diMe-4-OH | H | H |
| 153 | imidazole (2-yl, 4-Ph, 5-Me), dashed wedge | 4-OH | H | Me |
| 154 | imidazole (2-yl, 4-Ph, 5-Me), dashed wedge | 4-OMe | H | H |
| 155 | imidazole (2-yl, 4-Ph, 5-Me), dashed wedge | 4-OH | H | Me |
| 156 | imidazole (2-yl, 4-Ph, 5-Me), solid wedge | 4-OMe | H | H |
| 157 | imidazole (2-yl, 4-Ph, 5-Me), solid wedge | 4-OH | H | Me |
| 160 | imidazole (2-yl, 4-Ph), solid wedge | 4-CN | H | H |
| 161 | imidazole (2-yl, 4-Ph), solid wedge | 3-OH | H | H |
| 162 | imidazole (2-yl, 4-Ph), solid wedge | —C(O)NHCH₂Me | H | H |

Further exemplified compounds of the present invention include compounds of Formula (Ic):

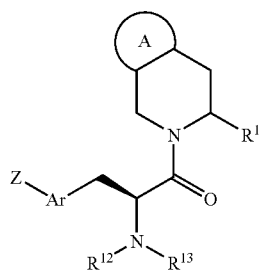

Formula (Ic)

Wherein $R^1$, Ar, Z, $R^{12}$ and $R^{13}$ are selected from:

| Cmpd | $R^1$ | Ar | A ring | Z | $R^{12}$ | $R^{13}$ |
|---|---|---|---|---|---|---|
| 201 | (imidazole with Ph, Me substituents) | 4-Pyridinyl | Ph | H | H | H |
| 202 | (imidazole with Ph, Me substituents) | Phenyl | Ph | 4-OH | Me | Me |
| 215 | (imidazole with Ph substituent) | | | 2,6-diMe-4-OH | H | H |

Exemplified compounds of the present invention include compounds of Formula (Id):

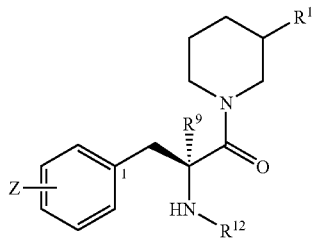

Formula (Id)

Wherein $R^1$, Z, $R^9$ and $R^{12}$ are selected from:

| Cmpd | $R^1$ | Z | $R^9$ | $R^{12}$ |
|---|---|---|---|---|
| 214 | (imidazole with Ph substituent) | 2,6-diMe-4-OH | H | H |

Exemplified compounds of the present invention include compounds of Formula (Ie):

Formula (Ie)

| Cmpd | $R^1$ | Z | $R^9$ | $R^{12}$ |
|---|---|---|---|---|
| 216 | (imidazole with Ph substituent) | 2,6-diMe-4-OH | H | H |

Further exemplified compounds of the present invention include the compounds shown below:

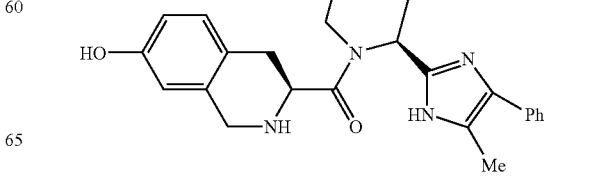

304

-continued

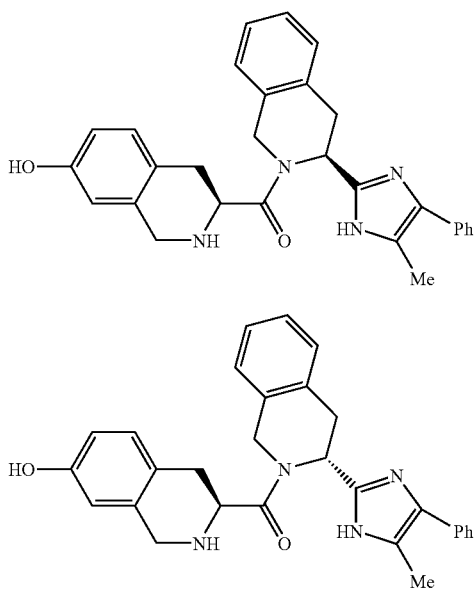

305

306

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzensulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenylC$_1$–C$_6$alkylaminocarbonylC$_1$–C$_6$alkyl" substituent refers to a group of the formula

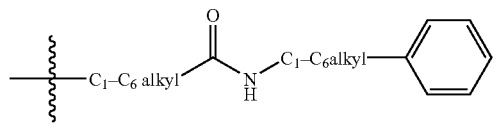

Divalent substituents drawn or named herein are read into the base structure from left to right.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, the term "alkyl" refers to a saturated straight or branched chain consisting solely of 1–8 hydrogen substituted carbon atoms or a mixture of hydrogen substituted and fluoro substituted carbon atoms wherein there may be 1–3 fluorine atoms on each carbon atom provided that the total number of fluorine atoms does not exceed 3 and the total number of carbon atoms does not exceed 8; preferably, 1–6 hydrogen substituted carbon atoms or a mixture of hydrogen substituted and fluoro substituted carbon atoms wherein there may be 1–3 fluorine atoms on each carbon atom provided that the total number of fluorine atoms does not exceed 3 and the total number of carbon atoms does not exceed 6; and, most preferably, 1–4 hydrogen substituted carbon atoms or a mixture of hydrogen substituted and fluoro substituted carbon atoms wherein there may be 1–3 fluorine atoms on each carbon atom provided that the total number of fluorine atoms does not exceed 3 and the total number of carbon atoms does not exceed 4. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl chains are optionally substituted within the alkyl chain or on a terminal carbon atom.

The term "cycloalkyl" refers to a saturated or partially unsaturated monocyclic alkyl ring consisting of 3–8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five or six members of which at least one member is a N, O or S atom and which optionally contains additional N, O or S atoms; a saturated or partially unsaturated bicyclic ring having nine or ten members of which at least one member is a N, O or S atom and which optionally contains additional N, O, or S atoms. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

The term "aryl" refers to a phenyl or naphthyl group.

The term "heteroaryl" refers to an aromatic monocyclic ring system containing five or six members of which at least one member is a N, O or S atom and which optionally contains additional N, S or O atoms; an aromatic bicyclic ring having nine or ten members of which at least one member is a N, O or S atom and which optionally contains additional N, S or O atoms. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]thienyl, quinolinyl, isoquinolinyl or quinazolinyl.

Wherein the terms "aryl" and "heteroaryl" are used either alone or as part of a substituent term (Ex. aryloxy, heteroaryloxy, etc.) the said aryl or heteroaryl may be optionally substituted with one to three substituents independently selected from the group consisting of halogen, hydroxy, cyano, $C_{1-6}$alkyl, $C_{1-6}$alkoxy, and nitro; additionally, the aryl or heteroaryl may also be optionally substituted with one phenyl group (which may optionally be substituted with one to three substituents independently selected from the group consisting of halogen, hydroxy, cyano, $C_{1-6}$alkyl, $C_{1-6}$alkoxy, and nitro), where the substituents on the aryl or heteroaryl group are not otherwise specified.

Whenever the term "alkyl", "aryl" or "heteroaryl" or either of their prefix roots appear in a name of a substituent (e.g., heteroaryl($C_{1-6}$)alkyl) it shall be interpreted as including those limitations given above for "alkyl", "aryl" and "heteroaryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "halogen" shall include iodine, bromine, chlorine and fluorine.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The novel compounds of the present invention are useful opioid receptor modulators. In particular, certain compounds are opioid receptor agonists useful in the treatment or amelioration of conditions such as pain and gastrointestinal disorders. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic pain conditions, diabetic peripheral neuropathy, post-herpetic neuralgia, trigeminal neuralgia, post-stroke pain syndromes or cluster or migraine headaches. Examples of gastrointestinal disorders intended to be within the scope of this invention include, but are not limited to, diarrheic syndromes, motility disorders such as post-operative ileus and consitipation, and visceral pain. Also, certain compounds of the present invention are opioid receptor agonists useful in the treatment or amelioration of conditions such as pain and gastrointestinal disorders.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating pain or gastrointestinal disorders described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

The present invention includes a method for treating a disorder modulated by an opioid receptor. An embodiment of the present invention is a method for treating pain or gastrointestinal disorders or any other disorder modulated by the opioid receptor.

The present invention therefore provides a method for the use of the instant compounds as opioid receptor modulators comprising administering to a subject any of the compounds as defined herein in a therapeutically effective amount. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

The dosage of the drug in the patient can be monitored by conventional means known in the art such as monitoring drug levels in the patient's blood.

Compounds of this invention may be administered in any of the foregoing compositions and dosage regimens or by means of those compositions and dosage regimens established in the art whenever use of the compounds of the invention as opioid receptor modulators is required for a subject in need thereof.

The terms used in describing the invention are commonly used and known to those skilled in the art. As used herein, the following abbreviations have the indicated meanings:

| | |
|---|---|
| DMF = | N,N-Dimethylformamide |
| CBZ = | Benzyloxycarbonyl |
| BOC = | t-Butyloxycarbonyl |
| TFA = | Trifluoroacetic acid |
| TMSI = | Trimethylsilyl iodide |
| EDCI = | 1-(3-Dimethylaminopropyl)-3-ethylcarbodiimide hydrochloride |
| HOBT = | 1-Hydroxybenzotriazole |
| NMM = | N-Methylmorpholine |
| DCM = | Dichloromethane |
| DPPF = | 1,1'-bis(diphenylphosphino)ferrocene |

-continued

| | |
|---|---|
| PyBOP = | Benzotriazol-1-yl-oxy-tris-pyrrolidinophosphonium hexafluorophosphate |
| DIPEA = | Diisopropylethylamine |

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme A

Certain heterocyclic intermediates of the present invention may be prepared according to the process outlined in Scheme A below.

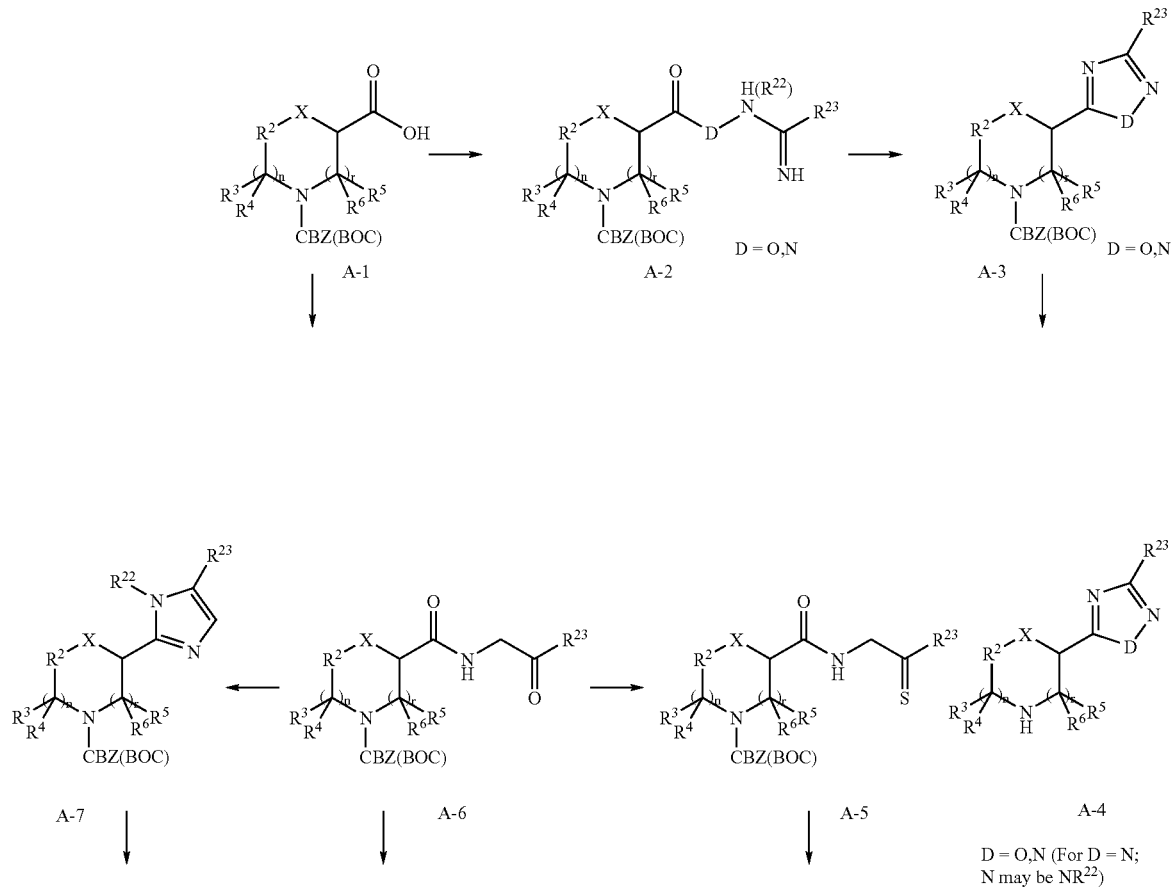

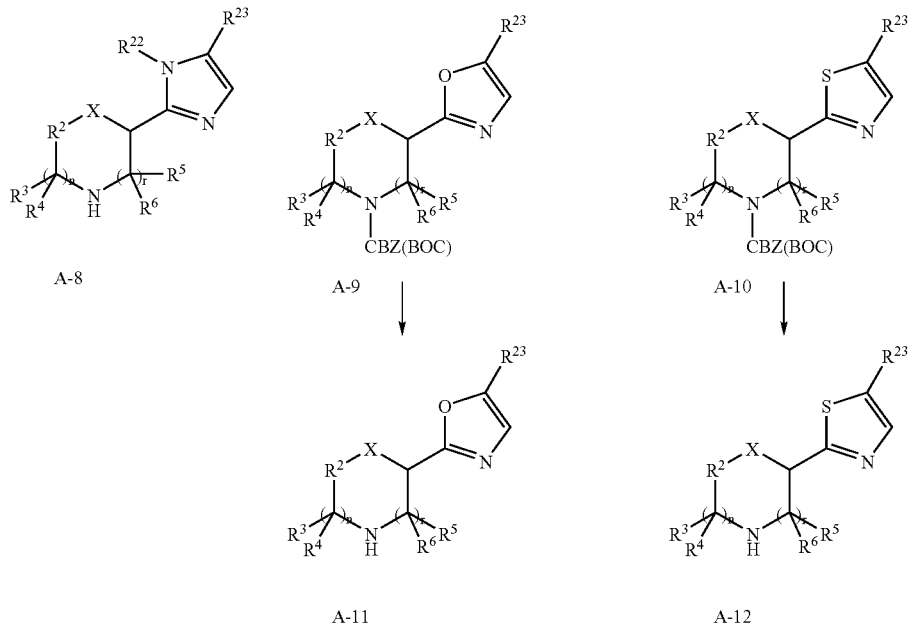

A-8    A-9    A-10

A-11    A-12

More specifically, a carboxylic acid of the formula A-1, available either commercially, or prepared by reported protocols in the scientific literature was coupled to an amine of formula H-D-N($R^{22}$)—C(=NH)—$R^{23}$, available either commercially, or prepared by protocols reported in the scientific literature, wherein D is selected from the group consisting of O and N, using standard carbodiimide coupling conditions to provide a compound of formula A-2.

A compound of formula A-2 was then cyclized to a compound of formula A-3 in the presence of a base such as pyridine upon heating either neat, as in when D is O, or in a suitable solvent such as xylene, when D is N.

The protecting group in a compound of formula A-3 was then removed using conditions known to those skilled in the art that are appropriate for the particular protecting group used. For example, if a BOC protecting group was used, it was removed upon treatment with TFA, whereas when a CBZ protecting group was used it was removed upon treatment with TMSI.

Alternatively, a compound of formula A-1 was coupled with an amine of formula $NH_2CH_2C(O)R^{23}$ using the same standard carbodiimide coupling conditions as described earlier which afforded a compound of formula A-6.

A compound of formula A-6, when heated in the presence of ammonium acetate in a suitable solvent such as xylene, cyclized to afford an imidazolyl compound of formula A-7, which can be deprotected as described above, or via hydrogenolysis with Pd and $H_2$ as an alternative for the CBZ protecting group, and afford compounds of formula A-8.

Alternatively, oxazolyl compounds of formula A-9 may be prepared by treatment of an intermediate of formula A-6 with a reagent such as $POCl_3$. Deprotection as described previously yields compounds of formula A-11.

Finally, intermediates of formula A-6 may be converted to the corresponding thioketones of formula A-5 by treatment with Lawesson's reagent. The thioketones of formula A-5 may then be cyclized upon heating in acetic acid which provides thiazole compounds of formula A-10. Deprotection as described previously yields compounds of formula A-12.

Scheme B

Certain heterocyclic intermediates of the present invention may be prepared according to the process outlined in Scheme B below.

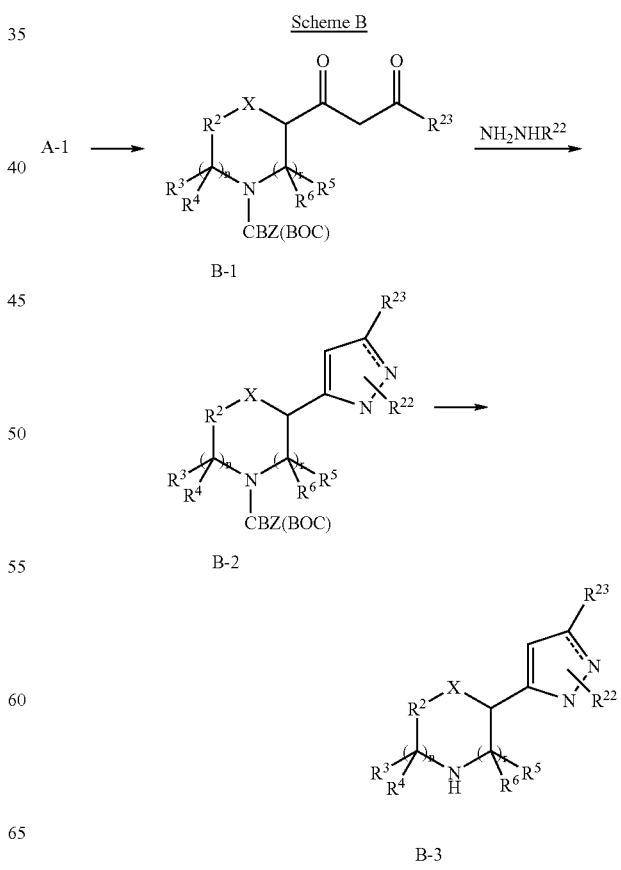

More specifically, pyrazolyl intermediates of formula B-3 may be prepared by first transforming a compound of formula A-1 into a β-diketone of formula B-1. This transformation may be accomplished via a series of reactions as shown for amino acid type substrates in *Tetrahedron* 1992, 48, 8007–8022.

The β-diketone of formula B-1 can then be cyclized in an appropriate acid such as acetic acid while being heated which provides the pyrazolyl intermediates of formula B-2.

Deprotection as previously indicated gives rise to the target intermediates of formula B-3.

Scheme C

Certain heterocyclic intermediates of the present invention may be prepared according to the process outlined in Scheme C below.

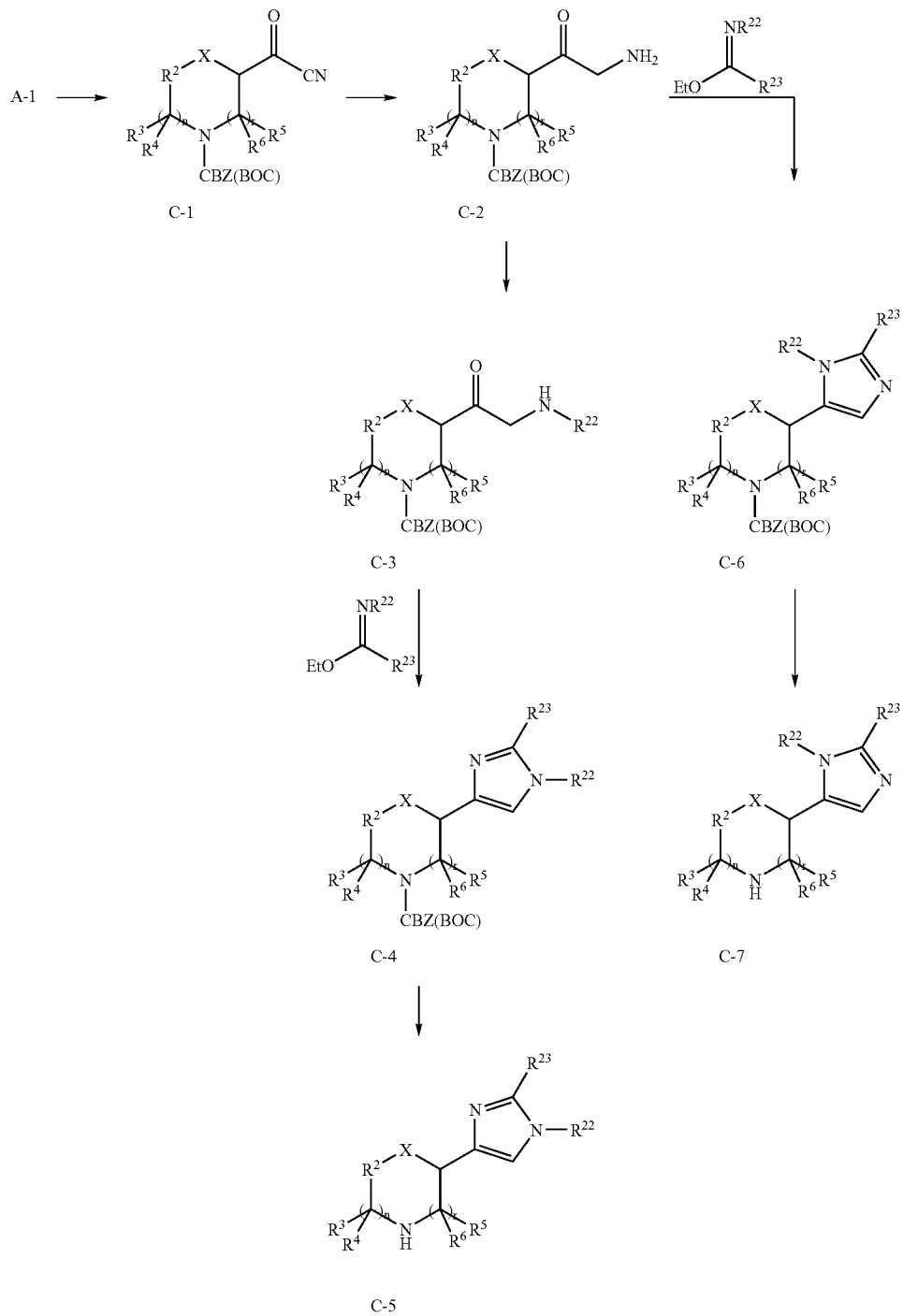

More specifically, imidazolyl intermediates of formula C-5 and C-7 may be prepared by first conversion of the carboxylic acid of formula A-1 to an acyl nitrile of formula C-1 by reacting the acid with a reagent such as $(EtO)_2P(O)CN$ in the presence of an amine such as $Et_3N$.

The acyl nitrile is then reduced to an amine of formula C-2 by subjecting it to hydrogenation conditions in the presence of an appropriate palladium catalyst, also in the presence of an acid such as AcOH.

The primary amine of formula C-2 is then reductively alkylated using standard conditions such as treatment with an aldehyde of formula RCHO followed by treatment with a reducing agent such as $NaB(OAc)_3H$ which affords compounds of formula C-3.

The compound of formula C-3 is then cyclized to an imidazolyl compound of formula C-4 by reaction with an imidate compound of formula $EtOC(NH)R^{23}$. Deprotection as indicated in Scheme A provides compounds of formula C-5.

Alternatively, compounds of formula C-2 may be cyclized with an imidate compound of formula $EtOC(NR^{22})R^{23}$ which provides compounds of formula C-6. Deprotection as indicated in Scheme A provides compounds of formula C-7.

Scheme D

Certain heterocyclic intermediates of the present invention may be prepared according to the process outlined in Scheme D below.

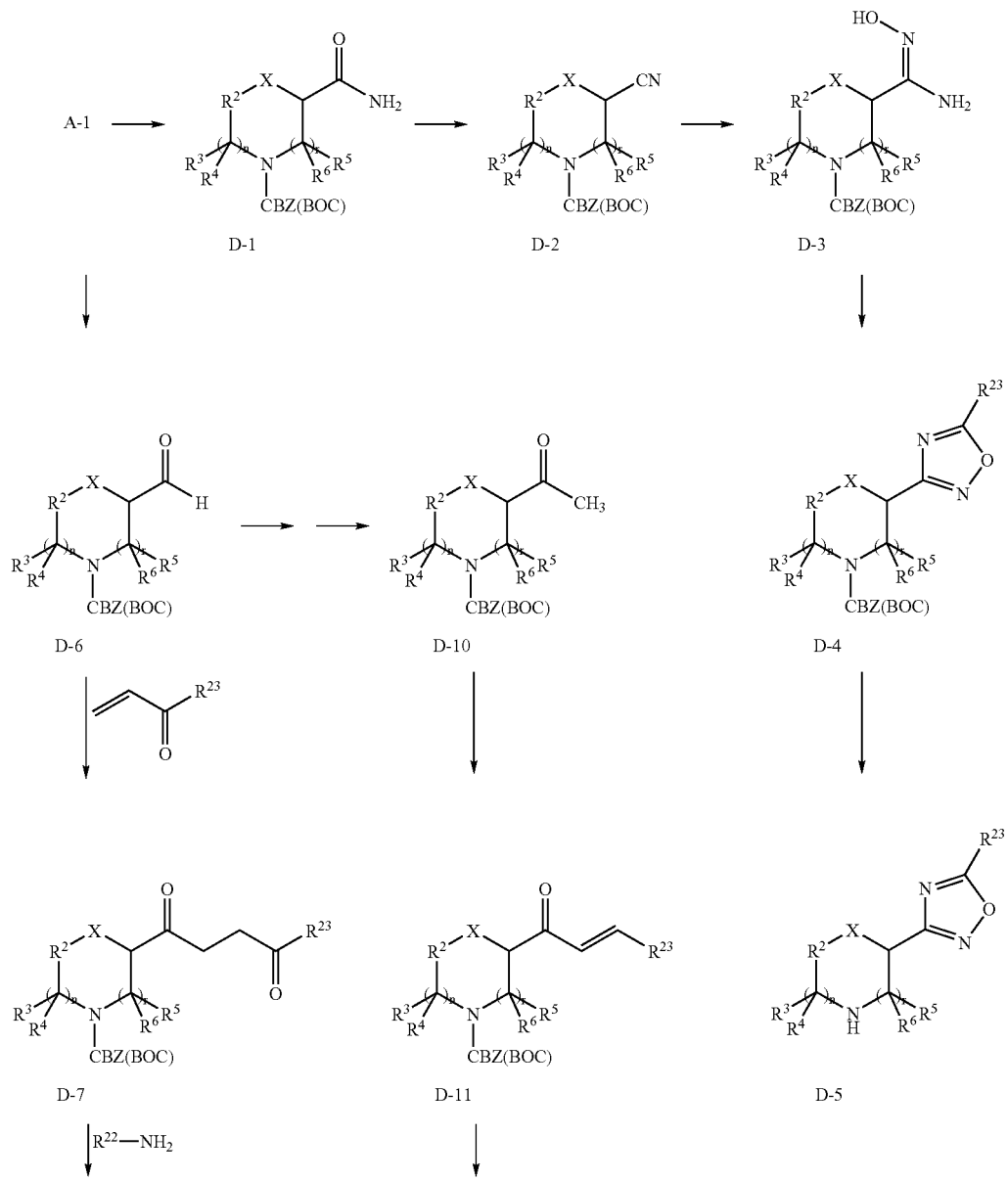

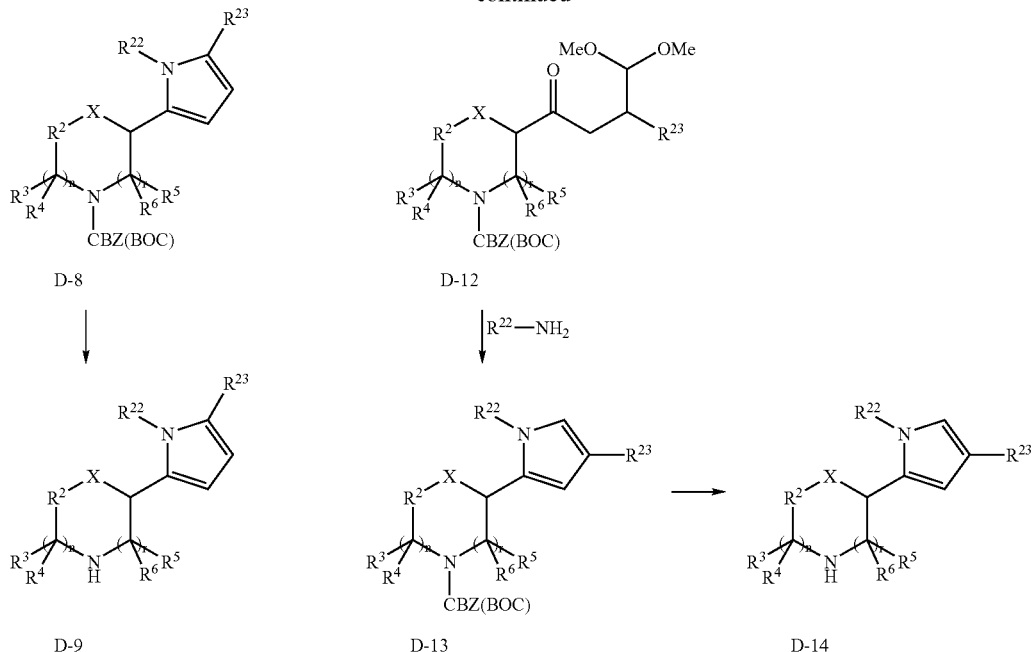

More specifically, certain oxadiazole intermediates of formula D-5 may be prepared by first preparation of primary amido compounds of formula D-1 by coupling of carboxylic acid compounds of formula A-1 with ammonia using a carbodiimide coupling reagent such as EDC.

The compound of formula D-1 is then treated with a reagent of formula $Cl_3C(O)Cl$ in the presence of an amine such as $Et_3N$ to afford a nitrile of formula D-2.

The nitrile of formula D-2 is then converted to a compound of formula D-3 by reaction with a reagent such as hydroxyl amine.

The compound of formula D-3 is then cyclized to an oxadiazole of formula D-4 in a stepwise fashion by first reaction with an acid chloride of formula $R^{23}C(O)Cl$ followed by heating in a base such as pyridine and the like. Deprotection as indicated in Scheme A provides compounds of formula D-5.

Alternatively, pyrrolyl intermediates of formula D-8 may be prepared by reduction of a compound of formula A-1 to an aldehyde of formula D-6. This transformation may be effected in a stepwise manner by treating the acid with N-methylmethoxylamine in the presence of a coupling reagent such as EDC, also in the presence of a coupling additive such as HOBT followed by reduction of the resulting intermediate with a reducing reagent such as LAH.

The compound of formula D-6 then is transformed into a diketo compound of D-7 by treatment of the aldehyde with an unsaturated ketone of formula $CH{=}CH{-}C(O)R^{23}$ in the presence of a catalyst.

The diketo compound of formula D-7 is then cyclized with an amine of formula $R^{22}{-}NH_2$ by heating in an acid such as AcOH to afford the pyrrolyl compound of formula D-8. Deprotection as indicated in Scheme A provides compounds of formula D-9.

Another type of pyrrolyl intermediate, a compound of formula D-14, may be prepared by reacting a compound of formula D-6 with a Grignard reagent followed by oxidation of the resulting alcohol intermediate which provides a compound of formula D-10.

The methyl ketone of formula D-10 then undergoes an Aldol condensation with an aldehyde of formula $R^{23}C(O)H$ followed by elimination of water to provide compounds of formula D-11.

The compound of formula D-11 then undergoes a three step transformation into a compound of formula D-12. First, the compound of formula D-11 undergoes a Michael reaction with the anion of a reagent such as nitromethane in the presence of a base. The resulting intermediate is then reacted with a base and subsequently quenched with an alcoholic solvent such as methanol, ethanol and the like in the presence of an acid which provides the compound of formula D-12.

The compound of formula D-12 is then cyclized upon heating in an acid such as AcOH in the presence of an amine of the formula $R^{22}{-}NH_2$ which affords a compound of formula D-13. Deprotection as indicated in Scheme A provides compounds of formula D-14.

All of the chemistry illustrated in Scheme D which affords the pyrrolyl intermediates D-8 and D-14 is described more fully in the literature (*J. Med. Chem.* 2000, 43, 409–419).

Scheme E

Certain heterocyclic intermediates of the present invention may be prepared according to the process outlined in Scheme E below.

Scheme E

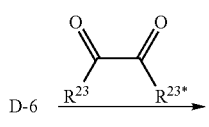

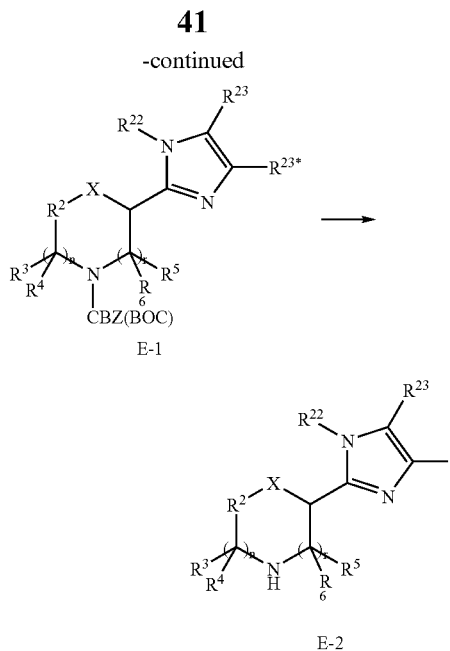

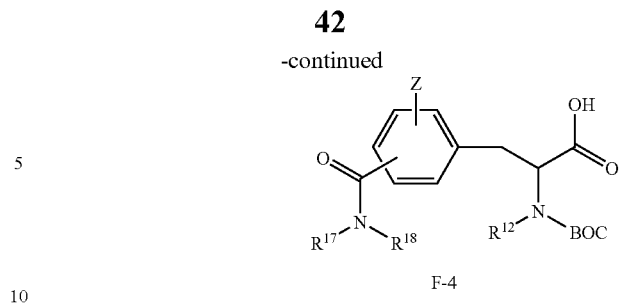

More specifically, imidazolyl intermediates of formula E-2 may be prepared by reaction of a compound of formula D-6 with a diketo compound of formula $R^{23}C(O)C(O)R^{23}$, wherein the $R^{23}$ substituents may be the same or may be different, in the presence of a reagent such as ammonium acetate, also in the presence of an acid such as AcOH while being heated which provides a compound of formula E-1. Deprotection as indicated in Scheme A provides compounds of formula E-2.

Scheme F

Certain carboxylic acid intermediates of the present invention may be prepared according to the process outlined in Scheme F below.

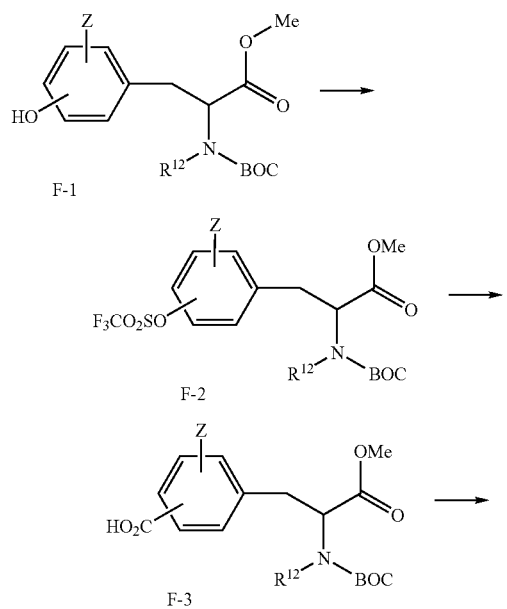

More specifically, a methyl ester of formula F-1 may be converted to it's corresponding triflate upon treatment with a reagent of formula $(CF_3SO_2)_2NC_6H_5$ in the presence of a base such as $Et_3N$ which provides a compound of formula F-2.

The triflate of formula F-2 is then transformed into a carboxylic acid of formula F-3 upon treatment with carbon monoxide gas in the presence of a palladium catalyst such as $Pd(OAc)_2$, also in the presence of a base such as potassium carbonate, also in the presence of a reagent such as DPPF, in a solvent such as DMF.

The acid of formula F-3 is then coupled to an amine of formula $HNR^{17}R^{18}$ under standard peptide coupling conditions using a coupling reagent such as PyBOP in the presence of a coupling additive such as HOBT followed by subsequent hydrolysis of the methyl ester with a base such as LiOH in an aqueous solvent such as aqueous THF and the like afforded the target intermediate, a compound of formula F-4.

The compound of formula F-4 may be used as is in subsequent schemes or may be deprotected using standard conditions known to those skilled in the art and used in subsequent schemes.

Scheme G

Certain carboxylic acid intermediates of the present invention may be prepared according to the process outlined in Scheme G below.

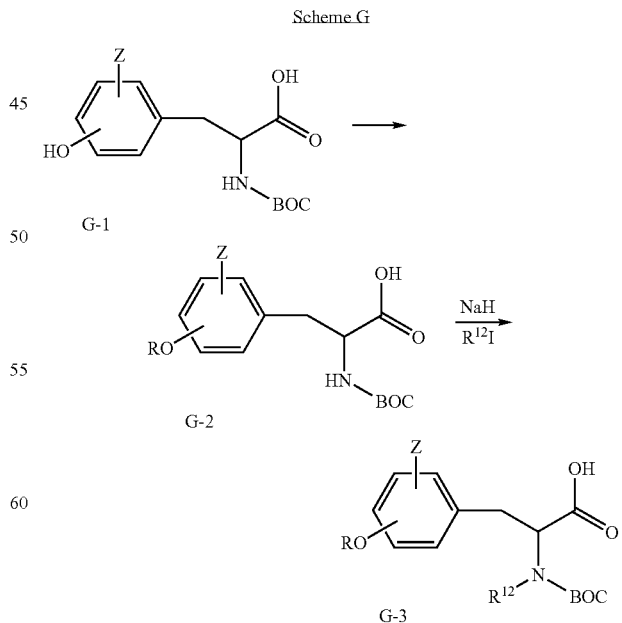

A carboxylic acid compound of formula G-1 is reacted with an electrophilic reagent such as an alkyl iodide or benzyl bromide and the like in the presence of a base such as NaH to afford the substituted oxy compound of formula G-2.

The compound of formula G-2 is then further reacted with an electrophilic reagent such as a compound of the formula $R^{12}I$ in the presence of a base such as NaH which affords the intermediate of formula G-3.

The compound of formula G3 may be used as is in subsequent schemes or may be deprotected using standard conditions known to those skilled in the art and used in subsequent schemes.

Scheme H

Certain target compounds of the present invention may be prepared according to the process outlined in Scheme H below.

More specifically, certain instant compounds of the present invention may be prepared by coupling of an intermediate of formula H-1, the synthesis of which was described in previous schemes for various $R^1$ substituents, with a carboxylic acid of formula H-2, under standard peptide coupling conditions such as in the presence of a coupling reagent such as EDC or PyBop, also in the presence of a coupling additive such as HOBT which provides a compound of formula H-3.

The compound of formula H-3 may be treated with Lawesson's reagent which provides a target compound of formula H-4 and may be subsequently reacted with an amine of formula $NH_2R^{21}$ to additionally provide a target compound of formula H-6.

Alternatively, a compound of formula H-3 may be reduced with a reducing agent such as borane to provide a target compound of formula H-5.

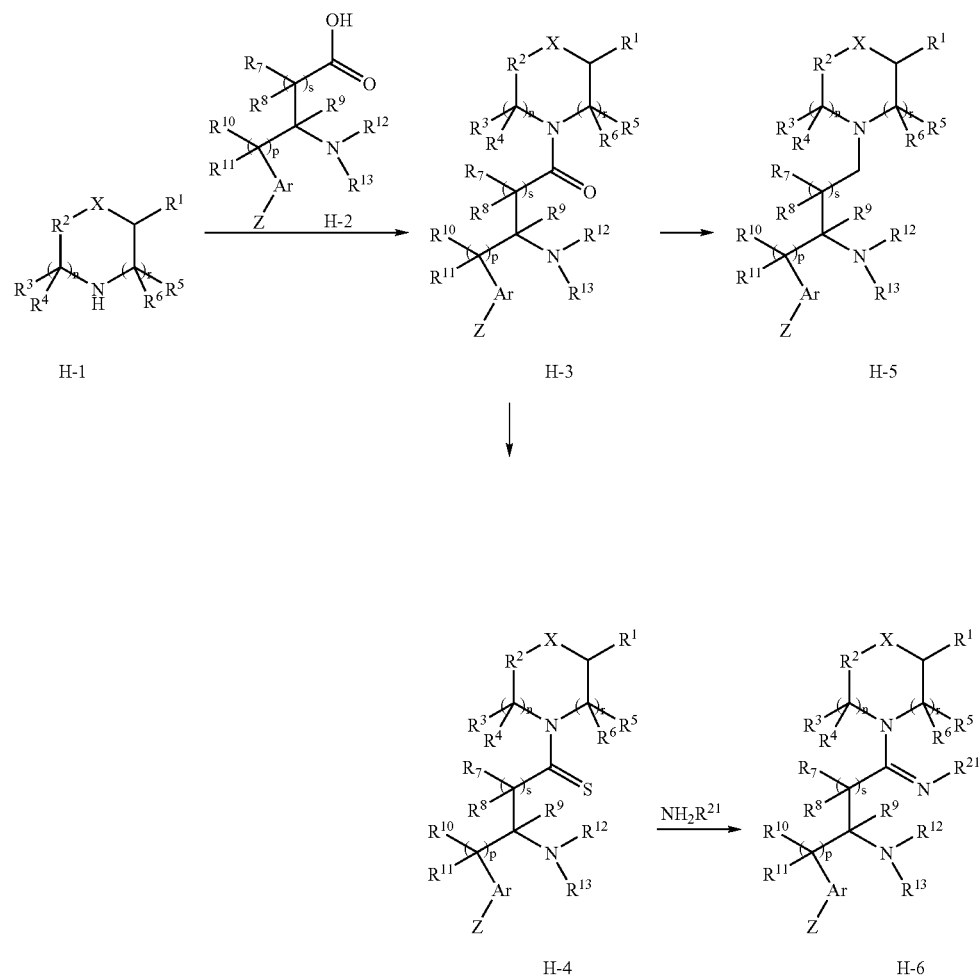

Scheme I

Certain target compounds of the present invention may be prepared according to the process outlined in Scheme I below.

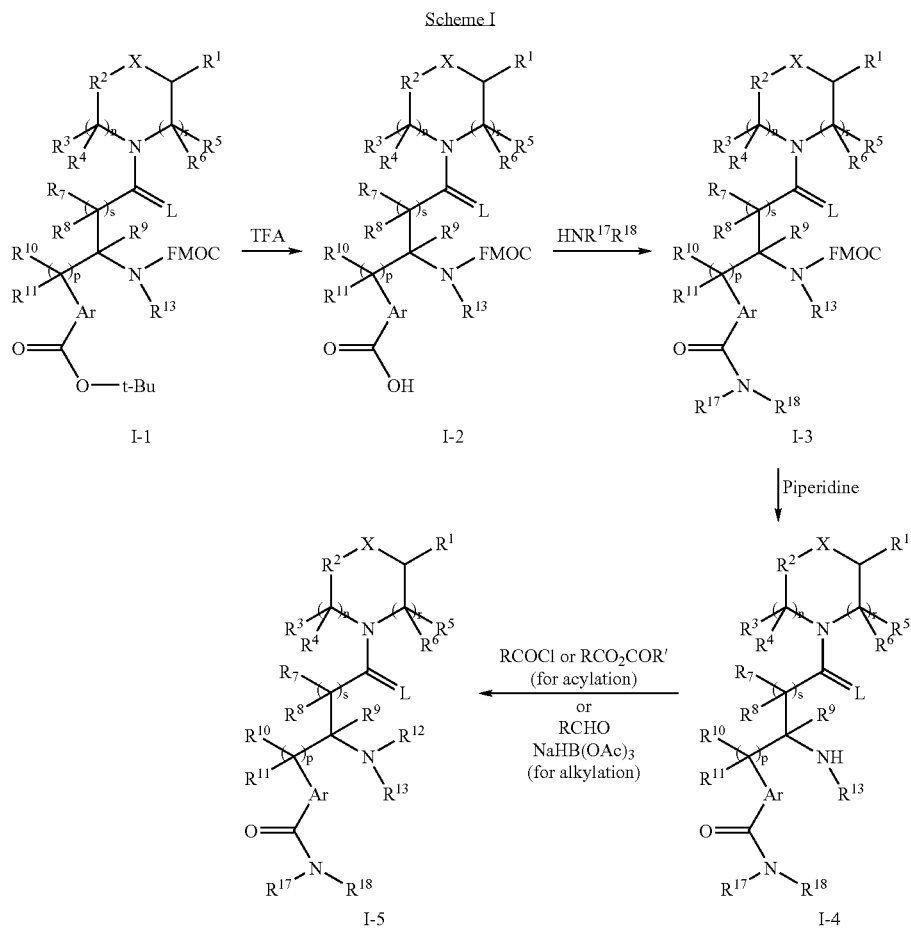

More specifically, a compound of formula I-1 may be deprotected upon treatment with an acid such as TFA, HCl and the like to afford a compound of formula I-2.

A compound of formula I-2 may be further coupled with an amine under standard peptide coupling conditions as described previously to provide a compound of formula I-3.

Deprotection of a compound of formula I-3 may be affected by treating the compound with a base such as piperidine, which yields a compound of formula I-4.

The compound of formula I-4 may be further acylated with an appropriate reagent such as an acid chloride of formula RC(O)Cl or an anhydride of formula $RCO_2C(O)R'$ which provides a compound of formula I-5 wherein $R^{12}$ is an acyl group. Alternatively, a compound of formula I-4 may be reductively alkylated with an aldehyde of formula RCHO in the presence of a reducing agent such as $NaB(OAc)_3H$ which affords a compound of formula I-5 wherein $R^{12}$ is an alkyl group.

Scheme J

Certain target compounds of the present invention may be prepared according to the process outlined in Scheme J below.

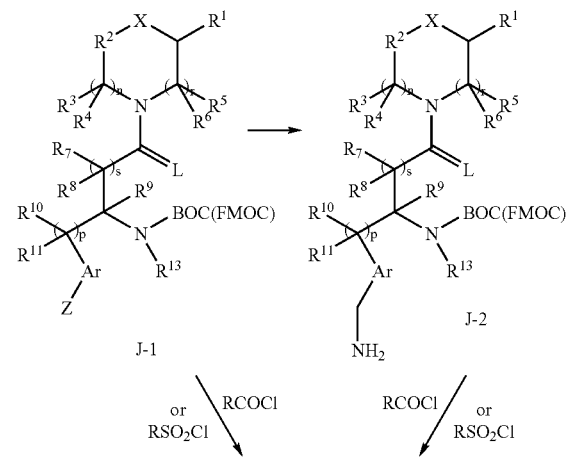

-continued

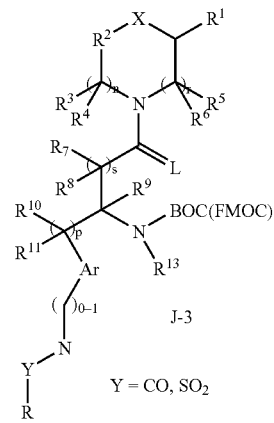

Y = CO, SO$_2$

More specifically, a compound of formula J-1, wherein Z is CN, may be reduced to a compound of formula J-2 using standard hydrogenation conditions known to one skilled in the art.

The compound of formula J-2 may them be further functionalized by reaction with an acid chloride of formula RC(O)Cl to provide acylated amino compounds of formula J-3 wherein Y is CO and there is one methylene. Alternatively, a compound of formula J-2 may be reacted with a sulfonyl chloride of formula RSO$_2$Cl to afford a sulfonamide of formula J-3 wherein Y is SO$_2$ and there is one methylene.

Alternatively, wherein Z is amino, a compound of formula J-1 may then be further functionalized by reaction with an acid chloride of formula RC(O)Cl to provide acylated amino compounds of formula J-3 wherein Y is CO and there is no methylene. Alternatively, a compound of formula J-1 may be reacted with a sulfonyl chloride of formula RSO$_2$Cl to afford a sulfonamide of formula J-3 wherein Y is SO$_2$ and there is no methylene.

Scheme K

Certain target compounds of the present invention may be prepared according to the process outlined in Scheme K below.

Scheme K

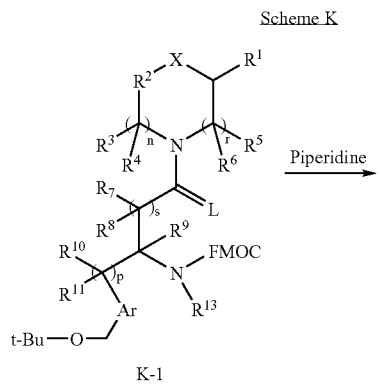

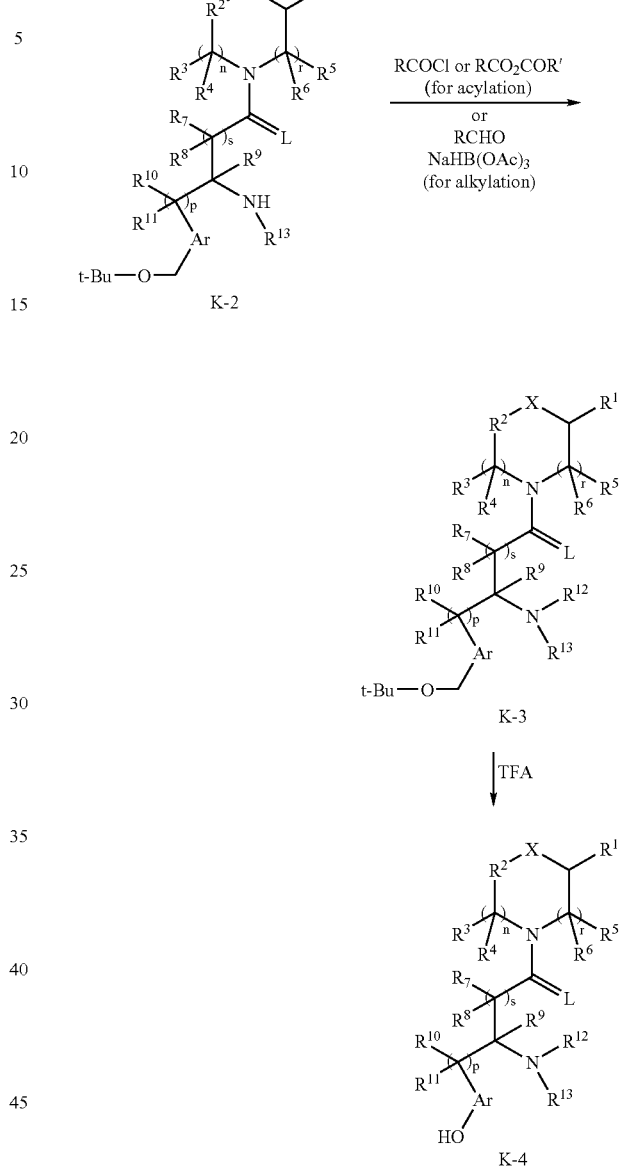

More specifically, a compound of formula K-1 may be deprotected using stabdard deprotection conditions known to those skilled in the art to afford a compound of formula K-2.

The compound of formula K-2 may be further acylated with an appropriate reagent such as an acid chloride of formula RC(O)Cl or an anhydride of formula RCO$_2$C(O)R' which provides a compound of formula K-3 wherein R$^{12}$ is an acyl group. Alternatively, a compound of formula K-2 may be reductively alkylated with an aldehyde of formula RCHO in the presence of a reducing agent such as NaB(OAc)$_3$H which affords a compound of formula K-3 wherein R$^{12}$ is an alkyl group. Deprotection as described previously affords target compounds of the formula K-4.

Scheme L

Certain intermediate compounds of the present invention may be prepared according to the process outlined in Scheme L below.

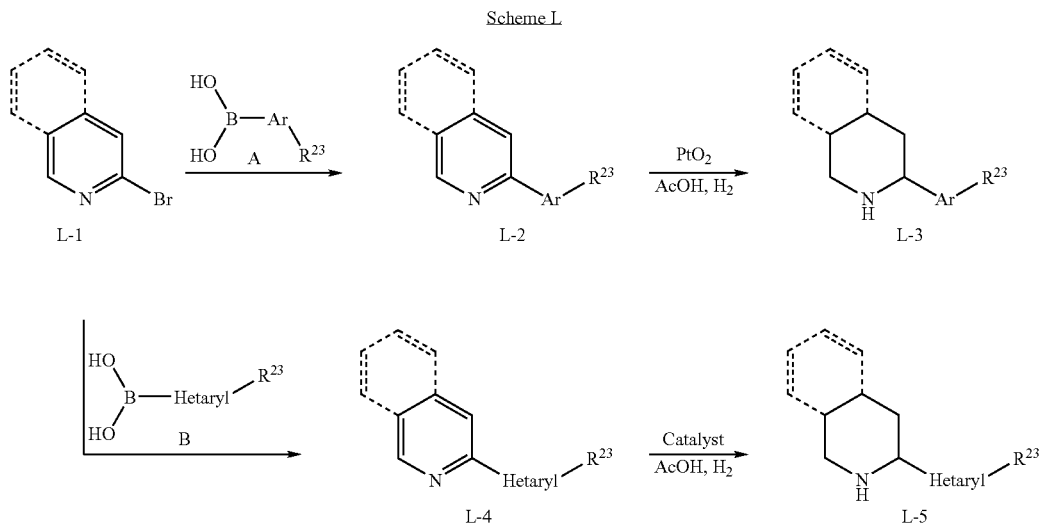

More specifically, certain intermediates of formula L-3 and L-5 may be prepared by Suzuki coupling of a commercially available aryl or heteroaryl bromide represented by but not limited to formula L-1 with a heteroaryl or aryl boronic acid represented by but not limited to compounds of formula A and B which provides a compound of formula L-2 or L-4 respectively. In a similar fashion, the compound of formula L-2 or L-4 may be reduced using standard hydrogenation conditions known to one skilled in the art to provide the intermediates L-3 and L-5.

Using the indicated general synthetic schemes and intermediates described, and varying the appropriate starting materials and reaction conditions as one skilled in the art would know how to do, the compounds of the present invention may be synthesized accordingly.

SPECIFIC SYNTHETIC EXAMPLES

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents.

Unless otherwise indicated, $^1$H NMR's were run on a Bruker AC-300 instrument. Mass spectral analyses were performed on a Fisons instrument (Hewlett-Packard HPLC driven electrospray MS instrument).

Preparation of Key Intermediates and Selected Exemplified Compounds

Example 1

3-(4-phenyl-1H-imidazol-2-yl)-1,2,3,4-tetrahydro-isoquinoline

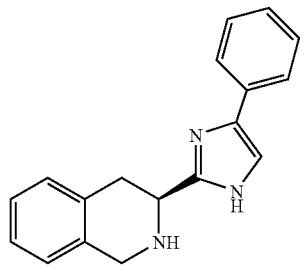

A. 3-(2-oxo-2-phenyl-ethylcarbamoyl)-3,4-dihydro-1H-isoquinoline-2-carboxylic acid tert butyl ester

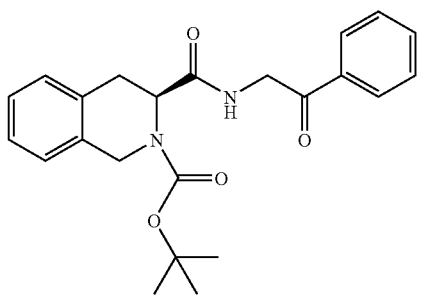

3,4-Dihydro-1H-isoquinoline-2,3-dicarboxylic acid-2-tertbutyl ester (2.77 g, 10 mmol) and 2-amino-1phenyl-ethanone (1.71 g, 10 mmol), and HOBT (1-hydroxybenzotriazole) (2.70 g, 20 mmol) were dissolved in dichloromethane (100 ml). The solution was cooled to 0° C. and then (4-dimethylamino-butyl)-ethyl-carbodiimide (2.29 g, 12 mmol) was added followed by NMM (N-methylmorpholine) (1.31 g, 13 mmol). The reaction mixture was then warmed to room temperature. After 72 hours the reaction mixture was extracted with water, and the organic phase extracted consecutively with saturated NaHCO₃, 2N citric acid and NaHCO₃, dried over MgSO₄, filtered and concentrated to yield the title product as a yellow foam. Liquid chromatography (LC) indicated the compound was 86% pure (214 nm), and was used without further purification.

B. 3-(4-phenyl-1H-imidazol-2-yl)-3,4,-dihydro-1H-isoquinoline-2-carboxylic acid tert-butyl ester

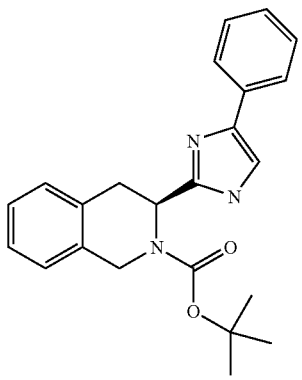

The product prepared in Step A above (3.55 g, 9 mmol), NH₄OAc (ammonium acetate) (20.8 g, 270 mmol) and AcOH (acetic acid) (30 mL) were combined at room temperature and the reaction mixture was warmed on a steam bath for about 3 hours. The reaction mixture was then cooled to room temperature and poured into an ice slurry mix (400 g). To this mixture was added concentrated ammonium hydroxide (50 mL) and ethyl ether. The layers were separated, and the aqueous phase washed with a second portion of ethyl ether. The organic phases were combined, dried over MgSO₄, filtered, and concentrated under reduced pressure to yield a brown foam. This sample was purified by preparative HPLC to yield the purified title compound as a white powder. LC indicated the sample was 96% pure at 214 nm.
Measured MW (MH⁺): 376

C. 3-(4-phenyl-1H-imidazol-2-yl)-1,2,3,4-tetrahydro-isoquinoline

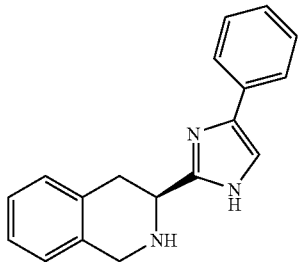

Triflouroacetic acid (TFA) (4 mL) was cooled in a test tube to about 0° C. To the cool solvent was then added the product prepared in Step B (0.75 g, 2 mmol) above. The reaction mixture was allowed to warm to room temperature over about 45 minutes. Excess TFA was removed under a stream of N₂ as. The residue was partitioned between dichloromethane (15 mL) and saturated NaHCO₃. The aqueous phase was then re-extracted with a second portion of dichloromethane and the organic phases combined, dried over MgSO₄ and filtered, to yield the title compound in dichloromethane solution. The filtrate was used in the next step without further purification or isolation.
Measured MW (MH⁺): 276

Example 2

3-(5-Phenyl-oxazol-2-yl)-1,2,3,4-tetrahydro-isoquinoline

Dehydration of 3-(2-oxo-2-phenyl-ethylcarbamoyl)-3,4-dihydro-1H-isoquinoline-2-carboxylic acid benzyl ester (prepared in a similar manner as 3-(2-oxo-2-phenyl-ethylcarbamoyl)-3,4-dihydro-1H-isoquinoline-2-carboxylic acid tert butyl ester of Example 1) with POCl₃ yields the following intermediate compound:

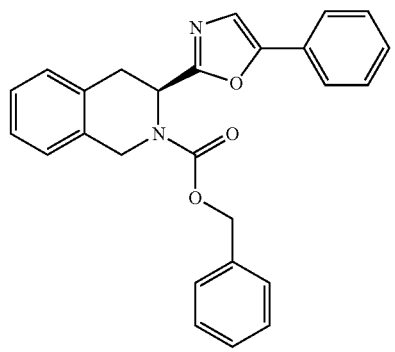

The CBZ group is readily removed from the resulting oxazole by treatment with iodotrimethylsilane. The resulting nor-amine oxazole intermediate can be carried on to prepare various exemplified compounds.

Example 3

3-(5-methyl-4-phenyl-1H-imidazol-2-yl)-3,4-dihydro-1H-isoquinoline

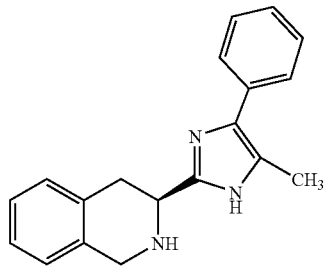

A. 3-(5-methyl-4-phenyl-1H-imidazol-2-yl)-3,4-dihydro-1H-isoquinoline-2-carboxylic acid tert-butyl ester

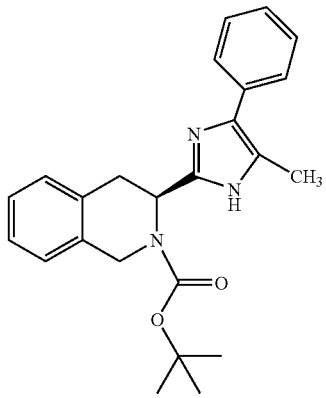

3-Formyl-3,4-dihydro-1H-isoquinoline-2-carboxylic acid tert-butyl ester (1.83 g, 7 mmol) was combined with AcOH (25 mL) to which was immediately added 1-phenyl-propane-1,2-dione (3.11 g, 21 mmol) and NH₄OAc (13.49 g, 175 mmol). The reaction mixture was then placed on a steam bath and heated under an argon atmosphere for 20 minutes. The reaction mixture was cooled in an ice bath and then added to an ice slurry (44 g). The resulting mixture was basified by addition of concentrated NH₄OH (50 mL) and then extracted twice with diethyl ether (150 mL each). The combined organic phases were dried over MgSO4, filtered and concentrated to yield crude product. This material was purified by preparative HPLC to yield the title compound as a white solid.

Measured MW (MH⁺): 390

B. 3-(5-methyl-4-phenyl-1H-imidazol-2-yl)-3,4,-dihydro-1H-isoquinoline

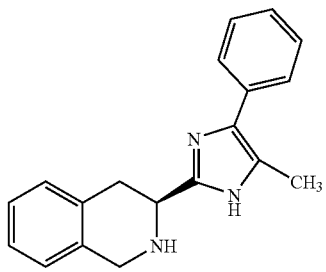

To a solution of TFA (5 mL) cooled to about 0° C. was added the compound prepared in Step A above (1.10 g, 2.82 mmol) and the reaction mixture stirred for about 30 minutes. The reaction mixture was then removed from the ice bath and allowed to warm to room temperature. Excess TFA was removed under a stream of N₂. The residue was partitioned between saturated NaHCO₃ and dichloromethane. The aqueous phase was washed with a second portion of dichloromethane and the organic phases combined. The combined organic phase was dried over Na₂SO₄, then filtered to yield the title product as a solution in dichloromethane, which was used without further purification or isolation.

Example 4

(S)-2-(3-Phenyl-[1,2,4]oxadiazol-5-yl)-piperidine

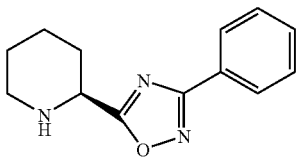

A. O-Acylamidoxime

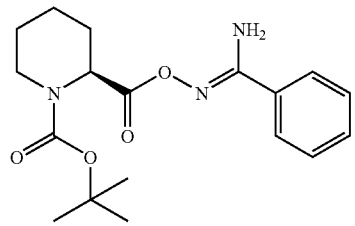

A solution of (S)-1-(tert-butoxycarbonyl)-2-piperidinecarboxylic acid (0.229 g, 1.00 mmol) and N-hydroxybenzamidine (0.140 g, 1.03 mmol) in dichloromethane (10 ml) was cooled in an ice bath. After one hour HOBT (0.27 g, 2.0 mmol), NMM (0.24 ml, 2.2 mmol), and EDCI (0.25 g, 1.3 mmol) were added sequentially with stirring and the resulting yellow solution was slowly warmed to room temperature. Upon disappearance of starting materials monitored by tlc, the reaction was quenched by addition of cold water. The separated organic phase was washed with saturated NaHCO₃ aqueous solution, 2 N citric acid aqueous solution, saturated NaHCO₃ aqueous solution, and dried over Na₂SO₄. After filtration and evaporation, the residue (0.216 g of bright yellow oil) was analyzed and determined to be O-acylamidoxime of sufficient purity (HPLC: 77% @ 254 nm, 75% @ 214 nm) for the next reaction. MS (ES⁺) (relative intensity): 348.3 (100) (M+1).

B. (S)-2-(3-Phenyl-[1,2,4]oxadiazol-5-yl)-piperidine-1-carboxylic acid tert-butyl ester

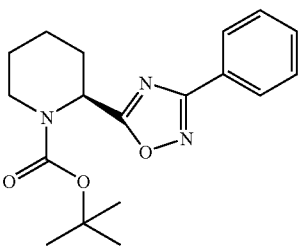

A solution of the crude O-acylamidoxime (0.216 g) in pyridine (10 ml) was heated to reflux. After four hours, analysis by HPLC indicated the reaction was complete. The reaction mixture was cooled to room temperature and concentrated in vacuo to afford a residue that was subjected to flash column chromatography on silica gel (eluent: hexane—EtOAc 3:1, v/v). Obtained 0.132 g [40% for two steps] of oxadiazole) as a colorless oil. ¹H NMR (300 MHz, CDCl₃): δ 1.48 [(9H, s) overlapping 2H, m], 1.73 (2H, dt, J=13.4, 2.7 Hz), 1.94 (1H, m), 2.38 (1H, d, J=13.4 Hz), 3.04 (1H, br t), 4.11 (1H br s) 5.65 (1H, br d), 7.44–7.56 (3H, m), 8.09 (2H, dd, J=7.4, 2.8 Hz); MS (ES$^+$) (relative intensity): 274 (100) (M-tBu), 681 (85) (2M+Na).

C. (S)-2-(3-Phenyl-[1,2,4]oxadiazol-5-yl)-piperidine

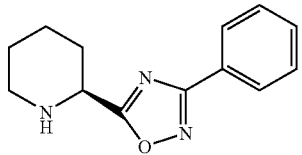

An ice-cold solution of 10% TFA in dichloromethane was added in one portion to the t-Boc protected piperidine (0.132 g, 0.40 mmol). The reaction was placed in an ice bath and slowly warmed to room temperature. Upon disappearance of starting materials monitored by tlc, the reaction was diluted with acetonitrile and concentrated in vacuo at ambient temperature. Obtained 0.186 g (100% for bis TFA salt) of title piperidine as a beige wax. HPLC showed the crude product to have 100% purity @ 254 nm and 214 nm. $^1$H NMR (300 MHz, CDCl$_3$): δ 1.72 (1H, br t), 1.89 (3H, m), 2.20 (1H, br dt), 2.42 (1H, br d), 3.17 (1H, br t), 3.59 (1H, br d), 4.68 (1H, dd, J=9.7, 3.5 Hz), 7.41–7.53 (3H, m), 7.98 (2H, d, J=8.1 Hz); MS (ES$^+$) (relative intensity): 230 (100) (M+1).

Example 5

2-(4-phenyl-1H-imidazol-2-yl)-piperidine

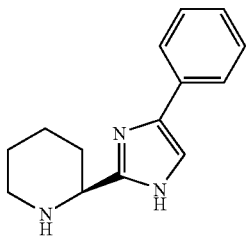

A. 2-(2-oxo-2-phenyl-ethylcarbamoyl)-piperidine-1-carboxylic acid benzyl ester

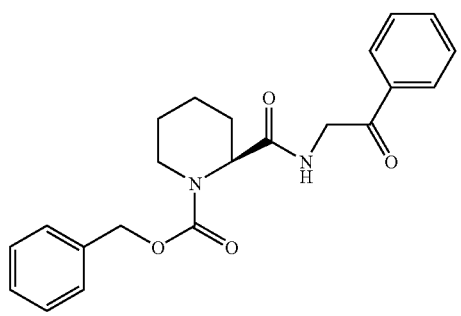

(S)-1-(Carbobenzyloxy)-2-piperidinecarboxylic acid (15.8 g, 60 mmol), 2-amino-1phenyl-ethanone hydrochloride (10.30 g, 60 mmol), and HOBT (1-hydroxybenzotriazole) (16.20 g, 120 mmol) were mixed in dichloromethane (400 mL). The stirring mixture was cooled to 0° C. and then (4-dimethylamino-butyl)-ethyl-carbodiimide (14.90 g, 78 mmol) and NMM (N-methyl-morpholine) (7.27 g, 72 mmol) were added. The reaction mixture was then warmed to room temperature. After 16 hours the reaction mixture was treated with water, and the resulting solid was filtered. The organic phase from the filtrate was separated and washed consecutively with saturated NaHCO$_3$, 2N citric acid, and saturated NaHCO$_3$ once again, then dried over MgSO$_4$, filtered, and concentrated to yield the title product 2-(2-oxo-2-phenyl-ethylcarbamoyl)-piperidine-1-carboxylic acid benzyl ester as a yellow oil, which was used without further purification.

B. 2-(4-phenyl-1H-imidazol-2-yl)-piperidine-1-carboxylic acid benzyl ester 2-(2-Oxo-2-phenyl-ethylcarbamoyl)-piperidine-1-carboxylic acid benzyl ester (22.83 g, 60 mmol), NH$_4$OAc (ammonium acetate) (63.5 g, 824 mmol), AcOH (acetic acid) (30 mL), and xylene (350 mL) were mixed at room temperature, and with stirring the reaction mixture was warmed in an oil bath at 165° C. for about 6 hours. The reaction mixture was then cooled to room temperature and poured into brine. The organic phase was dried over MgSO$_4$, filtered, and concentrated under reduced pressure to yield 31.24 g of off white powder. This sample was triturated in ethyl ether (100 mL), filtered, and rinsed liberally with ethyl ether to yield 15.12 g (70% over two steps) of the desired product 2-(4-phenyl-1H-imidazol-2-yl)-piperidine-1-carboxylic acid benzyl ester as a white solid. HPLC analysis showed the compound to be 100% pure at 254 nm and 98.1% pure at 214 nm.

C. 2-(4-phenyl-1H-imidazol-2-yl)-piperidine 2-(4-Phenyl-1H-imidazol-2-yl)-piperidine-1-carboxylic acid benzyl ester (7.50 g, 20.75 mmol) suspended in ethanol (200 mL) was added to a Parr bottle under a blanket of Ar containing 0.75 g of 10% Pd/C. The sample was then treated with hydrogen for 48 hours at a pressure of 45 psi. The resulting mixture was filtered through Dicalite and concentrated under reduced pressure to give 5.45 g of brown oil. This material was triturated consecutively with ethyl ether, then ice cold acetonitrile (10 mL). The resulting solid was filtered and rinsed with 5 mL of ice cold acetonitrile to yield 2.86 g (61%) of desired 2-(4-phenyl-1H-imidazol-2-yl)-piperidine as a white solid, which was 99.6% pure by HPLC at 254 and 214 nm. (LC/MS; Measured MW (MH$^+$): 228)

Example 6

2-(5-Phenyl-oxazol-2-yl)-piperidine

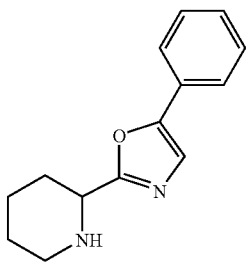

C. 2-(5-Phenyl-oxazol-2-yl)-piperidine-1-carboxylic acid benzyl ester

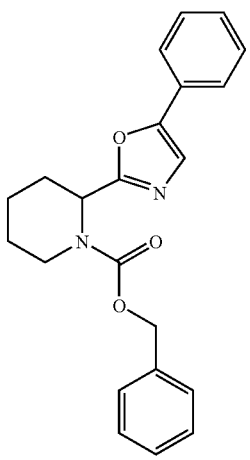

To 0.8 g (2.0 mmol) of 2-(2-Oxo-2-phenyl-ethylcarbamoyl)-piperidine-1-carboxylic acid benzyl ester was added 4 mL of phosphorus oxychloride. The resulting mixture was heated to 120° C. under Argon for one hour. The mixture was poured over ice and the pH was adjusted to pH~7 with addition of ammonium hydroxide solution. The resulting solution was extracted three times with chloroform. The combine organic extracts were dried over magnesium sulfate and concentrated to a brown oil. The residue was dissolved in methylene chloride and filtered through a plug of silica gel. The plug was then rinsed with a 5% methanol in chloroform solution. The filtrate was concentrated to 0.56 g (1.5 mmol, 75% crude yield) of 2-(5-Phenyl-oxazol-2-yl)-piperidine-1-carboxylic acid benzyl ester, a brown oil. The oil was 80% pure by LC analysis and was used as is without further purification.

D. 2-(5-Phenyl-oxazol-2-yl)-piperidine

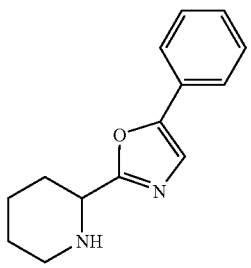

To a solution of 0.56 g (1.5 mmol) of 2-(5-Phenyl-oxazol-2-yl)-piperidine-1-carboxylic acid benzyl ester in 5 mL of chloroform, cooled in an ice bath under argon, was added 5 mL of trimethylsilyliodide. The mixture was allowed to slowly warm to room temperature and stir for five hours. To the reaction mixture was added 10 mL of methanol and the resulting mixture was allowed to stir at room temperature for 0.5 hour. The resulting mixture was partitioned between diethyl ether and 2N hydrochloric acid. The aqueous layer was separated, basified with 2N sodium hydroxide and extracted twice with diethyl ether. The combined ethyl ether extracts were dried over magnesium sulfate and concentrated to 0.20 g (0.88 mmol, 58% yield) of a yellow oil. The oil was 98% pure by LC analysis.

Example 7

(S)-2-tert-Butoxycarbonylamino-3-(4-carbamoyl-2,6-dimethylphenyl)-propionic Acid

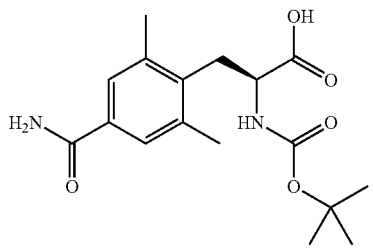

A. (S)-2-tert-Butoxycarbonylamino-3-(2,6-dimethyl-4-trifluoromethanesulfonylphenyl)-propionic Acid Methyl Ester

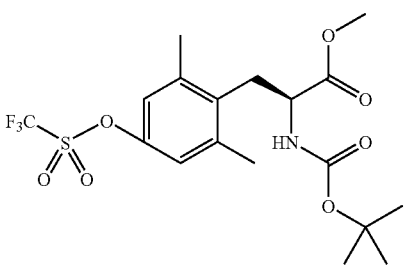

Into a cool solution of Boc-L-(2,6-diMe)Tyr-OMe (7.0 g, 21.6 mmol) and N-phenyltrifluoromethanesulfonimide (7.9 g, 22.0 mmol) in dichloromethane (60 mL) was added triethylamine (3.25 mL, 23.3 mmol). The resulting solution was stirred at 0° C. for 1 hr and slowly warmed to rt. Upon disappearance of starting materials monitored by Tlc, the reaction was quenched by addition of water. The separated organic phase was washed with 1 N NaOH aqueous solution, water and dried over $Na_2SO_4$ overnight. After filtration and evaporation, the residue was purified by flash column chromatography (eluent: EtOAc-hexane: 3:7, v/v) to give the title triflate. 9.74 g, 99%; 1H NMR (300 MHz, $CDCl_3$): δ 1.36 (9H, s), 2.39 (6H, s), 3.06 (2H, d, J=7.7 Hz), 3.64 (3H, s), 4.51–4.59 (1H, m), 5.12 (1H, d, J=8.5 Hz), 6.92 (2H, s); MS(ES+) (relative intensity): 355.8 (100) (M-Boc)+.

B. (S)-4-(2-tert-Butoxycarbonylamino-2-methoxycarbonyl-ethyl)-3,5-dimethylbenzoic Acid

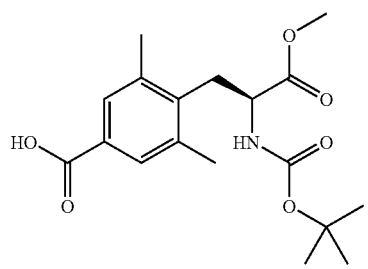

To a suspension of triflate (9.68 g, 21.3 mmol), $K_2CO_3$ (14.1 g, 0.102 mol), $Pd(OAc)_2$ (0.48 g, 2.13 mmol) and 1,1'-bis(diphenylphosphino)ferrocene (DPPF, 2.56 g, 4.47 mmol) in DMF (48 mL) was bubbled in gaseous CO in 15 min. The mixture was heated to 60° C. for 8 hr with CO balloon. The cool mixture was partitioned between $NaHCO_3$ and EtOAc, and filtered. The aqueous layer was separated, acidified with 10% citric acid aqueous solution, extracted with EtOAc, and finally dried over $Na_2SO_4$. Recrystallization from EtOAc-hexane afforded the title acid. 7.05 g, 94%; 1H NMR (300 MHz, $CDCl_3$): δ 1.36 (9H, s), 2.42 (6H, s), 3.14 (2H, J=7.4 Hz), 3.65 (3H, s), 4.57–4.59 (1H, m), 5.14 (1H, d, J=8.6 Hz), 7.75 (2H, s); MS(ES+) (relative intensity): 251.9 (100) (M-Boc)+.

C. (S)-2-tert-Butoxycarbonylamino-3-(4-carbamoyl-2,6-dimethylphenyl)propionic Acid Methyl Ester

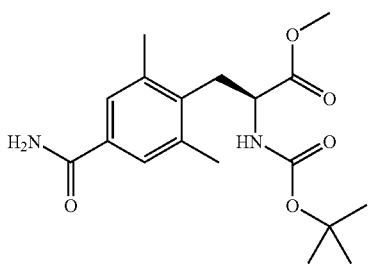

Into a stirrng solution of the benzoic acid from Step B (3.00 g, 8.54 mmol), PyBOP (6.68 g, 12.8 mmol) and HOBt (1.74 g, 12.8 mmol) in DMF (36 mL) was added DIPEA (5.96 mL, 34.2 mmol) and $NH_4Cl$ (0.92 g, 17.1 mmol). The resulting mixture was stirred at rt for 40 min before being partitioned between aqueous $NH_4Cl$ solution and EtOAc. The separated organic phase was washed with 2 N citric acid aqueous solution, saturated aqueous $NaHCO_3$ solution and brine, and dried over $Na_2SO_4$ overnight. After concentration, the residue was purified by flash column chromatography (eluent: EtOAc) to give the title amide. 3.00 g, 100%; 1H NMR (300 MHz, $CDCl_3$): δ 1.36 (9H, s), 2.39 (6H, s), 3.11 (2H, J=7.2 Hz), 3.65 (3H, s), 4.53–4.56 (1H, m), 5.12 (1H, d, J=8.7 Hz), 5.65 (1H, br s), 6.09 (1H, br s), 7.46 (2H, s); MS(ES+) (relative intensity): 250.9 (100) (M-Boc)+.

D. (S)-2-tert-Butoxycarbonylamino-3-(4-carbamoyl-2,6-dimethylphenyl)propionic Acid

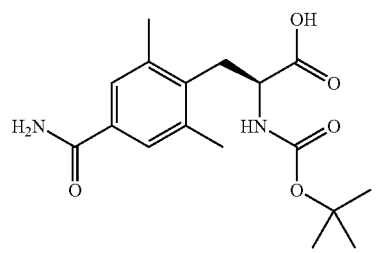

Into an ice-cooled solution of methyl ester from Step C (2.99 g, 8.54 mmol) in THF (50 mL) was added an aqueous LiOH solution (1 N, 50 mL) and stirred at 0° C. Upon disappearance of starting materials monitored by Tlc, the organic solvents were removed and the aqueous phase was neutralized with cooled 1 N HCl at 0° C., and extracted with EtOAc, finally dried over $Na_2SO_4$ overnight. Filtration and evaporation to dryness led to the title acid. 2.51 g, 87%; $^1$H NMR (300 MHz, DMSO-$d_6$): δ 1.30 (9H, s), 2.32 (6H, s), 2.95(1H, dd, J=8.8, 13.9 Hz), 3.10 (1H, dd, J=6.2, 14.0 Hz), 4.02–4.12 (1H, m), 7.18–7.23 (2H, m), 7.48 (2H, s), 7.80 (1H, s); MS(ES+) (relative intensity): 236.9 (6) (M-Boc)+.

Example 8

2,2-dimethyl-propionic acid 4-{2-amino-3-oxo-3-[2-(4-phenyl-1H-imidazol-2-yl)-piperidin-1-yl]-propyl}-3,5-dimethyl-phenyl ester

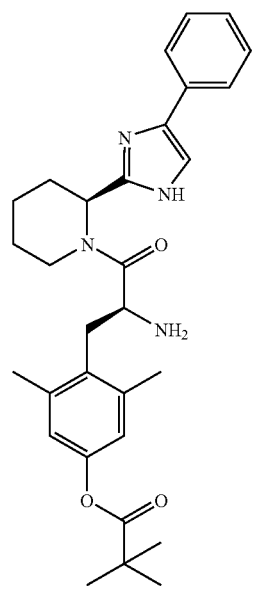

A. {1-(4-hydroxy-2,6-dimethyl-benzyl)-2-oxo-2-[2-(4-phenyl-1H-imidazol-2-yl)-piperidin-1-yl]-ethyl}-carbamic acid tert-butyl ester

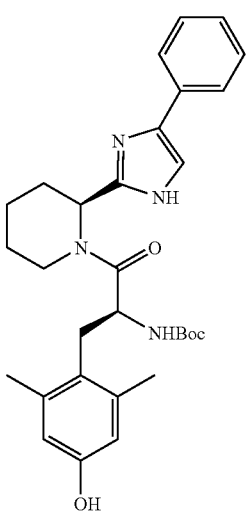

To a mixture of 114 mg (0.5 mmol) of 2-(4-phenyl-1H-imidazol-2-yl)-piperidine, 155 mg (0.5 mmol) of 2-tert-butoxycarbonylamino-3-(4-hydroxy-2,6-dimethyl-phenyl)-propionic acid, 135 mg (1.0 mmol) of hydroxybenzotriazole hydrate, and 115 mg (0.6 mmol) of 1-[3-(dimethylamino)propyl]-3-ethylcarbodiimide hydrochloride was added 1 mL of dimethylformamide. The resulting mixture was allowed to stir at room temperature under argon overnight. The mixture was partitioned between ethyl acetate and water. The organic layer was separated, washed with citric acid, sodium bicarbonate solution, and water, dried over magnesium sulfate and concentrated. Obtained 214 mg (0.41 mmol, 82% yield) of the crude product {1-(4-hydroxy-2,6-dimethyl-benzyl)-2-oxo-2-[2-(4-phenyl-1H-imidazol-2-yl)-piperidin-1-yl]-ethyl}-carbamic acid tert-butyl ester, which was used for the next step without further purification.

B. 2,2-dimethyl-propionic acid 4-{2-amino-3-oxo-3-[2-(4-phenyl-1H-imidazol-2-yl)-piperidin-1-yl]-propyl}-3,5-dimethyl-phenyl ester

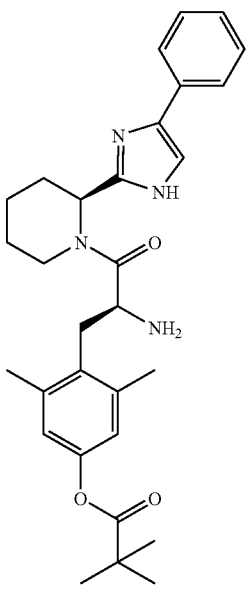

To a solution of {1-(4-hydroxy-2,6-dimethyl-benzyl)-2-oxo-2-[2-(4-phenyl-1H-imidazol-2-yl)-piperidin-1-yl]-ethyl}-carbamic acid tert-butyl ester in 5 mL of chloroform, cooled in and ice bath under argon, was added 2,2-dimethyl-propionyl chloride 62 uL (0.5 mmol), followed by 75 uL (0.5 mmol) of DBU. The mixture was allowed to slowly warm to room temperature and stir overnight. LC analysis indicated that the reaction was complete. To this mixture was added 1 mL of trifluoroacetic acid. After stirring for 2 hours, LC indicated that reaction was ~50% complete. An additional 1 mL of trifluoroacetic acid was added. After stirring an additional hour, LC analysis indicated the reaction was complete. The mixture was concentrated and purified on a Gilson prep LC. Obtained 61 mg (0.10 mmol, 25% yield) of the product 2,2-dimethyl-propionic acid 4-{2-amino-3-oxo-3-[2-(4-phenyl-1H-imidazol-2-yl)-piperidin-1-yl]-propyl}-3,5-dimethyl-phenyl ester as a white powder. $^1$H NMR (300 MHz, CD$_3$OD): δ 1.08–1.75 (13H, m), 1.88–2.22 (3H, m), 2.41–2.69 (4H, m), 3.12–3.53 (3H, m), 4.57–5.02 (3H, m), 5.88 (0.3H, t), 6.60 (0.3H, s), 6.85 (1H, s), 7.39–7.88 (6H, m).

TLC (90:9:1, CHCl$_3$:MeOH:NH$_4$OH) Rf=0.50 MS(ES+) (relative intensity): 503.0 (100).

Example 9

S,S isomer of 4-{2-amino-3-oxo-3-[3-(4-phenyl-1H-imidazol-2-yl)-3,4-dihydro-1H-isoquinolin-2-yl]-propyl}-3,5-dimethyl-benzamide

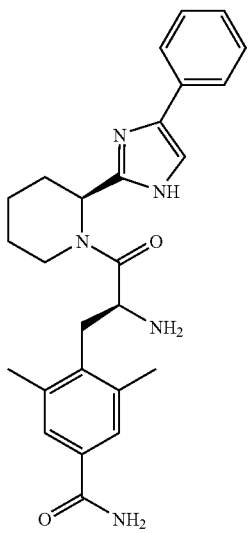

A. {1-(4-carbamoyl-2,6-dimethyl-benzyl)-2-oxo-2-[3-(4-phenyl-1H-imidazol-2-yl)-3,4-dihydro-1H-isoquinolin-2-yl]-ethyl}-carbamic acid tert-butyl ester

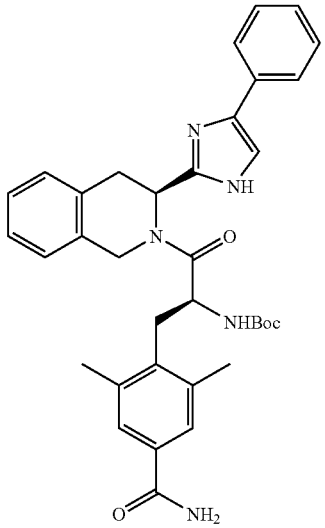

To a mixture of 220 mg (0.8 mmol) of 3-(4-phenyl-1H-imidazol-2-yl)-1,2,3,4-tetrahydro-isoquinoline, 269 mg (0.8 mmol) of 2-tert-butoxycarbonylamino-3-(4-carbamoyl-2,6-dimethyl-phenyl)-propionic acid, 216 mg (1.6 mmol) of of hydroxybenzotriazole hydrate and 184 mg (0.96 mmol) of 1-[3-(dimethylamino)propyl]-3-ethylcarbodiimide hydrochloride was added 3 mL of dimethylformamide. The resulting mixture was allowed to stir overnight at room temperature under argon. The mixture was then partitioned between ethyl acetate and water. The organic layer was separated, dried over magnesium sulfate and concentrated. The product {1-(4-carbamoyl-2,6-dimethyl-benzyl)-2-oxo-2-[3-(4-phenyl-1H-imidazol-2-yl)-3,4-dihydro-1H-isoquinolin-2-yl]-ethyl}-carbamic acid tert-butyl ester was taken to the next step without further purification.

B. S,S isomer of 4-{2-amino-3-oxo-3-[3-(4-phenyl-1H-imidazol-2-yl)-3,4-dihydro-1H-isoquinolin-2-yl]-propyl}-3,5-dimethyl-benzamide

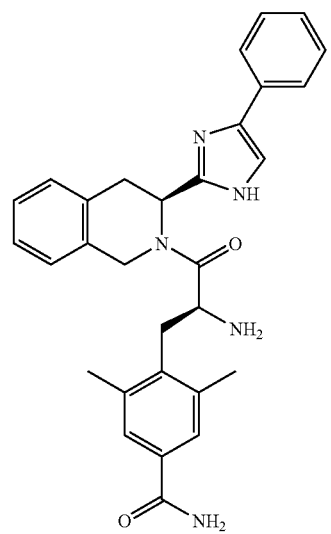

To 0.8 mmol of {1-(4-carbamoyl-2,6-dimethyl-benzyl)-2-oxo-2-[3-(4-phenyl-1H-imidazol-2-yl)-3,4-dihydro-1H-isoquinolin-2-yl]-ethyl}-carbamic acid tert-butyl ester cooled in an ice bath under argon, was added 3 mL of trifluoroacetic acid. After stirring for 3 hours, the reaction mixture was concentrated and purified on a Gilson prep LC system. Obtained 79 mg (0.13 mmol) of the pure S,S isomer of 4-{2-amino-3-oxo-3-[3-(4-phenyl-1H-imidazol-2-yl)-3,4-dihydro-1H-isoquinolin-2-yl]-propyl}-3,5-dimethyl-benzamide and 58 mg (0.09 mmol) of a mix of diastereomers for a total of 137 mg (0.22 mmol, 28% yield). Data for "pure" isomer (may contain a trace of other isomer as evident by tlc): $^1$H NMR (300 MHz, CD$_3$OD): δ 1.85 (0.5H, dd), 2.13–2.51 (6H, m), 2.91 (0.4H, dd), 3.18–3.52 (4H, m), 3.70 (0.5H, d), 4.28–4.47 (1H, m), 4.60–5.06 (2.5H, m), 5.62 (0.5H, t), 6.95–7.90 (13H, m).

TLC (90:9:1, CHCl$_3$:MeOH:NH$_4$OH) Rf=0.31 major, 0.23 minor MS(ES+) (relative intensity): 494.1 (100).

Example 10

4-{2-Amino-3-oxo-3-[2-(4-phenyl-1H-imidazol-2-yl)-piperidin-1-yl]-propyl}-N-methyl-benzamide

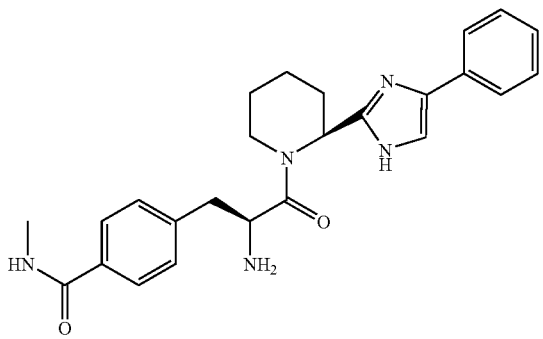

A. 4-{2-(9H-Fluoren-9-ylmethoxycarbonylamino)-3-oxo-3-[2-(4-phenyl-1H-imidazol-2-yl)-piperidin-1-yl]-propyl}-benzoic acid tert-butyl ester

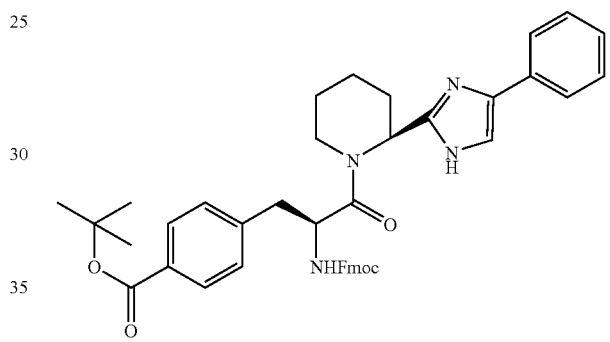

To a mixture of 182 mg (0.8 mmol) of 2-(4-Phenyl-1H-imidazol-2-yl)-piperidine, 390 mg (0.8 mmol) of 4-[2-carboxy-2-(9H-fluoren-9-ylmethoxycarbonylamino)-ethyl]-benzoic acid tert-butyl ester, 216 mg (1.6 mmol) of 1-[3-(dimethylamino)propyl]-3-ethylcarbodiimide hydrochloride, and 192 mg of 1-hydroxybenzotriazole hydrate was added 2.5 mL of dimethylformamide. The mixture was allowed to stir at room temperature overnight. The mixture was then partitioned between ethyl acetate and water. The organic layer was separated, dried over MgSO4 and concentrated to 670 mg of crude product.

B. 4-{2-(9H-Fluoren-9-ylmethoxycarbonylamino)-3-oxo-3-[2-(4-phenyl-1H-imidazol-2-yl)-piperidin-1-yl]-propyl}-benzoic acid

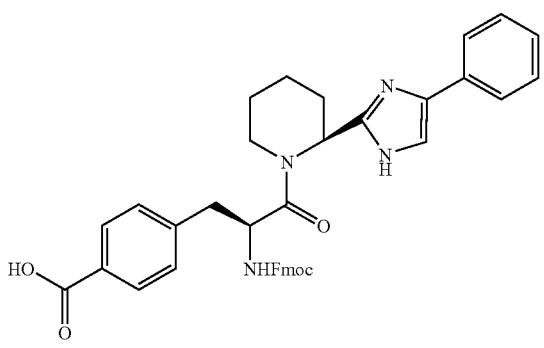

To 670 mg of the product from step A (crude but assumed to be 0.8 mmol based on the previous reaction), cooled in an ice bath under argon, was added 3 mL of trifluroacetic acid. The resulting mixture was allowed to slowly return to room temperature and stir for 5 hours. The mixture was then partitioned between saturated NaHCO3 solution and ethyl acetate. The organic layer was separated, dried over MgSO4 and concentrated to 139 mg of a white solid (83% pure by LC). The aqueous layer was extracted twice with ethyl acetate and the combined organic layers were dried over MgSO4 and concentrated to 0.10 g of yellow oil (70% pure by LC). Obtain a total of 239 mg (0.37 mmol, 47% yield) of crude title product.

C. {1-(4-Methylcarbamoyl-benzyl)-2-oxo-2-[2-(4-phenyl-1H-imidazol-2-yl)-piperidin-1-yl]-ethyl}-carbamic acid 9H-fluoren-9-ylmethyl ester

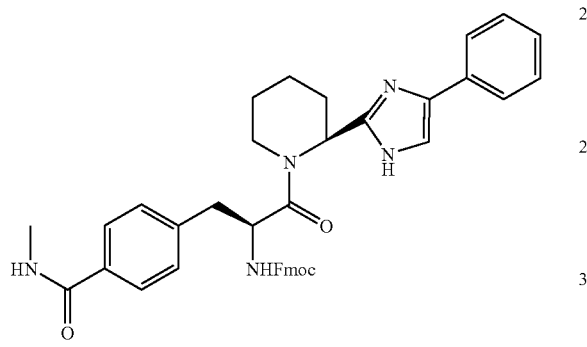

To a mixture of 150 mg (0.23 mmol) of the product from step B, 17 mg (0.25 mmol) of methylamine hydrochloride, 27 uL (0.25 mmol) of N-methylmorpholine, 62 mg (0.46 mmol) of 1-hydroxybenzotriazole hydrate, and 57 mg (0.3 mmol) of of 1-[3-(dimethylamino)propyl]-3-ethylcarbodiimide hydrochloride was added 2 mL of dimethylformamide. The resulting mixture was allowed to stir at room temperature under argon for 5.5 hours. The mixture was partitioned between ethyl acetate and water and separated. The organic layer was dried over MgSO4 and concentrated. Obtained 148 mg (0.21 mmol, 92% yield) of crude product.

D. 4-{2-Amino-3-oxo-3-[2-(4-phenyl-1H-imidazol-2-yl)-piperidin-1-yl]-propyl}-N-methyl-benzamide

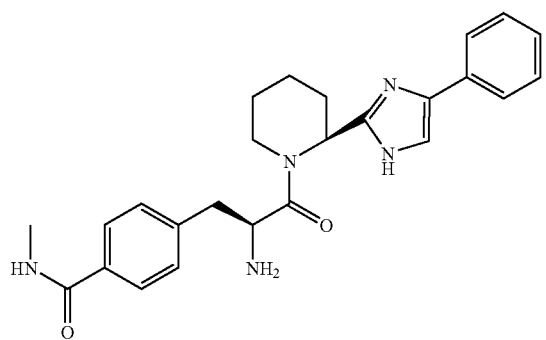

To a solution of 148 mg (0.21 mmol) of the product from step C in 2 mL of chloroform was added 2 ml of piperidine. The resulting mixture was allowed to stir at room temperature under argon for 3.5 hours. The reaction mixture was then concentrated and the residue purified on a Gilson prep LC system. The product was lophilized to obtain 47 mg (0.08 mmol, 48% yield) of the desired product as a white powder assumed to be a TFA salt. $^1$H NMR (300 MHz, CD$_3$OD): δ 1.20–1.45 (2H, m), 1.50–1.80 (4H, m), 1.90–2.40 (2H, m), 2.90 (3H, d), 2.95–3.21 (2H, m), 3.78 (1H, m), 4.54 (1H, d), 5.12 (1H, s), 5.92 (1H, t), 7.28 (1H, d), 7.33–7.88 (10H, m).

TLC (90:9:9, CHCl$_3$:MeOH:NH$_4$OH) Rf=0.33

Example 11

4-{2-Amino-3-oxo-3-[2-(4-phenyl-1H-imidazol-2-yl)-piperidin-1-yl]-propyl}-benzamide

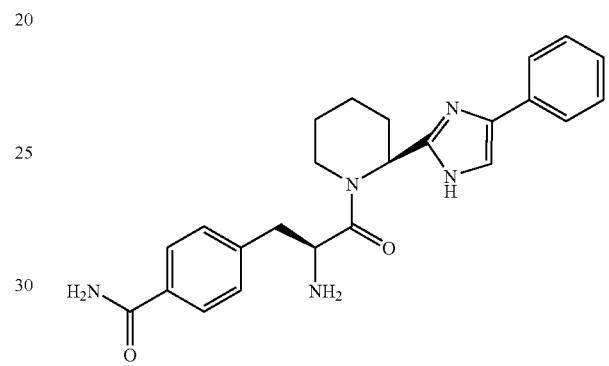

A. {1-(4-Carbamoyl-benzyl)-2-oxo-2-[2-(4-phenyl-1H-imidazol-2-yl)-piperidin-1-yl]-ethyl}-carbamic acid 9H-fluoren-9-ylmethyl ester

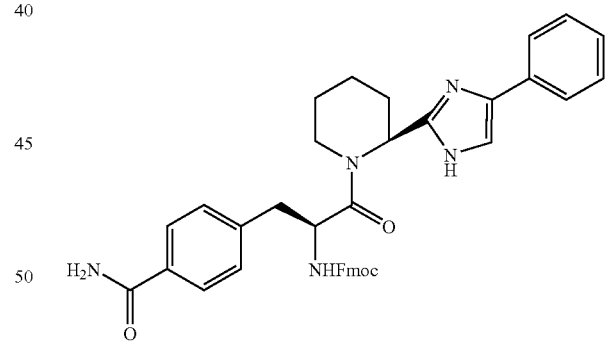

To a mixture of 138 mg (0.5 mmol) of 2-(4-Phenyl-1H-imidazol-2-yl)-piperidine, 215 mg (0.5 mmol) of 3-(4-Carbamoyl-phenyl)-2-(9H-fluoren-9-ylmethoxycarbony-lamino)-propionic acid, 135 mg (1.0 mmol) of hydroxybenzotriazole hydrate, 115 mg (0.6 mmol) of 1-[3-(dimethylamino)propyl]-3-ethylcarbodiimide hydrochloride was added 2 mL of dimethylformamide. The resulting mixture was allowed to stir at room temperature under argon overnight. The mixture was then partitioned between ethyl acetate and water. The organic layer was separated, dried over MgSO4 and concentrated to a yellow oil which was used for the next step without further purification.

B. 4-{2-Amino-3-oxo-3-[2-(4-phenyl-1H-imidazol-2-yl)-piperidin-1-yl]-propyl}-benzamide

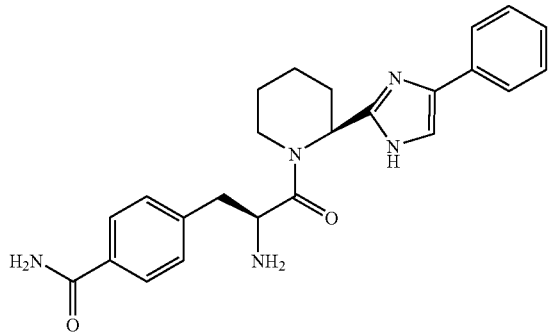

To a solution of the product from step A (assumed to be 0.5 mmol based on the previous step), in 4 mL of chloroform was added 1 mL of piperidine. The mixture was allowed to stir overnight at room temperature under argon. The mixture was then concentrated and the residue purified on a Gilson prep LC system. By LC, the compound was determined to be a 88:12 mixture of diastereomers with the S,S isomer (as drawn) predominating. Obtained 48 mg (0.083 mmol, 17% yield) of product as a pale yellow powder assumed to be a TFA salt. $^1$H NMR (300 MHz, CD$_3$OD): δ 3.10–3.58 (4H, m), 4.20 (0.2H, d), 4.68–5.06 (3H, m), 5.33 (0.2H, m), 5.63 (1H, m), 5.85 (0.2H, m), 7.01–7.23 (2H, m), 7.25–7.67 (10H, m), 7.69–7.88 (3H, m).

TLC (90:9:9, CHCl$_3$:MeOH:NH$_4$OH) Rf=0.53 (minor), 0.60 (major).

Example 12

3-(4-hydroxy-phenyl)-2-isopropylamino-1-[3-(4-phenyl-1H-imidazol-2-yl)-3,4-dihydro-1H-isoquinolin-2-yl]-propan-1-one

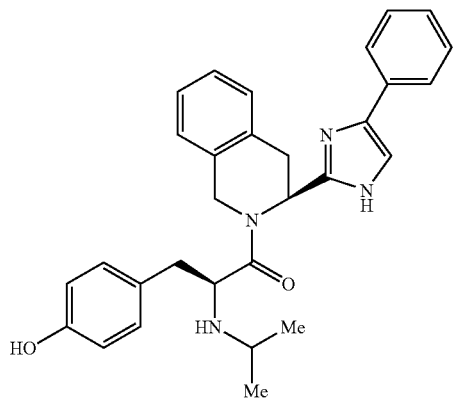

A. {1-(4-tert-butoxy-benzyl)-2-oxo-2-[3-(4-phenyl-1H-imidazol-2-yl)-3,4-dihydro-1H-isoquinolin-2-yl]-ethyl}-carbamic acid 9H-fluoren-9-ylmethyl ester

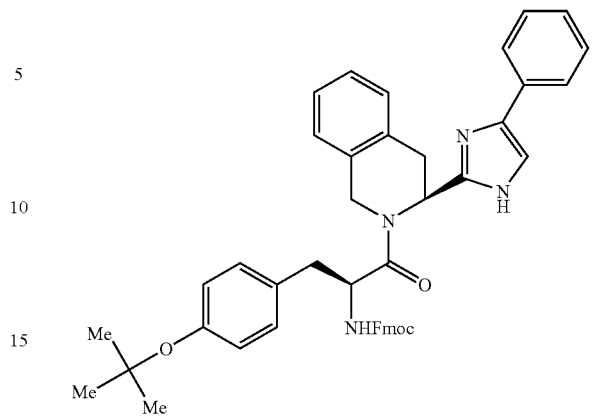

3-(4-tert-Butoxy-phenyl)-2-(9H-fluoren-9-ylmethoxycarbonylamino)-propionic acid (1.93 g, 4.2 mmol) was dissolved in dichloromethane (100 mL), cooled to 0° C., then N-methyl-morpholine (0.42 g, 4.2 mmol) was added neat followed by isobutyl chloroformate (0.52 mL, 4 mmol). After 1.25 hour 3-(4-phenyl-1H-imidazol-2-yl)-1,2,3,4-tetrahydro-isoquinoline (1.10 g, 4 mmol) was added neat and the reaction was allowed to warm to room temperature. After 16 hours the reaction was extracted with water, then saturated NaHCO3, dried over Na2SO4, filtered, and concentrated under reduced pressure to give 2.53 g (88%) of brown foam desired product {1-(4-tert-butoxy-benzyl)-2-oxo-2-[3-(4-phenyl-1H-imidazol-2-yl)-3,4-dihydro-1H-isoquinolin-2-yl]-ethyl}-carbamic acid 9H-fluoren-9-ylmethyl ester, which was used without further purification. (LC/MS; Measured MW (MH$^+$): 717)

B. 2-amino-3-(4-tert-butoxy-phenyl)-1-[3-(4-phenyl-1H-imidazol-2-yl)-3,4-dihydro-1H-isoquinolin-2-yl]-propan-1-one

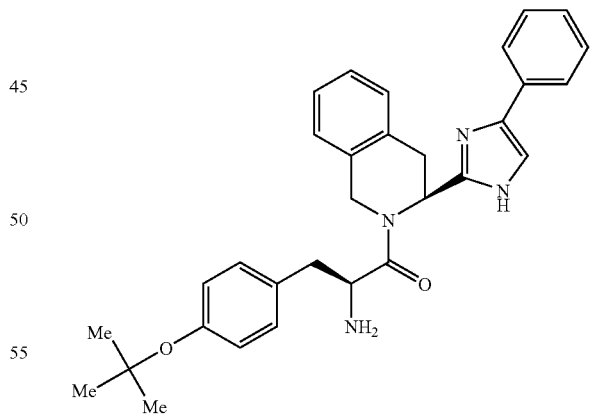

Piperidine in methanol (20%; 2 mL) was added to {1-(4-tert-butoxy-benzyl)-2-oxo-2-[3-(4-phenyl-1H-imidazol-2-yl)-3,4-dihydro-1H-isoquinolin-2-yl]-ethyl}-carbamic acid 9H-fluoren-9-ylmethyl ester (0.20 g, 0.28 mmol) at room temperature. After 30 minutes the reaction was concentrated under reduced pressure, and the residual 200 mg of desired product 2-amino-3-(4-tert-butoxy-phenyl)-1-[3-(4-phenyl-1H-imidazol-2-yl)-3,4-dihydro-1H-isoquinolin-2-yl]-propan-1-one was used as is without further purification (LC/MS; Measured MW (MH+): 495).

C. 3-(4-tert-butoxy-phenyl)-2-isopropylamino-1-[3-(4-phenyl-1H-imidazol-2-yl)-3,4-dihydro-1H-isoquinolin-2-yl]-propan-1-one

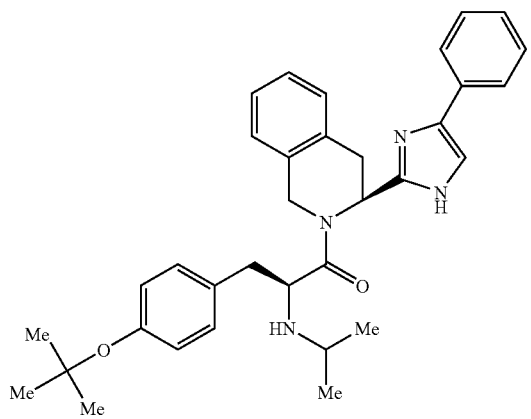

2-Amino-3-(4-tert-butoxy-phenyl)-1-[3-(4-phenyl-1H-imidazol-2-yl)-3,4-dihydro-1H-isoquinolin-2-yl]-propan-1-one (0.145 g, 0.29 mmol) was dissolved in 1,2-dichloroethane (12 mL). Acetone (0.068 g, 1.17 mmol) was added to the solution, followed by acetic acid (0.018 g, 0.29 mmol) and sodium triacetoxyborohydride (0.10 g, 0.47 mmol). After 3 hours the reaction was treated with saturated aqueous NaHCO3 (5 mL) and stirred for 1 hour. The layers were then separated, the organic phase was dried over MgSO4, filtered, and concentrated under reduced pressure to give 0.16 g of clear oil. This oil was treated with ethyl ether (2 mL), and the resulting solid filtered and rinsed with ethyl ether to give 60 mg (38%) of desired product 3-(4-tert-butoxy-phenyl)-2-isopropylamino-1-[3-(4-phenyl-1H-imidazol-2-yl)-3,4-dihydro-1H-isoquinolin-2-yl]-propan-1-one as a white solid, which proved 100% pure by HPLC at 254 and 214 nm, (LC/MS; Measured MW (MH+): 537).

D. 3-(4-hydroxy-phenyl)-2-isopropylamino-1-[3-(4-phenyl-1H-imidazol-2-yl)-3,4-dihydro-1H-isoquinolin-2-yl]-propan-1-one

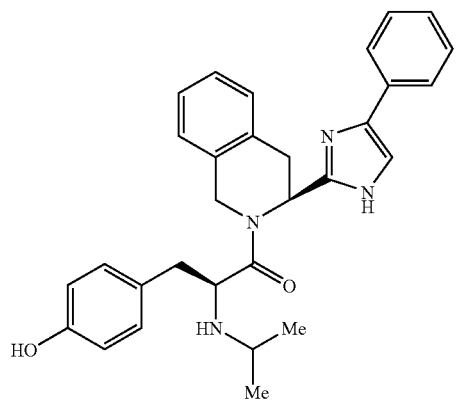

3-(4-tert-Butoxy-phenyl)-2-isopropylamino-1-[3-(4-phenyl-1H-imidazol-2-yl)-3,4-dihydro-1H-isoquinolin-2-yl]-propan-1-one (0.086 g, 0.16 mmol) was added to ice cooled trifluoroacetic acid (3 mL). After 1.5 hour the reaction was concentrated under reduced pressure to give a clear oil. This material was purified via a Gilson preparative HPLC resulting in the isolation of desired product 3-(4-hydroxy-phenyl)-2-isopropylamino-1-[3-(4-phenyl-1H-imidazol-2-yl)-3,4-dihydro-1H-isoquinolin-2-yl]-propan-1-one as a white solid after lyophilization, which proved 100% pure by HPLC at 254 and 214 nm, (LC/MS; Measured MW (MH+): 481).

Example 13

3-(4-Acetoxy-2,6-dimethyl-phenyl)-2-tert-butoxycarbonylamino-propionic acid

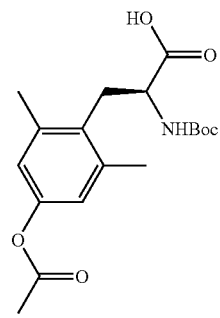

To a solution of 0.77 g (2.5 mmol) of 2-tert-Butoxycarbonylamino-3-(4-hydroxy-2,6-dimethyl-phenyl)-propionic acid and 3 mL of 3N sodium hydroxide solution, cooled in an ice bath, was added 0.89 mL (9.4 mmol) of acetic anhydride dropwise over about 30 seconds. After stirring for 2 hours, the mixture was acidified with addition of 4.5 mL of 2N hydrochloric acid. The mixture was extracted twice with ethyl acetate. The combined organics were dried over magnesium sulfate and concentrate to a clear oil. The title product was used for the next reaction without further purification.

Example 14

Acetic acid 4-{2-amino-3-oxo-3-[2-(5-phenyl-1H-imidazol-2-yl)-piperidin-1-yl]-propyl}-3,5-dimethyl-phenyl ester

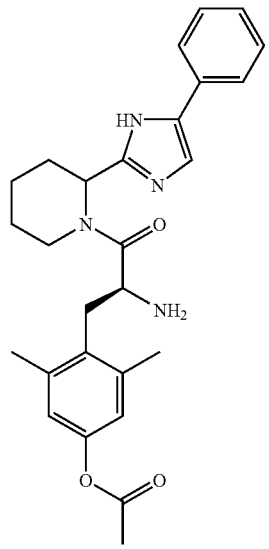

A. Acetic acid 4-{2-tert-butoxycarbonylamino-3-oxo-3-[2-(5-phenyl-1H-imidazol-2-yl)-piperidin-1-yl]-propy}-3,5-dimethyl-phenyl ester

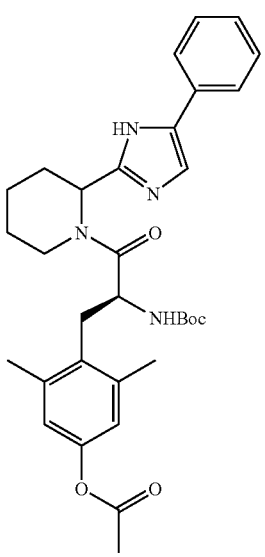

To a mixture of 0.377 g (1.66 mmol) of 2-(5-Phenyl-1H-imidazol-2-yl)-piperidine, 0.72 g (1.66 mmol) of 3-(4-Acetoxy-2,6-dimethyl-phenyl)-2-tert-butoxycarbonylamino-propionic, 0.448 g (3.32 mmol) of hydroxybenzotriazole hydrate, and 0.383 g (1.99 mmol) of 1-[3-(dimethylamino) propyl]-3-ethylcarbodiimide hydrochloride was added 2.5 mL of dimethylformamide. The resulting mixture was allowed to stir at room temperature under argon overnight. The mixture was then partitioned between ethyl acetate and water. The organic layer was separated, dried over magnesium sulfate and concentrated. Obtained 0.81 g (1.4 mmol, 88% yield) of the crude product as a brown oil, which was used for the next reaction without further purification.

B. Acetic acid 4-{2-amino-3-oxo-3-[2-(5-phenyl-1H-imidazol-2-yl)-piperidin-1-yl]-propyl}-3,5-dimethyl-phenyl ester

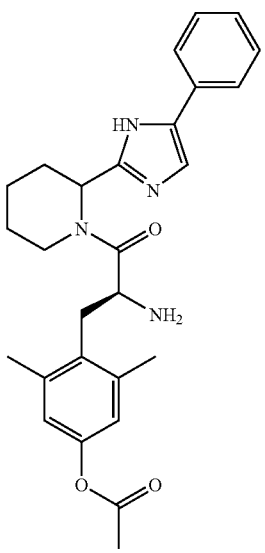

To a solution of 0.81 g (1.4 mmol) of the product from step A in 5 mL of chloroform, cooled in an ice bath, was added 3.5 mL of trifluroacetic acid. The mixture was allowed to slowly return to room temperature and stir under argon for 3 hours. The mixture was concentrated to 0.59 g (1.3 mmol, 93% yield) of product as a brown oil. Half of this was taken to the next step as a crude product. Half was purifed on a Gilson prep LC. Obtained 0.083 g (0.14 mmol) of pure product as a white powder assumed to be a TFA salt.
$^1$H NMR (300 MHz, CD$_3$OD): δ 1.06–1.35 (1H, m), 1.49–1.74 (2H, m), 1.75–2.20 (3H, m), 2.20–40 (6H, m), 2.40–2.70 (1H, m), 3.12–3.71)2H, m), 4.56–5.12 (1.5H, m), 5.92 (0.5H, t), 6.64–6.90 (2H, m), 7.37–7.89 (5H, m).

LC 92% @214 nm

TLC (90:9:1, CHCl$_3$:MeOH:NH$_4$OH) Rf=0.33 (minor), 0.37 (major).

MS(ES+) (relative intensity): 461.3 (100).

Example 16

N-{1-(4-Hydroxy-2,6-dimethyl-benzyl)-2-oxo-2-[2-(5-phenyl-1H-imidazol-2-yl)-piperidin-1-yl]-ethyl}-formamide

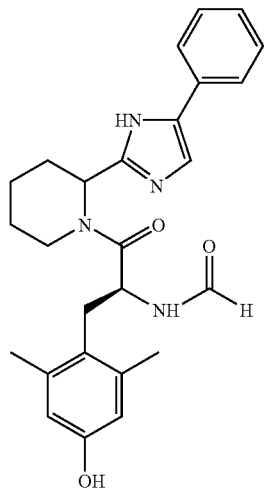

A. Acetic acid 4-{2-formylamino-3-oxo-3-[2-(5-phenyl-1H-imidazol-2-yl)-piperidin-1-yl]-propyl}-3,5-dimethyl-phenyl ester

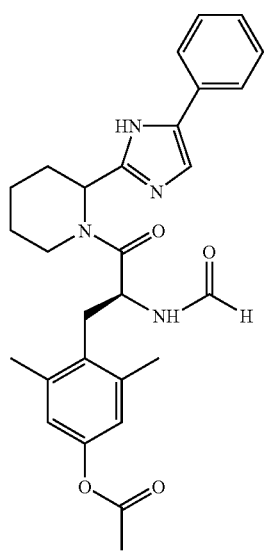

To a solution of 0.7 mmol of acetic acid 4-{2-amino-3-oxo-3-[2-(5-phenyl-1H-imidazol-2-yl)-piperidin-1-yl]-propyl}-3,5-dimethyl-phenyl ester and 0.8 mL of formaldehyde, cooled in an ice bath under argon, was added 0.5 mL of acetic acid. The resulting mixture was allowed to slowly return to room temperature and stir overnight. The mixture was then extracted with ethyl acetate. The ethyl acetate was washed with water, dried over magnesium sulfate and concentrated to 0.39 g of an orange-yellow oil which was taken to the next step without further purification.

B. N-{1-(4-Hydroxy-2,6-dimethyl-benzyl)-2-oxo-2-[2-(5-phenyl-1H-imidazol-2-yl)-piperidin-1-yl]-ethyl}-formamide

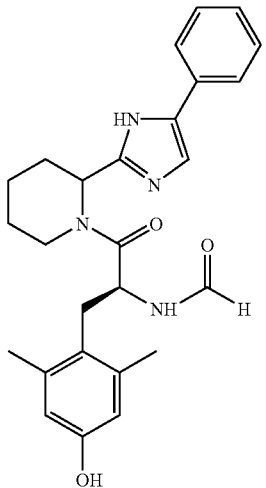

To a solution of 0.34 g (0.7 mmol) of the product from step A in about 10 mL of methanol was added 0.211 g (1.5 mmol) of potassium carbonate. After stirring for 2 hours, LC analysis indicated the reaction was incomplete. An additional 100 mg of potassium carbonate was added and the mixture was stirred two more hours. The reaction was complete by LC analysis. The mixture was filtered and concentrated. The concentrate was purified on a prep LC system to obtain 45 mg (0.08 mmol, 10% yield) of the product as a white powder. The product was assumed to be a TFA salt. $^1$H NMR (300 MHz, CD$_3$OD): δ 0.5 (1H, m), 1.12–1.77 (4H, m), 2.14 (2H, s), 2.15–2.39 (6H, m), 2.92–3.09 (1.6H, dd), 3.32 (3.4H, m), 4.62 (1H, d), 5.06 (0.5H, m), 6.40 (0.5H, d), 6.59 (2H, s), 7.49 (3H, m), 7.88 (3H, m), 8.17 (1H, s).

TLC (90:9:1, CHCl$_3$:MeOH:NH$_4$OH) Rf=0.33
MS(ES+) (relative intensity): 447.3 (100).

Example 16

4-{2-amino-3-oxo-3-[2-(4-phenyl-1H-imidazol-2-yl)-piperidin-1-yl]-propyl}-3,5-dimethyl-benzamide

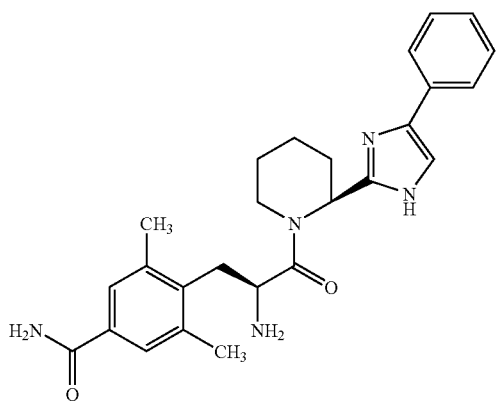

A. {1-(4-carbamoyl-2,6-dimethyl-benzyl)-2-oxo-2-[2-(4-phenyl-1H-imidazol-2-yl)-piperidin-1-yl]-ethyl}-carbamic acid tert-butyl ester

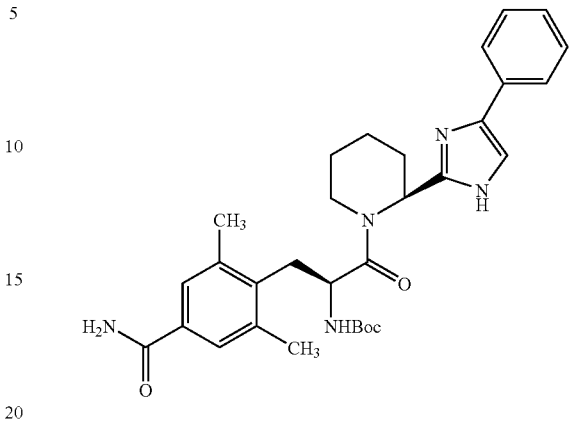

2-tert-Butoxycarbonylamino-3-(4-carbamoyl-2,6-dimethyl-phenyl)-propionic acid (0.42 g, 1.25 mmol) was dissolved in DMF (5 mL) followed by 1-hydroxybenzotriazole (0.34 g, 1.75 mmol), and the resulting solution was cooled to 0° C. To this reaction mixture was added 2-(4-phenyl-1H-imidazol-2-yl)-piperidine (0.31 g, 1.75 mmol) followed by (4-dimethylamino-butyl)-ethyl-carbodiimide (0.34 g, 1.75 mmol). The reaction was then warmed to room temperature and stirred for 16 hours. The reaction mixture was then combined with 2N citric acid and washed multiple times with ethyl acetate. The combined organics were washed with saturated aqueous NaHCO3, dried over Na2SO4, filtered, and concentrated under reduced pressure to yield 600 mg of desired product {1-(4-carbamoyl-2,6-dimethyl-benzyl)-2-oxo-2-[2-(4-phenyl-1H-imidazol-2-yl)-piperidin-1-yl]-ethyl}-carbamic acid tert-butyl ester as a glass which was used as is without further purification. (TLC: 5:1 CHCl3:MeOH Rf=0.6)

B. 4-{2-amino-3-oxo-3-[2-(4-phenyl-1H-imidazol-2-yl)-piperidin-1-yl]-propyl}-3,5-dimethyl-benzamide

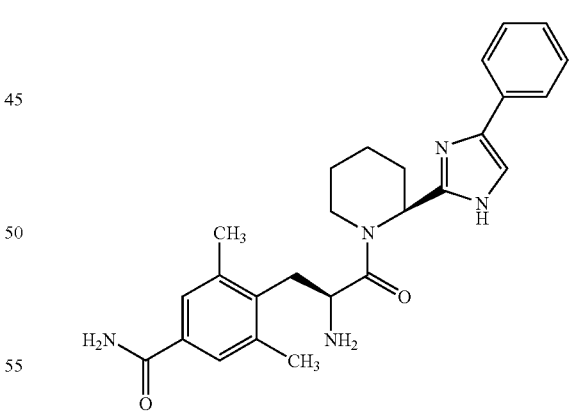

To {1-(4-carbamoyl-2,6-dimethyl-benzyl)-2-oxo-2-[2-(4-phenyl-1H-imidazol-2-yl)-piperidin-1-yl]-ethyl}-carbamic acid tert-butyl ester (0.60 g, 1.10 mmol) was added 0° C. trifluoroactic acid (4 mL). The resulting solution was warmed to room temperature, and after 30 minutes the excess trifluoroacetic acid was removed under a stream of nitrogen. This material was purified via a Gilson preparative HPLC resulting in the isolation of desired product 4-{2-amino-3-oxo-3-[2-(4-phenyl-1H-imidazol-2-yl)-piperidin-

Example 17

2-Amino-3-(4-hydroxy-phenyl)-1-[2-(5-phenyl-ox-azol-2-yl)-piperidin-1-yl]-propan-1-one

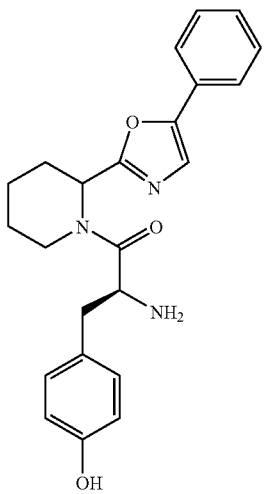

A. {1-(4-tert-Butoxy-benzyl)-2-oxo-2-[2-(5-phenyl-oxazol-2-yl)-piperidin-1-yl]-ethyl}-carbamic acid tert-butyl ester

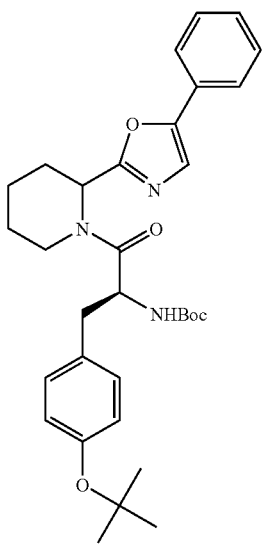

To a mixture of 0.20 g (0.88 mmol) of 2-(5-phenyl-oxazol-2-yl)-piperidine, 0.36 g (1.05 mmol) of 2-tert-Butoxycarbonylamino-3-(4-tert-butoxy-phenyl)-propionic acid, 0.49 g (1.05 mmol) of PyBrop and 0.287 mL of diisopropylethylamine was added 1 ml of dimethylformamide. The resulting mixture was allowed to stir under argon at room temperature overnight. The following morning, LC analysis indicated that about 20% of starting material remained. An additional 0.09 g (0.26 mmol) of 2-tert-Butoxycarbonylamino-3-(4-tert-butoxy-phenyl)-propionic acid, 0.12 g (0.26 mmol) of PyBrop and 0.072 ml (0.45 mmol) of diisopropylethylamine was added. After stirring for 3 hours, the mixture was partitioned between ethyl acetate and water. The organic layer was separated, washed with water, dried over magnesium sulfate and concentrated. The product was taken to the next step as is without further purification.

B. 2-Amino-3-(4-hydroxy-phenyl)-1-[2-(5-phenyl-oxazol-2-yl)-piperidin-1-yl]-propan-1-one

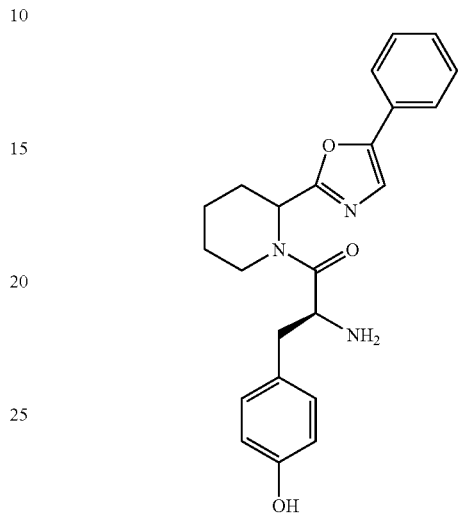

To a solution of 0.88 mmol of the product from step A and 3 mL of chloroform, cooled in an ice bath, was added 3 mL of trifluoroacetic acid. The mixture was allowed to slowly return to room temperature and stir for two hours. LC analysis indicated that the reaction was complete. The mixture was concentrated and the concentrate was purified by prep LC. Obtained 126 mg (0.25 mmol, 28% yield) of the product as a white powder, which was 88% pure by LC. The product was assumed to be a TFA salt.

Using the procedures of the Examples above and the appropriate reagents, starting materials and purification methods known to those skilled in the art, other compounds of the present invention may be prepared including, but hot limited to:

TABLE 3

Mass Spectral Data for Selected Compounds

| Cmpd | Theoretical MW | Measured MW (MH$^+$) |
|---|---|---|
| 1 | 445.6 | 446 |
| 2 | 535.6 | 536.3 |
| 3 | 500.6 | 501.1 |
| 4 | 445.6 | 446 |
| 5 | 453.6 | 454 |
| 6 | 445.6 | 446 |
| 7 | 417.5 | 418.1 |
| 8 | 399.5 | 400.3 |
| 9 | 418.5 | 419.2 |
| 10 | 416.5 | 417.3 |
| 11 | 460.6 | 461.3 |
| 12 | 502.7 | 503 |
| 13 | 493.6 | 494.1 |
| 14 | 461.6 | 462 |
| 15 | 417.5 | 418 |
| 16 | 405.5 | 406 |
| 17 | 435.5 | 436 |
| 18 | 403.5 | 404 |
| 19 | 420.5 | 421.4 |

TABLE 3-continued

Mass Spectral Data for Selected Compounds

| Cmpd | Theoretical MW | Measured MW (MH+) |
|---|---|---|
| 20 | 392.5 | 393.3 |
| 21 | 431.5 | 432.7 |
| 22 | 390.9 | 391 |
| 24 | 426.5 | 427.4 |
| 25 | 404.5 | 405.1 |
| 26 | 494.6 | 495 |
| 27 | 432.6 | 433 |
| 28 | 432.6 | 433 |
| 29 | 432.6 | 433 |
| 30 | 389.5 | 390 |
| 31 | 400.5 | 401 |
| 32 | 400.5 | 401 |
| 33 | 446.6 | 447 |
| 34 | 418.5 | 419 |
| 37 | 446.6 | 447.3 |
| 38 | 417.6 | 418 |
| 101 | 487.6 | 487.9 |
| 102 | 548.7 | 549.1 |
| 103 | 493.6 | 494.1 |
| 104 | 501.61 | 502 |
| 105 | 493.61 | 494.1 |
| 106 | 466.5 | 467.1 |
| 109 | 474.5 | 475.4 |
| 110 | 464.6 | 465.3 |
| 111 | 541.7 | 542.2 |
| 112 | 509.6 | 510.1 |
| 113 | 508.6 | 509.4 |
| 114 | 515.6 | 516.1 |
| 115 | 465.6 | 466.4 |
| 116 | 550.7 | 551.2 |
| 117 | 479.6 | 480.4 |
| 118 | 479.6 | 480 |
| 120 | 481.6 | 482 |
| 121 | 452.6 | 453.1 |
| 122 | 542.7 | 543 |
| 127 | 480.6 | 481 |
| 128 | 536.7 | 537 |
| 129 | 483.5 | 484 |
| 130 | 452.6 | 453 |
| 131 | 466.6 | 467 |
| 132 | 545.5 | 547 |
| 133 | 501.0 | 501 |
| 134 | 528.7 | 529 |
| 135 | 528.7 | 529 |
| 136 | 466.6 | 467 |
| 137 | 466.6 | 467 |
| 138 | 480.6 | 481 |
| 140 | 494.6 | 495.6 |
| 141 | 493.6 | 494 |
| 142 | 451.6 | 452 |
| 143 | 454.5 | 455.2 |
| 144 | 457.0 | 457 |
| 145 | 452.6 | 453 |
| 146 | 494.6 | 495 |
| 147 | 480.6 | 481 |
| 148 | 628.7 | 629.3 |
| 149 | 480.6 | 481.2 |
| 153 | 452.6 | 453 |
| 154 | 466.6 | 467.1 |
| 155 | 466.6 | 467.3 |
| 156 | 466.6 | 467.1 |
| 157 | 466.6 | 467.3 |
| 158 | 418.5 | 419 |
| 160 | 447.5 | 448 |
| 161 | 438.5 | 439 |
| 162 | 493.6 | 494 |
| 201 | 437.5 | 438 |
| 202 | 480.6 | 481.2 |
| 304 | 402.5 | 403 |
| 305 | 450.6 | 451 |
| 306 | 450.5 | 451 |

BIOLOGICAL EXAMPLES

Opioid receptor binding affinity for the compounds of the present invention were determined according to the following procedures and the indicated results were obtained.

Example 1

Rat Brain Delta Opioid Receptor Binding Assay

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenize is diluted to a concentration of 1 g of forebrain tissue per 80 mL Tris and centrifuged at 39,000×g for 10 min. The pellet is resuspended in the same volume of Tris buffer containing 5 mM $MgCl_2$ with several brief pulses from a Polytron homogenizer. This particulate preparation is used for the delta opioid binding assays. Following incubation with the delta selective peptide ligand ~4 nM [$^3$H]DPDPE at 25° C. for 2.5 h in a 96-well plate with total volume of 1 ml, the plate contents are filtered through Wallac filtermat B sheets on a Tomtec 96-well harvester. The filters are rinsed three times with 2 mL of 10 mM HEPES (pH7.4), and dried in a microwave oven 1:45 min twice. To each sample area 2×40 µl of Betaplate Scint scintillation fluid (LKB) is added and analyzed on a LKB (Wallac) 1205 BetaPlate liquid scintillation counter.

The data are used to calculate either the % inhibition compared to control binding (when only a single concentration of test compound is evaluated) or a $K_i$ value (when a range of concentrations is tested). % inhibition is calculated as: [(total dpm-test compound dpm dpm)/(total dpm-nonspecific dpm)]*100. Kd and Ki values were calculated using GraphPad PRISM data analysis program.

Example 2

Rat Brain mu Opioid Receptor Binding Assay

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenize is diluted to a concentration of 1 g of forebrain tissue per 80 mL Tris and centrifuged at 39,000×g for 10 min. The pellet is resuspended in the same volume of Tris buffer containing 5 mM $MgCl_2$ with several brief pulses from a Polytron homogenizer. This particulate preparation is used for the mu-opioid binding assays. Following incubation with the mu selective peptide ligand ~0.8 nM [$^3$H]DAMGO at 25° C. for 2.5 h in a 96-well plate with total 1 ml, the plate contents are filtered through Wallac filtermat B sheets on a Tomtec 96-well harvester. The filters are rinsed three times with 2 mL of 10 mM HEPES (pH7.4), and dried in a microwave oven 1:45 min twice. To each sample area 2×40 µl of Betaplate Scint scintillation fluid (LKB) is added and analyzed on a LKB (Wallac) 1205 BetaPlate liquid scintillation counter.

The data are used to calculate either the % inhibition compared to control binding (when only a single concentration of test compound is evaluated) or a $K_i$ value (when a range of concentrations is tested). % inhibition is calculated as: [(total dpm-test compound dpm dpm)/(total dpm-nonspecific dpm)]*100. Kd and Ki values were calculated using GraphPad PRISM data analysis program.

Biological activity measured for select compounds of the present invention are listed in Table 1 below, including δ- and μ-opioid receptor binding ($K_i$), as determined from a single set of experiments using the procedures outlined above.

TABLE 1

Biological Activity of Phenyl Heterocyclic Compounds

| Cmpd | δ-opioid binding (nM) | μ-opioid binding (nM) |
|---|---|---|
| 1 | 20.9 | 0.15 |
| 2 | 121 | 3 |
| 3 | 10000 | 10000 |
| 4 | 764 | 135 |
| 5 | 6180 | 40.8 |
| 6 | 13.9 | 0.13 |
| 7 | 6070 | 88.3 |
| 8 | 10000 | 207 |
| 9 | 606 | 26.8 |
| 10 | 932.6 | 23.6 |
| 11 | 6.7 | 0.16 |
| 12 | 11.9 | 0.17 |
| 13 | 656 | 27.7 |
| 14 | 5135 | 9.3 |
| 15 | 65.3 | 2.6 |
| 16 | 5328 | 115 |
| 17 | 5118 | 320 |
| 18 | 7524 | 409 |
| 19 | 46.3 | 0.14 |
| 20 | 10000 | 231 |
| 21 | 33.9 | 0.22 |
| 22 | 433 | 16 |
| 24 | 5663 | 9.27 |
| 25 | 107 | 1.69 |
| 26 | 628 | 87 |
| 27 | 1000 | 8.56 |
| 28 | 21.5 | 0.3 |
| 29 | 0.51 | 0.09 |
| 30 | 1019 | 57.2 |
| 31 | 10000 | 565 |
| 32 | 5899 | 541 |
| 33 | 273 | 42.9 |
| 34 | 1.86 | 0.05 |
| 35 | 476 | 869 |
| 37 | 5233 | 13.3 |
| 38 | 1187 | 734 |
| 101 | 37 | 169 |
| 102 | 5350 | 1235 |
| 103 | 578 | 900 |
| 104 | 174 | 592 |
| 105 | 0.06 | 1.44 |
| 106 | 5203 | 5776 |
| 109 | 12.6 | 167 |
| 110 | 30.4 | 413 |
| 111 | 103 | 293 |
| 112 | 43.7 | 92.3 |
| 113 | 0.2 | 0.5 |
| 114 | 342 | 356 |
| 115 | 1.3 | 23.2 |
| 116 | 3.5 | 9.6 |
| 117 | 1.61 | 23.6 |
| 118 | 0.73 | 23.1 |
| 120 | 674 | 1349 |
| 121 | 1.32 | 38 |
| 122 | 346 | 2523 |
| 127 | 0.4 | 7.1 |
| 128 | 5.2 | 213 |
| 129 | 50000 | 25707 |
| 130 | 466 | 912 |
| 131 | 0.09 | 0.3 |

TABLE 1-continued

Biological Activity of Phenyl Heterocyclic Compounds

| Cmpd | δ-opioid binding (nM) | μ-opioid binding (nM) |
|---|---|---|
| 132 | 0.1 | 0.17 |
| 133 | 0.12 | 0.18 |
| 134 | 10000 | 329 |
| 135 | 185 | 10000 |
| 136 | 116 | 229 |
| 137 | 3.89 | 368 |
| 138 | 397 | 10000 |
| 140 | 1 | 69 |
| 141 | 34 | 207 |
| 142 | 93 | 857 |
| 143 | 687 | 12769 |
| 144 | 1130 | 5264 |
| 145 | 1.18 | 59.1 |
| 146 | 668 | 817 |
| 147 | 43 | 150 |
| 148 | 6 | 922 |
| 149 | 0.8 | 3.0 |
| 154 | 10000 | 10000 |
| 155 | 0.44 | 23.2 |
| 156 | 28.0 | 178.6 |
| 157 | 0.57 | 30 |
| 158 | 5.43 | 0.15 |
| 160 | 752 | 1335 |
| 161 | 133 | 480 |
| 162 | 1.7 | 6.5 |
| 201 | 208 | 11350 |
| 202 | 60.9 | 5323 |
| 304 | 26961 | 28277 |
| 305 | 25827 | 2311 |
| 306 | 27090 | 50000 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (Ia):

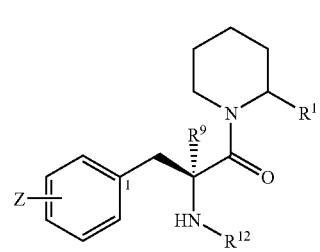

Formula (Ia)

Wherein:

$R^1$ is

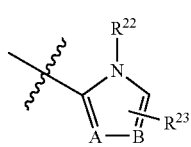

a-1 wherein

A-B is selected from the group consisting of N—C and C—N;

$R^{22}$ is a substituent attached to a ring nitrogen and is selected from the group consisting of hydrogen, $C_{1-4}$alkyl and aryl;

$R^{23}$ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—$R^{40}$)—C(O)—NH$_2$ and $C_{1-6}$alkyl {wherein said alkyl is optionally substituted with a substituent selected from the group consisting of hydroxy, hydroxycarbonyl, $C_{1-4}$alkoxycarbonyl, aminocarbonyl, amino, aryl, $(C_{1-4})$alkylaminocarbonyl, di$(C_{1-4})$alkylaminocarbonyl, heteroarylamino, heteroaryloxy, aryl$(C_{1-4})$alkoxy, and heteroaryl};

$R^{40}$ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, di$C_{1-6}$alkylcarbonylamino, aryl$(C_{1-6})$alkyl, heteroaryl$(C_{1-6})$alkyl, aryl, and heteroaryl;

$R^9$ is selected from the group consisting of hydrogen and $C_{1-6}$alkyl;

$R^{12}$ is independently selected from the group consisting of hydrogen, $C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl$(C_{1-6})$alkyl, heteroaryl$(C_{1-6})$alkyl, aryl, and heteroaryl, wherein when $R^{12}$ is selected from $C_{1-6}$alkyl, $R^{12}$ may be optionally fused to Ar; and Z is one to four substituents independently selected from the group consisting of halogen, $C_{1-6}$alkyl, nitro, cyano, heteroaryl, heterocyclyl, —(CH$_2$)$_q$C(W)R$^{17}$, —(CH$_2$)$_q$COOR$^{17}$, —(CH$_2$)$_q$C(W)NR$^{17}$R$^{18}$, —(CH$_2$)$_q$NR$^{17}$R$^{18}$, —(CH$_2$)$_q$NR$^{19}$C(W)R$^{17}$, —(CH$_2$)$_q$NR$^{19}$SO$_2$R$^{17}$, —(CH$_2$)$_q$NR$^{19}$C(W)NR$^{17}$R$^{18}$, —S(O)$_q$R$^{17}$, —(CH$_2$)$_q$SO$_2$NR$^{17}$R$^{18}$, and —(CH$_2$)$_q$NR$^{19}$CWR$^{17}$;

wherein q is an integer from 0 to 2;

W is selected from the group consisting of O, S, and NR$^{20}$;

$R^{17}$ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di$(C_{1-4})$alkylaminocarbonyl, amino, $C_{1-4}$alkylamino, di$(C_{1-4})$alkylamino, phenyl and heteroaryl); provided that when $R^{17}$ is heterocyclyl and contains a N atom, the point of attachment for said heterocyclyl ring is a carbon atom;

$R^{18}$, $R^{19}$ and $R^{20}$ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di$(C_{1-4})$alkylaminocarbonyl, amino, $C_{1-4}$alkylamino, di$(C_{1-4})$alkylamino, phenyl and heteroaryl);

when $R^{17}$ and $R^{18}$ are $C_{1-6}$alkyl optionally substituted with hydroxy, $C_{1-4}$alkoxy, amino or $C_{1-4}$amino and are present on the same substituent group, $R^{17}$ and $R^{18}$ can optionally be taken together to form a 5- to 8-membered ring;

additionally, if $R^{17}$ or $R^{18}$ are $C_{1-6}$alkyl optionally substituted with a hydroxy, $C_{1-4}$alkoxy, amino, or $C_{1-4}$alkylamino $R^{17}$ and $R^{18}$ may be optionally fused to Ar;

and pharmaceutically acceptable enantiomers, diastereomers and salts thereof.

2. A compound of claim 1 wherein $R^9$ is selected from the group consisting of hydrogen and methyl.

3. A compound of claim 1 wherein $R^{12}$ is selected from the group consisting of hydrogen and methyl.

4. A compound of claim 1 wherein Z is one to three substituents independently selected from the group consisting of $C_{1-6}$alkyl, and —(CH$_2$)$_q$C(W)NR$^{17}$R$^{18}$.

5. A compound of Formula (Ia):

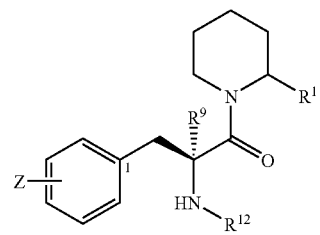

Formula (Ia)

Wherein $R^1$, Z, $R^9$ and $R^{12}$ are selected from:

| Cmpd | $R^1$ | Z | $R^9$ | $R^{12}$ |
|---|---|---|---|---|
| 1 | imidazole-Ph | 4-C(O)NHCH$_2$Me | H | H |
| 2 | imidazole-Ph | 4- | H | H |

-continued
| Cmpd | R¹ | Z | R⁹ | R¹² |
|---|---|---|---|---|
| 3 | 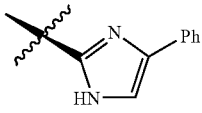 | 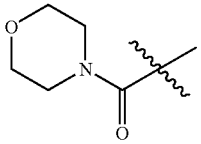 4- | H | H |
| | |  | | |
| 4 | 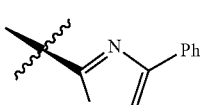 | 4-C(O)NMe$_2$ | H | H |
| 5 | 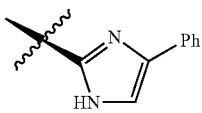 | 4-SO$_2$NH$_2$ | H | H |
| 6 | 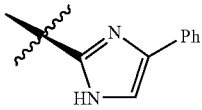 | 2,6-diMe-4-C(O)NH$_2$ | H | H |
| 7 | 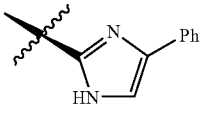 | 3-C(O)NH$_2$ | H | H |
| 8 | 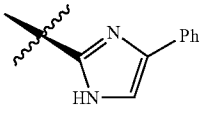 | 3-CN | H | H |
| 9 | 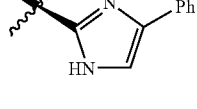 | 4-CO$_2$H | H | H |
| 10 | 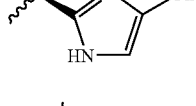 | 4-C(O)Me | H | H |
| 11 | | 4-OC(O)Me | H | H |

-continued

| Cmpd | R¹ | Z | R⁹ | R¹² |
|---|---|---|---|---|
| 12 | 2-(4-Ph-imidazolyl) | 4-OC(O)t-Bu | H | H |
| 13 | 2-(4-Ph-imidazolyl) | 4-C(O)NHPh | H | H |
| 14 | 2-(4-Ph-imidazolyl) | 4-C(O)NHCH$_2$CH$_2$OH | H | H |
| 15 | 2-(4-Ph-imidazolyl) | 4-C(O)NH$_2$ | H | H |
| 18 | 2-(4-Ph-imidazolyl) | 4-CH$_2$NH$_2$ | H | H |
| 21 | 2-(4-Ph-imidazolyl) | 4-C(O)NHMe | H | H |
| 26 | 2-(4-Ph-imidazolyl) | 4-OCH$_2$Ph | Me | H |
| 27 | 2-(4-Ph-imidazolyl) | 2,6-diMe-4-OMe | H | H |
| 30 | 2-(4-Ph-imidazolyl) | 4-NH$_2$ | H | H |
| 33 | 2-(4-Ph-imidazolyl) | 2,6-diMe-4-OMe | H | Me |
| 35 | 2-(4-Ph-imidazolyl) | 4-CN | H | H |
| 203 | 2-(4-Ph-imidazolyl) | 2-furyl | H | H |

-continued

| Cmpd | R¹ | Z | R⁹ | R¹² |
|---|---|---|---|---|
| 204 | 2-(4-phenyl-1H-imidazolyl) | thiomorpholine-N-C(O)- | H | H |
| 205 | 2-(4-phenyl-1H-imidazolyl) | piperidine-N-C(O)- | H | H |
| 206 | 2-(4-phenyl-1H-imidazolyl) | 4-C(O)NHCH$_2$Me | H | H |
| 207 | 2-(4-phenyl-1H-imidazolyl) | 4-C(O)NH(CH$_2$)$_2$Me | H | H |
| 208 | 2-(4-phenyl-1H-imidazolyl) | 4-C(O)NH(CH$_2$)$_2$OMe | H | H |
| 209 | 2-(4-phenyl-1H-imidazolyl) | 4-C(O)NHCH(CH$_3$)$_2$ | H | H |
| 210 | 2-(4-phenyl-1H-imidazolyl) | morpholine-N-C(O)- | H | H |
| 211 | 2-(4-phenyl-1H-imidazolyl) | 4-C(O)NHCH$_2$Me | H | H |
| 212 | 2-(4-phenyl-1H-imidazolyl) | 4-C(O)NHCH$_3$ | H | H |
| 213 | 2-(4-phenyl-1H-imidazolyl) | pyrrolidine-N-C(O)- | H | H | and pharmaceutically acceptable enantiomers, diastereomers and salts thereof.

6. A compound of Formula (Ib):

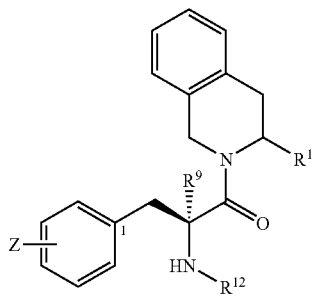

Formula (Ib)

Wherein:
R¹ is

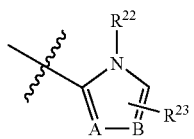

a-1 wherein
A-B is selected from the group consisting of N—C and C—N;
R²² is a substituent attached to a ring nitrogen and is selected from the group consisting of hydrogen, $C_{1-4}$alkyl and aryl;
R²³ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—R⁴⁰)—C(O)—NH₂ and $C_{1-6}$alkyl {wherein said alkyl is optionally substituted with a substituent selected from the group consisting of hydroxy, hydroxycarbonyl, $C_{1-4}$alkoxycarbonyl, aminocarbonyl, amino, aryl, ($C_{1-4}$)alkylaminocarbonyl, di($C_{1-4}$)alkylaminocarbonyl, heteroarylamino, heteroaryloxy, aryl$C_{1-4}$)alkoxy, and heteroaryl};
R⁴⁰ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl;
R⁹ selected from the group consisting of hydrogen and $C_{1-6}$alkyl;
R¹² is independently selected from the group consisting of hydrogen, $C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl, wherein when R¹² is selected from $C_{1-6}$alkyl, R¹² may be optionally fused to Ar; and
Z is one to four substituents independently selected from the group consisting of halogen, $C_{1-6}$alkyl, nitro, cyano, heteroaryl, heterocyclyl, —(CH₂)$_q$C(W)R¹⁷, —(CH₂)$_q$COOR¹⁷, —(CH₂)$_q$C(W)NR¹⁷R¹⁸, —(CH₂)$_q$NR¹⁷R¹⁸, —(CH₂)$_q$NR¹⁹C(W)R¹⁷, —(CH₂)$_q$NR¹⁹SO₂R¹⁷, —(CH₂)$_q$NR¹⁹C(W)NR¹⁷R¹⁸, —S(O)$_q$R¹⁷, —(CH₂)$_q$SO₂NR¹⁷R¹⁸, and —(CH₂)$_q$NR¹⁹CWR¹⁷;
wherein q is an integer from 0 to 2;
W is selected from the group consisting of O, S, and NR²⁰;

R¹⁷ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl); provided that when R¹⁷ is heterocyclyl and contains a N atom, the point of attachment for said heterocyclyl ring is a carbon atom;

R¹⁸, R¹⁹ and R²⁰ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl);

when R¹⁷ and R¹⁸ are $C_{1-6}$alkyl optionally substituted with hydroxy, $C_{1-4}$alkoxy, amino or $C_{1-4}$amino and are present on the same substituent group, R¹⁷ and R¹⁸ can optionally be taken together to form a 5- to 8-membered ring;

additionally, if R¹⁷ or R¹⁸ are $C_{1-6}$alkyl optionally substituted with a hydroxy, $C_{1-4}$alkoxy, amino, or $C_{1-4}$alkylamino R¹⁷ and R¹⁸ may be optionally fused to Ar;

and pharmaceutically acceptable enantiomers, diastereomers and salts thereof.

7. A compound of claim 6 wherein R⁹ is selected from the group consisting of hydrogen and methyl.

8. A compound of claim 6 wherein R¹² is selected from the group consisting of hydrogen and methyl.

9. A compound of claim 6 wherein Z is one to three substituents independently selected from the group consisting of $C_{1-6}$alkyl, and —(CH₂)$_q$C(W)NR¹⁷R¹⁸.

10. A compound of Formula (Ib):

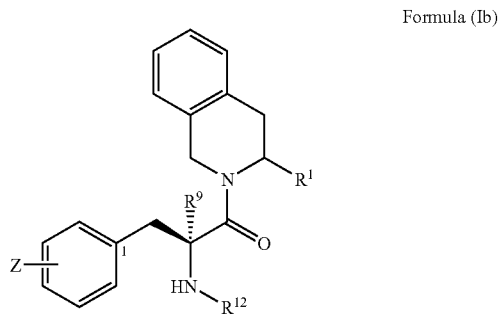

Formula (Ib)

Wherein R¹, Z, R⁹ and R¹² are selected from:

| Cmpd | R¹ | Z | R⁹ | R¹² |
|---|---|---|---|---|
| 101 | imidazole-Ph | 4-morpholine-C(O)-C(Me)₂- | H | H |
| 102 | imidazole-Ph | 4-(4-Me-piperazine)-C(O)- | H | H |
| 103 | imidazole-Ph | 4-C(O)NMe₂ | H | H |
| 104 | imidazole-Ph | 4-SO₂NH₂ | H | H |
| 105 | imidazole-Ph | 2,6-diMe-4-C(O)NH₂ | H | H |
| 106 | imidazole-Ph | 4-CO₂H | H | H |
| 111 | imidazole-Ph | 4-C(O)NHPh | H | H |
| 112 | imidazole-Ph | 4-C(O)NHCH₂CH₂OH | H | H |
| 113 | imidazole-Ph | 2,6-diMe-4-OC(O)Me | H | H |
| 114 | imidazole-Ph | 4-NHSO₂Me | H | H |
| 115 | imidazole-Ph | 4-C(O)NH₂ | H | H |

-continued

| Cmpd | R¹ | Z | R⁹ | R¹² |
|---|---|---|---|---|
| 116 | 2-Ph-imidazole (HN) | 2,6-diMe-4-OC(O)t-Bu | H | H |
| 117 | 2-Ph-imidazole (HN) | 4-C(O)NHMe | H | H |
| 118 | 4-Ph-5-Me-imidazole (HN) | 4-C(O)NH$_2$ | H | H |
| 120 | 4-Ph-5-Me-imidazole (HN) | 4-NO$_2$ | H | H |
| 122 | 2-Ph-imidazole (HN) | 4-OCH$_2$Ph | Me | H |
| 128 | 2-Ph-imidazole (HN) | 4-OC(O)t-Bu | H | Me |
| 130 | 2-Ph-imidazole (HN) | 4-CH$_2$OH | H | H |
| 141 | 4-Ph-5-Me-imidazole (HN) | 4-NHC(O)Me | H | H |
| 142 | 4-Ph-5-Me-imidazole (HN) | 4-NH$_2$ | H | H |
| 143 | 4-Ph-5-Me-imidazole (HN) | 4-F | H | H |
| 144 | 2-Ph-imidazole (HN) | 4-Cl | H | H |

-continued

| Cmpd | R¹ | Z | R⁹ | R¹² |
|---|---|---|---|---|
| 160 | 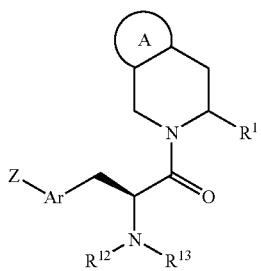 | 4-CN | H | H |
| 162 | 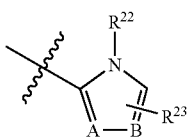 | —C(O)NHCH₂Me | H | H | and pharmaceutically acceptable enantiomers, diastereomers and salts thereof.

11. A compound of Formula (Ic):

Formula (Ic)

Wherein:
A is phenyl;
$R^1$ is a-1 wherein
A-B is selected from the group consisting of N—C and C—N;
$R^{22}$ is a substituent attached to a ring nitrogen and is selected from the group consisting of hydrogen, $C_{1-4}$alkyl and aryl;
$R^{23}$ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—$R^{40}$)—C(O)—NH₂ and $C_{1-6}$alkyl {wherein said alkyl is optionally substituted with a substituent selected from the group consisting of hydroxy, hydroxycarbonyl, $C_{1-4}$alkoxycarbonyl, aminocarbonyl, amino, aryl, ($C_{1-4}$)alkylaminocarbonyl, di($C_{1-4}$)alkylaminocarbonyl, heteroarylamino, heteroaryloxy, aryl($C_{1-4}$)alkoxy, and heteroaryl};
$R^{40}$ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl;

$R^{12}$ and $R^{13}$ are each independently selected from the group consisting of hydrogen, $C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl, wherein when $R^{12}$ and $R^{13}$ are selected from $C_{1-6}$alkyl, $R^{12}$ and $R^{13}$ may be optionally fused to Ar;

Ar is selected from the group consisting of phenyl, naphthyl and heteroaryl, wherein said phenyl is substituted with at least one and up to four Z substituents other than hydrogen and said naphthyl or heteroaryl is optionally substituted with one to four Z substituents;

Z is one to four substituents independently selected from the group consisting of halogen, hydrogen, $C_{1-6}$alkyl, nitro, cyano, heteroaryl, heterocyclyl, —(CH₂)$_q$C(W)$R^{17}$, —(CH₂)$_q$COOR$^{17}$, —(CH₂)$_q$C(W)NR$^{17}$R$^{18}$, —(CH₂)$_q$NR$^{17}$R$^{18}$, —(CH₂)$_q$N$^{19}$C(W)R$^{17}$, —(CH₂)$_q$NR$^{19}$SO₂R$^{17}$, —(CH₂)$_q$NR$^{19}$C(W)NR$^{17}$R$^{18}$, —S(O)$_q$R$^{17}$, —(CH₂)$_q$SO₂NR$^{17}$R$^{18}$, and —(CH₂)$_q$NR$^{19}$CWR$^{17}$;

wherein q is an integer from 0 to 2;
W is selected from the group consisting of O, S, and NR²⁰;
$R^{17}$ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl); provided that when $R^{17}$ is heterocyclyl and contains a N atom, the point of attachment for said heterocyclyl ring is a carbon atom;

$R^{18}$, $R^{19}$ and $R^{20}$ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$alkylamino, phenyl and heteroaryl);

when $R^{17}$ and $R^{18}$ are $C_{1-6}$alkyl optionally substituted with hydroxy, $C_{1-4}$alkoxy, amino or $C_{1-4}$amino and are present on the same substituent group, $R^{17}$ and $R^{18}$ can optionally be taken together to form a 5- to 8-membered ring;

additionally, if $R^{17}$ or $R^{18}$ are $C_{1-6}$alkyl optionally substituted with a hydroxy, $C_{1-4}$alkoxy, amino, or $C_{1-4}$alkylamino $R^{17}$ and $R^{18}$ may be optionally fused to Ar;

and pharmaceutically acceptable enantiomers, diastereomers and salts thereof.

12. A compound of Fomula I(d)

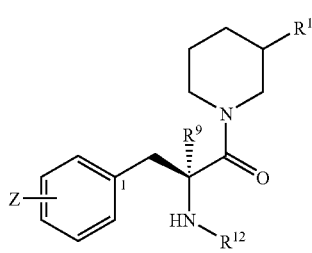

Formula (Id)

wherein
$R^1$ is

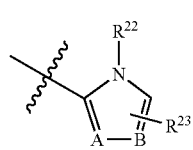

a-1 wherein
A-B is selected from the group consisting of N—C and C—N;

$R^{22}$ is a substituent attached to a ring nitrogen and is selected from the group consisting of hydrogen, $C_{1-4}$alkyl and aryl;

$R^{23}$ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—$R^{40}$)—C(O)—NH$_2$ and $C_{1-6}$alkyl {wherein said alkyl is optionally substituted with a substituent selected from the group consisting of hydroxy, hydroxycarbonyl, $C_{1-4}$alkoxycarbonyl, aminocarbonyl, amino, aryl, ($C_{1-4}$)alkylaminocarbonyl, di($C_{1-4}$)alkylaminocarbonyl, heteroarylamino, heteroaryloxy, aryl($C_{1-4}$)alkoxy, and heteroaryl};

$R^{40}$ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl;

$R^{12}$ is selected from the group consisting of hydrogen, $C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl, wherein when $R^{12}$ and $R^{13}$ are selected from $C_{1-6}$alkyl, $R^{12}$ and $R^{13}$ may be optionally fused to Ar;

Z is one to four substituents independently selected from the group consisting of halogen, $C_{1-6}$alkyl, nitro, cyano, heteroaryl, heterocyclyl, —(CH$_2$)$_q$C(W)R$^{17}$, —(CH$_2$)$_q$COOR$^{17}$, —(CH$_2$)$_q$C(W)NR$^{17}$R$^{18}$, —(CH$_2$)$_q$NR$^{17}$R$^{18}$, —(CH$_2$)$_q$NR$^{19}$C(W)R$^{17}$, —(CH$_2$)$_q$NR$^{19}$SO$_2$R$^{17}$, —(CH$_2$)$_q$NR$^{19}$C(W)NR$^{17}$R$^{18}$, —S(O)$_q$R$^{17}$, —(CH$_2$)$_q$SO$_2$NR$^{17}$R$^{18}$, and —(CH$_2$)$_q$NR$^{19}$CWR$^{17}$;

wherein q is an integer from 0 to 2;

W is selected from the group consisting of O, S, and NR$^{20}$;

$R^{17}$ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl); provided that when $R^{17}$ is heterocyclyl and contains a N atom, the point of attachment for said heterocyclyl ring is a carbon atom;

$R^{18}$, $R^{19}$ and $R^{20}$ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl);

when $R^{17}$ and $R^{18}$ are $C_{1-6}$alkyl optionally substituted with hydroxy, $C_{1-4}$alkoxy, amino or $C_{1-4}$amino and are present on the same substituent group, $R^{17}$ and $R^{18}$ can optionally be taken together to form a 5- to 8-membered ring;

additionally, if $R^{17}$ or $R^{18}$ are $C_{1-6}$alkyl optionally substituted with a hydroxy, $C_{1-4}$alkoxy, amino, or $C_{1-4}$alkylamino $R^{17}$ and $R^{18}$ may be optionally fused to Ar;

and pharmaceutically acceptable enantiomers, diastereomers and salts thereof.

13. A compound of claim 12 wherein $R^9$ is selected from the group consisting of hydrogen and methyl.

14. A compound of claim 12 wherein $R^{12}$ is selected from the group consisting of hydrogen and methyl.

15. A compound of claim 12 wherein Z is one to three substituents independently selected from the group consisting of $C_{1-6}$alkyl, and —(CH$_2$)$_q$C(W)NR$^{17}$R$^{18}$.

16. A compound of formula Id wherein $R^1$, Z, $R^9$ and $R^{12}$ are selected from:

| Cmpd | $R^1$ | Z | $R^9$ | $R^{12}$ |
|---|---|---|---|---|
| 214 | 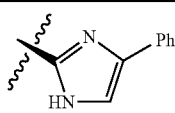 | 2,6-diMe-4-OH | H | H |
| 215 | 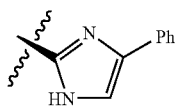 | 2,6-diMe-4-OH | H | H. |

17. A compound of Formula (Ie)

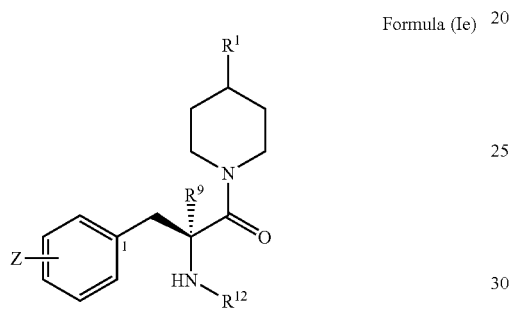

Formula (Ie)

wherein
$R^1$ is

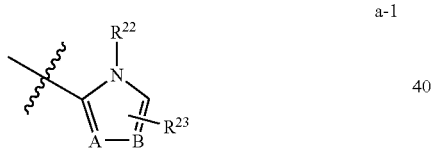

a-1 wherein
- A-B is selected from the group consisting of N—C and C—N;
- $R^{22}$ is a substituent attached to a ring nitrogen and is selected from the group consisting of hydrogen, $C_{1-4}$alkyl and aryl;
- $R^{23}$ is one to two substituents independently selected from the group consisting of hydrogen, halogen, amino, aryl, arylamino, heteroarylamino, hydroxy, aryloxy, heteroaryloxy, an amino acid residue such as —C(O)—NH—CH(—$R^{40}$)—C(O)—NH$_2$ and $C_{1-6}$alkyl {wherein said alkyl is optionally substituted with a substituent selected from the group consisting of hydroxy, hydroxycarbonyl, $C_{1-4}$alkoxycarbonyl, aminocarbonyl, amino, aryl, ($C_{1-4}$)alkylaminocarbonyl, di($C_{1-4}$)alkylaminocarbonyl, heteroarylamino, heteroaryloxy, aryl($C_{1-4}$) alkoxy, and heteroaryl};
- $R^{40}$ is selected from the group consisting of hydrogen, $C_{1-6}$alkyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl;

$R^{12}$ is selected from the group consisting of hydrogen, di$C_{1-6}$alkyl, formyl, $C_{1-6}$alkylcarbonyl, $C_{1-6}$alkoxycarbonyl, $C_{1-6}$alkylcarbonylamino, di$C_{1-6}$alkylcarbonylamino, aryl($C_{1-6}$)alkyl, heteroaryl($C_{1-6}$)alkyl, aryl, and heteroaryl, wherein when $R^{12}$ and $R^{13}$ are selected from $C_{1-6}$alkyl, $R^{12}$ and $R^{13}$ may be optionally fused to Ar;

Z is one to four substituents independently selected from the group consisting of halogen, $C_{1-6}$alkyl, nitro, cyano, heteroaryl, heterocyclyl, —(CH$_2$)$_q$C(W)R$^{17}$, —(CH$_2$)$_q$COOR$^{17}$, —(CH$_2$)$_q$C(W)NR$^{17}$R$^{18}$, —(CH$_2$)$_q$NR$^{17}$R$^{18}$, —(CH$_2$)$_q$NR$^{19}$C(W)R$^{17}$, —(CH$_2$)$_q$NR$^{19}$SO$_2$R$^{17}$, —(CH$_2$)$_q$NR$^{19}$C(W)NR$^{17}$R$^{18}$, —S(O)$_q$R$^{17}$, —(CH$_2$)$_q$SO$_2$NR$^{17}$R$^{18}$, and —(CH$_2$)$_q$NR$^{19}$CWR$^{17}$;

wherein q is an integer from 0 to 2;

W is selected from the group consisting of O, S, and NR$^{20}$;

$R^{17}$ is selected from the group consisting of hydrogen, $C_{1-6}$alkyl, heterocyclyl (optionally substituted with $C_{1-4}$alkyl) and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl); provided that when $R^{17}$ is heterocyclyl and contains a N atom, the point of attachment for said heterocyclyl ring is a carbon atom;

$R^{18}$, $R^{19}$ and $R^{20}$ are each independently selected from the group consisting of hydrogen, $C_{1-6}$alkyl, and $C_{3-8}$cycloalkyl, (wherein said $C_{1-6}$alkyl and $C_{3-8}$cycloalkyl are optionally substituted with $C_{1-4}$alkyl, wherein said $C_{1-6}$alkyl and $C_{3-8}$cycloalkyl and $C_{1-4}$alkyl substituents thereof may also be optionally substituted with a substituent selected from the group consisting of hydroxy, mercapto, $C_{1-4}$alkoxy, hydroxycarbonyl, $C_{1-4}$alkoxycarbonyl, aminocarbonyl, $C_{1-4}$alkylaminocarbonyl, di($C_{1-4}$)alkylaminocarbonyl, amino, $C_{1-4}$alkylamino, di($C_{1-4}$)alkylamino, phenyl and heteroaryl);

when $R^{17}$ and $R^{18}$ are $C_{1-6}$alkyl optionally substituted with hydroxy, $C_{1-4}$alkoxy, amino or $C_{1-4}$amino and are present on the same substituent group, $R^{17}$ and $R^{18}$ can optionally be taken together to form a 5- to 8-membered ring;

additionally, if $R^{17}$ or $R^{18}$ are $C_{1-6}$alkyl optionally substituted with a hydroxy, $C_{1-4}$alkoxy, amino, or $C_{1-4}$alkylamino $R^{17}$ and $R^{18}$ may be optionally fused to Ar;

and pharmaceutically acceptable enantiomers, diastereomers and salts thereof.

18. A compound of claim 17 wherein $R^9$ is selected from the group consisting of hydrogen and methyl.

19. A compound of claim 17 wherein $R^{12}$ is selected from the group consisting of hydrogen and methyl.

20. A compound of claim 17 wherein Z is one to three substituents independently selected from the group consisting of $C_{1-6}$alkyl, and —(CH$_2$)$_q$C(W)NR$^{17}$R$^{18}$.

21. A compound of the formula (Ie)

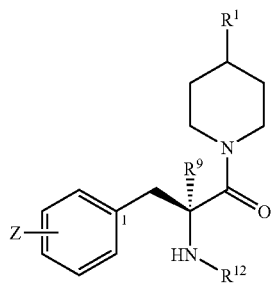

wherein $R^1$, Z, $R^9$ and $R^{12}$ are

| Cmpd | $R^1$ | Z | $R^9$ | $R^{12}$ |
|---|---|---|---|---|
| 216 | | 2,6-diMe-4-OH | H | H. |

22. A compound of Formula (Ia):

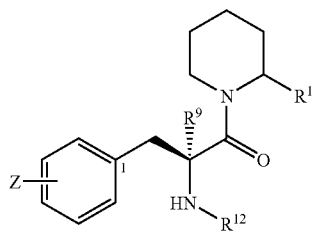

Formula (Ia)

Wherein $R^1$, Z, $R^9$ and $R^{12}$ are selected from:

| Cmpd | $R^1$ | Z | $R^9$ | $R^{12}$ |
|---|---|---|---|---|
| 16 | | 3-NH$_2$-4-OH | H | H |
| 17 | | 3-NO$_2$-4-OH | H | H |
| 24 | | 3,5-diF-4-OH | H | H |
| 25 | | 4-OH | Me | H |

-continued

| Cmpd | $R^1$ | Z | $R^9$ | $R^{12}$ |
|---|---|---|---|---|
| 28 | | 2,6-diMe-4-OH | H | Me |
| 29 | | 2,6-diMe-4-OH | H | H |
| 34 | | 2,6-diMe-4-OH | H | H |
| 37 | | 2,6-diMe-4-OH | H | —C(O)H |
| 158 | | 2,6-diMe-4-OH | H | H | and pharmaceutically acceptable enantiomers, diastereomers and salts thereof.

23. A compound of Formula (Ib):

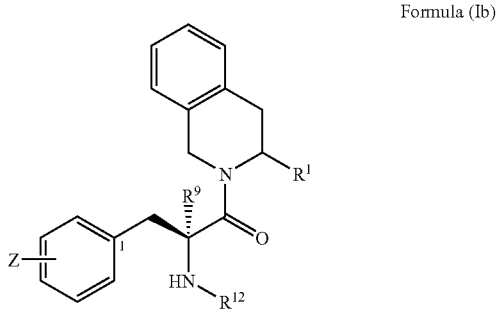

Formula (Ib)

Wherein $R^1$, Z, $R^9$ and $R^{12}$ are selected from:

| Cmpd | $R^1$ | Z | $R^9$ | $R^{12}$ |
|---|---|---|---|---|
| 109 | | 3,5-diF-4-OH | H | H |
| 110 | 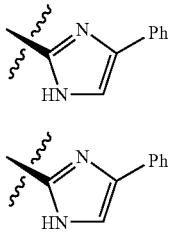 | 4-C(O)Me | H | H |

-continued

| Cmpd | R¹ | Z | R⁹ | R¹² |
|---|---|---|---|---|
| 121 | imidazole-Ph | 4-OH | Me | H |
| 127 | imidazole-Ph | 2,6-diMe-4-OH | H | Me |
| 129 | imidazole-Ph | 3-NO$_2$-4-OH | H | H |
| 131 | imidazole-Ph | 2,6-diMe-4-OH | H | H |
| 132 | imidazole-Ph, Br | 2,6-diMe-4-OH | H | H |
| 133 | imidazole-Ph, Cl | 2,6-diMe-4-OH | H | H |
| 134 | imidazole-Ph | 4-OH | H | —CH$_2$Ph |
| 135 | imidazole-Ph | 4-OH | H | —CH$_2$Ph |
| 136 | imidazole-Ph | 4-OH | H | Et |
| 137 | imidazole-Ph | 4-OH | H | Et |
| 138 | imidazole-Ph | 4-OH | H | i-Pr |
| 140 | imidazole-Ph | 4-C(O)Me | H | Me |

-continued

| Cmpd | R¹ | Z | R⁹ | R¹² |
|---|---|---|---|---|
| 145 | imidazole-Ph | 4-OH | H | Me |
| 146 | imidazole-Ph | 2,6-diMe-4-OMe | H | Me |
| 147 | imidazole-Ph | 2,6-diMe-4-OMe | H | H |
| 148 | imidazole-Ph, R | 4-OH | H | H |
| | R = —C(O)NHCH(CH$_2$Ph)C(O)NH2 | | | |
| 149 | imidazole-Ph, Me | 2,6-diMe-4-OH | H | H |
| 153 | imidazole-Ph | 4-OH | H | Me |
| 154 | imidazole-Ph, Me | 4-OMe | H | H |
| 155 | imidazole-Ph, Me | 4-OH | H | Me |
| 156 | imidazole-Ph, Me | 4-OMe | H | H |
| 157 | imidazole-Ph, Me | 4-OH | H | Me | and pharmaceutically acceptable enantiomers, diastereomers and salts thereof.

24. A method of treating pain in a subject in need thereof comprising administering to the subject a therapeutically effective amount of a compound of claim 1.

25. A method of treating pain in a subject in need thereof comprising administering to the subject a therapeutically effective amount of a compound of claim 6.

26. A method of treating pain in a subject in need thereof comprising administering to the subject a therapeutically effective amount of a compound of claim 11.

27. A method of treating pain in a subject in need thereof comprising administering to the subject a therapeutically effective amount of a compound of claim 12.

28. A method of treating pain in a subject in need thereof comprising administering to the subject a therapeutically effective amount of a compound of claim 17.

29. A pharmaceutical composition comprising an effective amount of a compound of claim 1 and a pharmaceutically acceptable carrier.

30. A pharmaceutical composition comprising an effective amount of a compound of claim 6 and a pharmaceutically acceptable carrier.

31. A pharmaceutical composition comprising an effective amount of a compound of claim 11 and a pharmaceutically acceptable carrier.

32. A pharmaceutical composition comprising an effective amount of a compound of claim 12.

33. A pharmaceutical composition comprising an effective amount of a compound of claim 17.

\* \* \* \* \*